(12) United States Patent
Xu

(10) Patent No.: US 11,708,320 B2
(45) Date of Patent: Jul. 25, 2023

(54) ENVIRONMENTALLY-FRIENDLY HYDROAZIDATION OF OLEFINS

(71) Applicant: GEORGIA STATE UNIVERSITY RESEARCH FOUNDATION, INC., Atlanta, GA (US)

(72) Inventor: Hao Xu, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 13 days.

(21) Appl. No.: 17/253,966

(22) PCT Filed: Jun. 28, 2019

(86) PCT No.: PCT/US2019/039925
§ 371 (c)(1),
(2) Date: Dec. 18, 2020

(87) PCT Pub. No.: WO2020/006476
PCT Pub. Date: Jan. 2, 2020

(65) Prior Publication Data
US 2021/0284601 A1    Sep. 16, 2021

Related U.S. Application Data

(60) Provisional application No. 62/692,227, filed on Jun. 29, 2018.

(51) Int. Cl.
| | |
|---|---|
| C07C 247/04 | (2006.01) |
| C07C 247/12 | (2006.01) |
| C07C 247/14 | (2006.01) |
| C07F 7/10 | (2006.01) |
| C07D 347/00 | (2006.01) |
| C07F 7/18 | (2006.01) |

(52) U.S. Cl.
CPC .......... *C07C 247/04* (2013.01); *C07C 247/12* (2013.01); *C07C 247/14* (2013.01); *C07D 347/00* (2013.01); *C07F 7/10* (2013.01); *C07F 7/1896* (2013.01); *C07C 2601/18* (2017.05); *C07C 2602/42* (2017.05)

(58) Field of Classification Search
None
See application file for complete search history.

(56) References Cited

U.S. PATENT DOCUMENTS

| | | | |
|---|---|---|---|
| 6,232,451 B1 | 5/2001 | Claassen | |
| 2012/0077990 A1 | 3/2012 | Zhang | |
| 2015/0057419 A1 | 2/2015 | Asandei | |

FOREIGN PATENT DOCUMENTS

CN    106008403 A    10/2016

OTHER PUBLICATIONS

International Search Report and Written Opinion issued in PCT/US2019/039925, dated Sep. 4, 2019, 10 pages.
Yuan, Ya et al. 'Iron-Catalyzed Direct Diazidation for a Broad Range of Olefins'; Jan. 11, 2016, Angewandte Chemie; vol. 128, Issue 2, pp. 544-548.
PUBCHEM. CID 74955. Mar. 27, 2005, pp. 1-12. Retrieved from the Internet <URL: https://pubchem.ncbi.nlm.nih.gov/compound/74955>.
Agard, Nicholas J., Jennifer A. Prescher, and Carolyn R. Bertozzi. "A strain-promoted [3+2] azide—alkyne cycloaddition for covalent modification of biomolecules in living systems." Journal of the American Chemical Society 126.46 (2004): 15046-15047.
Anami, Yasuaki, et al. "Enzymatic conjugation using branched linkers for constructing homogeneous antibody—drug conjugates with high potency." Organic & biomolecular chemistry 15.26 (2017): 5635-5642.
Andronov, A., Chadwick, Ryan C., et al. "Scalable synthesis of strained cyclooctyne derivatives." Synthesis 46.05 (2014): 669-677.
Arumugam, Selvanathan, et al. "Photo-click chemistry strategies for spatiotemporal control of metal-free ligation, labeling, and surface derivatization." Pure and Applied Chemistry 85.7 (2013): 1499-1513.
Baruah, Mukulesh, and Mikael Bols. "An Azido-Hanessian Reaction." Synlett 2002.07 (2002): 1111-1112.
Baskin, Jeremy M., et al. "Copper-free click chemistry for dynamic in vivo imaging." Proceedings of the National Academy of Sciences 104.43 (2007): 16793-16797.
Bates, Roderick W., and Mark R. Dewey. "A formal synthesis of swainsonine by gold-catalyzed allene cyclization." Organic letters 11.16 (2009): 3706-3708.
Bayramoglu, Gulay, et al. "Trypsin immobilized on magnetic beads via click chemistry: fast proteolysis of proteins in a microbioreactor for MALDI-ToF-MS peptide analysis." Industrial & Engineering Chemistry Research 53.12 (2014): 4554-4564.
Besanceney-Webler, Christen, et al. "Raising the efficacy of bioorthogonal click reactions for bioconjugation: a comparative study." Angewandte Chemie international edition 50.35 (2011): 8051-8056.
Besanceney-Webler, Christen, et al. "Metabolic labeling of fucosylated glycoproteins in Bacteroidales species." Bioorganic & medicinal chemistry letters 21.17 (2011): 4989-4992.
Bock, Victoria D., Henk Hiemstra, and Jan H. Van Maarseveen. "CuI-catalyzed alkyne-azide "click" cycloadditions from a mechanistic and synthetic perspective." European Journal of Organic Chemistry 2006.1 (2006): 51-68.
Bogen, S., et al. "Hepatitis C virus NS3-4A serine protease inhibitors: SAR of new P1 derivatives of SCH 503034." Bioorganic & medicinal chemistry letters 18.14 (2008): 4219-4223.
Boultadakis-Arapinis, Mélissa, et al. "Carbene-Mediated Functionalization of the Anomeric C-H Bond of Carbohydrates: Scope and Limitations." Chemistry—A European Journal 19.19 (2013): 6052-6066.
Bräse, Stefan, et al. "Organic azides: an exploding diversity of a unique class of compounds." Angewandte Chemie International Edition 44.33 (2005): 5188-5240.

(Continued)

*Primary Examiner* — Joseph R Kosack
(74) *Attorney, Agent, or Firm* — Meunier Carlin & Curfman LLC

(57) ABSTRACT

The present invention provides processes for the synthesis of organic azides, intermediates for the production thereof, and compositions related thereto.

13 Claims, No Drawings

(56) References Cited

OTHER PUBLICATIONS

Breton, Gary W., Kimberlee A. Daus, and Paul J. Kropp. "Surface-mediated reactions. 2. Addition of hydrazoic acid to alkenes." The Journal of Organic Chemistry 57.24 (1992): 6646-6649.
Budisa, Nediljko. "Prolegomena to future experimental efforts on genetic code engineering by expanding its amino acid repertoire." Angewandte Chemie International Edition 43.47 (2004): 6426-6463.
Caboni, Pierluigi, et al. "Nematicidal activity of mint aqueous extracts against the root-knot nematode Meloidogyne incognita." Journal of agricultural and food chemistry 61.41 (2013): 9784-9788.
Chan, Anna On-Yee, et al. "Modification of N-terminal α-amino groups of peptides and proteins using ketenes." Journal of the American Chemical Society 134.5 (2012): 2589-2598.
Charron, Guillaume, et al. "Alkynyl-farnesol reporters for detection of protein S-prenylation in cells." Molecular bioSystems 7.1 (2011): 67-73.
Cossy, Janine, Samir Bouzbouz, and Jean Claude Caille. "Enantioselective allyltitanations. Synthesis of optically active 1, 2-diol units: useful intermediates for the preparation of biologically active compounds." Tetrahedron: Asymmetry 10.20 (1999): 3859-3862.
Coutrot, Frédéric, and Eric Busseron. "Controlling the Chair Conformation of a Mannopyranose in a Large-Amplitude [2] Rotaxane Molecular Machine." Chemistry—A European Journal 15.21 (2009): 5186-5190.
Das, Samir, et al. "A general synthetic approach for designing epitope targeted macrocyclic peptide ligands." Angewandte Chemie International Edition 54.45 (2015): 13219-13224.
DeGraw, Amanda J., et al. "Evaluation of alkyne-modified isoprenoids as chemical reporters of protein prenylation." Chemical biology & drug design 76.6 (2010): 460-471.
Dehnert, Karen W., et al. "Metabolic labeling of fucosylated glycans in developing zebrafish." ACS chemical biology 6.6 (2011): 547-552.
Dequirez, Geoffroy, Valérie Pons, and Philippe Dauban. "Nitrene chemistry in organic synthesis: still in its infancy?" Angewandte Chemie International Edition 51.30 (2012): 7384-7395.
Dommerholt, Jan, Floris PJT Rutjes, and Floris L. van Delft. "Strain-promoted 1, 3-dipolar cycloaddition of cycloalkynes and organic azides." Cycloadditions in Bioorthogonal Chemistry (2016): 57-76.
Doyle, Abigail G., and Eric N. Jacobsen. "Small-molecule H-bond donors in asymmetric catalysis." Chemical Reviews 107.12 (2007): 5713-5743.
Empting, Martin, et al. ""Triazole Bridge": Disulfide-Bond Replacement by Ruthenium-Catalyzed Formation of 1, 5-Disubstituted 1, 2, 3-Triazoles." Angewandte Chemie International Edition 50.22 (2011): 5207-5211.
Felpin, François-Xavier, and Jacques Lebreton. "A highly stereoselective asymmetric synthesis of (-)-lobeline and (-)-sedamine." The Journal of organic chemistry 67.26 (2002): 9192-9199.
Fontaine, Shaun D., et al. "Long-term stabilization of maleimide-thiol conjugates." Bioconjugate chemistry 26.1 (2015): 145-152.
Gao, Yahui, et al. "Inkjet printing patterns of highly conductive pristine graphene on flexible substrates." Industrial & engineering chemistry research 53.43 (2014): 16777-16784.
Goias, Patricia L., et al. "Catalyst performance in "click" coupling reactions of polymers prepared by ATRP: ligand and metal effects." Macromolecules 39.19 (2006): 6451-6457.
Gololobov, Yuri G., and Leonid F. Kasukhin. "Recent advances in the Staudinger reaction." Tetrahedron 48.8 (1992): 1353-1406.
Gong, Haibiao, et al. "Simple method to prepare oligonucleotide-conjugated antibodies and its application in multiplex protein detection in single cells." Bioconjugate chemistry 27.1 (2016): 217-225.
Gori, Alessandro, et al. "Screening complex biological samples with peptide microarrays: the favorable impact of probe orientation via chemoselective immobilization strategies on clickable polymeric coatings." Bioconjugate chemistry 27.11 (2016): 2669-2677.

Goswami, Lalit N., et al. "Efficient synthesis of diverse heterobifunctionalized clickable oligo (ethylene glycol) linkers: potential applications in bioconjugation and targeted drug delivery." Organic & biomolecular chemistry 11.7 (2013): 1116-1126.
Hart, Courtenay, et al. "Metabolic labeling and click chemistry detection of glycoprotein markers of mesenchymal stem cell differentiation." Mesenchymal Stem Cell Assays and Applications. Humana Press, 2011. 459-484.
Hartwell, Brittany L., et al. "Multivalent Soluble Antigen Arrays Exhibit High Avidity Binding and Modulation of B Cell Receptor-Mediated Signaling to Drive Efficacy against Experimental Autoimmune Encephalomyelitis." Biomacromolecules 18.6 (2017): 1893-1907.
Hassner, Alfred, Richard Fibiger, and Donald Andisik. "Synthetic methods. 19. Lewis acid catalyzed conversion of alkenes and alcohols to azides." The Journal of Organic Chemistry 49.22 (1984): 4237-4244.
Hays, David S., and Gregory C. Fu. "Development of Bu3SnH-catalyzed processes: efficient reduction of azides to amines." The Journal of Organic Chemistry 63.9 (1998): 2796-2797.
Hein, Christopher D., Xin-Ming Liu, and Dong Wang. "Click chemistry, a powerful tool for pharmaceutical sciences." Pharmaceutical research 25.10 (2008): 2216-2230.
Himo, Fahmi, et al. "Copper (I)-catalyzed synthesis of azoles. DFT study predicts unprecedented reactivity and intermediates." Journal of the American Chemical Society 127.1 (2005): 210-216.
Hong, V. et al. Analysis and Optimization of Copper-Catalyzed Azide—Alkyne Cycloaddition for Bioconjugation**, Angewandte Chemie International Edition 2009, 48, 9879-9883.
Huang, Dayun, and Guobing Yan. "Recent advances in reactions of azides." Advanced Synthesis & Catalysis 359.10 (2017): 1600-1619.
Jao, Cindy Y., et al. "Metabolic labeling and direct imaging of choline phospholipids in vivo." Proceedings of the National Academy of Sciences 106.36 (2009): 15332-15337.
Johnson, Jeremiah A., et al. "Residue-specific incorporation of non-canonical amino acids into proteins: recent developments and applications." Current opinion in chemical biology 14.6 (2010): 774-780.
Kapat, Ajoy, et al. "A radical procedure for the anti-Markovnikov hydroazidation of alkenes." Journal of the American Chemical Society 133.35 (2011): 13890-13893.
Khiar, Noureddine, et al. "Enantiopure sulforaphane analogues with various substituents at the sulfinyl sulfur: Asymmetric synthesis and biological activities." The Journal of organic chemistry 74.16 (2009): 6002-6009.
Kho, Yoonjung, et al. "A tagging-via-substrate technology for detection and proteomics of farnesylated proteins." Proceedings of the National Academy of Sciences 101.34 (2004): 12479-12484.
Kim, Dong Wook. "Bioorthogonal click chemistry for fluorine-18 labeling protocols under physiologically friendly reaction condition." Journal of Fluorine Chemistry 174 (2015): 142-147.
Kim, Sanggil, et al. "Direct protein—protein conjugation by genetically introducing bioorthogonal functional groups into proteins." Bioorganic & medicinal chemistry 24.22 (2016): 5816-5822.
Kirshenbaum, Kent, Isaac S. Carrico, and David A. Tirrell. "Biosynthesis of proteins incorporating a versatile set of phenylalanine analogues." ChemBioChem 3.2-3 (2002): 235-237.
Krafft, Marie E., et al. "Cobalt carbonyl-mediated carbocyclizations of enynes: Generation of bicyclooctanones or monocyclic alkenes." The Journal of organic chemistry 67.4 (2002): 1233-1246.
Kulkarni, Chethana, et al. "Development of fluorophore-labeled thailanstatin antibody-drug conjugates for cellular trafficking studies." Bioconjugate chemistry 28.4 (2017): 1041-1047.
Laughlin, Scott T., and Carolyn R. Bertozzi. "Imaging the glycome." Proceedings of the National Academy of Sciences 106.1 (2009): 12-17.
Lee, Maximillian TW, et al. "Enabling the controlled assembly of antibody conjugates with a loading of two modules without antibody engineering." Chemical science 8.3 (2017): 2056-2060.
Lee, Ross A., and Dennis S. Donald. "Magtrieve™ an efficient, magnetically retrievable and recyclable oxidant." Tetrahedron letters 38.22 (1997): 3857-3860.

(56) References Cited

OTHER PUBLICATIONS

Leggans, Erick K., et al. "Iron (III)/NaBH4-mediated additions to unactivated alkenes: synthesis of novel 20'-vinblastine analogues." Organic letters 14.6 (2012): 1428-1431.

Li, Xiuru, Tao Fang, and Geert-Jan Boons. "Preparation of Well-Defined Antibody-Drug Conjugates through Glycan Remodeling and Strain-Promoted Azide—Alkyne Cycloadditions." Angewandte Chemie 126.28 (2014): 7307-7310.

Lim, Sung In, et al. "Site-specific fatty acid-conjugation to prolong protein half-life in vivo." Journal of controlled release 170.2 (2013): 219-225.

Lonca, Geoffroy Hervé, et al. "Anti-Markovnikov Hydrofunctionalization of Alkenes: Use of a Benzyl Group as a Traceless Redox-Active Hydrogen Donor." Angewandte Chemie International Edition 56.38 (2017): 11440-11444.

Malkov, Andrei V., et al. "Palladium-Catalyzed Alkoxycarbonylation of Terminal Alkenes To Produce α, γ-Unsaturated Esters: The Key Role of Acetonitrile as a Ligand." Chemistry—A European Journal 20.16 (2014): 4542-4547.

Mancuso, Lena, et al. "Preparation of thermocleavable conjugates based on ansamitocin and superparamagnetic nanostructured particles by a chemobiosynthetic approach." Chemistry—A European Journal 20.52 (2014): 17541-17551.

Manova, Radostina, Teris A. van Beek, and Han Zuilhof. "Surface Functionalization by Strain-Promoted Alkyne—Azide Click Reactions." Angewandte Chemie International Edition 50.24 (2011): 5428-5430.

Marks, Isaac S., et al. "Strain-promoted "click" chemistry for terminal labeling of DNA." Bioconjugate chemistry 22.7 (2011): 1259-1263.

Martin, Brent R., and Benjamin F. Cravatt. "Large-scale profiling of protein palmitoylation in mammalian cells." Nature methods 6.2 (2009): 135-138.

Martin, Brent R., et al. "Global profiling of dynamic protein palmitoylation." Nature methods 9.1 (2012): 84-89.

Maruyama, Kazuhiro, Atsuhiro Osuka, and Katsuhiko Nakagawa. "Photochemistry of Epoxynaphthoquinones. 8. Endo-Stereoselective Photocycloaddition of 2, 3-Epoxy-2, 3-dihydro-2, 3-dimethyl-1, 4-naphthoquinone to Olefins Containing Amide Group." Bulletin of the Chemical Society of Japan 60.3 (1987): 1021-1026.

Maza, Johnathan C., et al. "Synthesis and incorporation of unnatural amino acids to probe and optimize protein bioconjugations." Bioconjugate chemistry 26.9 (2015): 1884-1889.

Meyer, Daniel, and Philippe Renaud. "Enantioselective Hydroazidation of Trisubstituted Non-Activated Alkenes." Angewandte Chemie International Edition 56.36 (2017): 10858-10861.

Molnar, I. G., & Gilmour, R. (2016). Catalytic Difluorination of Olefins. Journal of the American Chemical Society, 138(15), 5004-5007. doi:10.1021/jacs.6b01183.

Mulder, Gwenn E., John AW Kruijtzer, and Rob MJ Liskamp. "A combinatorial approach toward smart libraries of discontinuous epitopes of HIV gp120 on a TAC synthetic scaffold." Chemical Communications 48.80 (2012): 10007-10009.

Murakami, Kei, Hideki Yorimitsu, and Koichiro Oshima. "Zinc-catalyzed nucleophilic substitution reaction of chlorosilanes with organomagnesium Yeagents." The Journal of organic chemistry 74.3 (2009): 1415-1417.

Neef, Anne B., Florent Samain, and Nathan W. Luedtke. "Metabolic labeling of DNA by purine analogues in vivo." ChemBioChem 13.12 (2012): 1750.

Ngai, Mun H., et al. "Click-based synthesis and proteomic profiling of lipstatin analogues." Chemical communications 46.44 (2010): 8335-8337.

Northrop, Brian H., Stephen H. Frayne, and Umesh Choudhary. "Thiol-maleimide "click" chemistry: evaluating the influence of solvent, initiator, and thiol on the reaction mechanism, kinetics, and selectivity." Polymer Chemistry 6.18 (2015): 3415-3430.

Nuhn, Lutz, et al. "Water-soluble polymers coupled with glycopeptide antigens and T-cell epitopes as potential antitumor vaccines." Angewandte Chemie International Edition 52.40 (2013): 10652-10656.

Palsuledesai, Charuta C., et al. "Metabolic labeling with an alkyne-modified isoprenoid analog facilitates imaging and quantification of the prenylome in cells." ACS chemical biology 11.10 (2016): 2820-2828.

Paquette, Leo A., William P. Melega, and James D. Kramer. "A method for the benzoannulation of ketones." Tetrahedron Letters 17.45 (1976): 4033-4036.

Puthenveetil, Sujiet, et al. "Development of solid-phase site-specific conjugation and its application toward generation of dual labeled antibody and fab drug conjugates." Bioconjugate chemistry 27.4 (2016): 1030-1039.

Rangan, Kavita J., et al. "Rapid visualization and large-scale profiling of bacterial lipoproteins with chemical reporters." Journal of the American Chemical Society 132.31 (2010): 10628-10629.

Ren, R. et al. "Manganese-Catalyzed Oxidative Azidation of Cyclobutanols: Regiospecific Synthesis of Alkyl Azides by C-C Bond Cleavage", Angewandte Chemie International Edition 2015, 54, 12692-12696.

Rodionov, Valentin O., Valery V. Fokin, and M. G. Finn. "Mechanism of the Tigand-free CuI-catalyzed azide-alkyne cycloaddition reaction." Angewandte Chemie 117.15 (2005): 2250-2255.

Rostovtsev, Vsevolod V., et al. "A stepwise huisgen cycloaddition process: copper (I)-catalyzed regioselective "ligation" of azides and terminal alkynes." Angewandte Chemie 114.14 (2002): 2708-2711.

Sawant, Anupam A., et al. "A versatile toolbox for posttranscriptional chemical Tabeling and imaging of RNA." Nucleic acids research 44.2 (2016): e16-e16.

Scriven, Eric FV, and Kenneth Turnbull. "Azides: their preparation and synthetic uses." Chemical Reviews 88.2 (1988): 297-368.

Shen, Shou-Jie, et al. "Iron-catalyzed direct olefin diazidation via peroxyester activation promoted by nitrogen-based ligands." ACS catalysis 8.5 (2018): 4473-4482.

Sola, Laura, et al. "Synthesis of clickable coating polymers by postpolymerization modification: applications in microarray technology." Langmuir 32.40 (2016): 10284-10295.

Swiderska, K. W., et al. "Site-specific conjugation of fibroblast growth factor 2 (FGF2) based on incorporation of alkyne-reactive unnatural amino acid." Bioorganic & medicinal chemistry 25.14 (2017): 3685-3693.

Taskova, Maria, et al. "Antisense oligonucleotides internally labeled with peptides show improved target recognition and stability to enzymatic degradation." Bioconjugate chemistry 28.3 (2017): 768-774.

Tornøe, Christian W., Caspar Christensen, and Morten Meldal. "Peptidotriazoles on solid phase:[1, 2, 3]-triazoles by regiospecific copper (I)-catalyzed 1, 3-dipolar cycloadditions of terminal alkynes to azides." The Journal of organic chemistry 67.9 (2002): 3057-3064.

Torres, Oscar, et al. "Peptide Tertiary Structure Nucleation by Side-Chain Crosslinking with Metal Complexation and Double "Click" Cycloaddition." ChemBioChem 9.11 (2008): 1701-1705.

Van Geel, Remon, et al. "Chemoenzymatic conjugation of toxic payloads to the globally conserved N-glycan of native mAbs provides homogeneous and highly efficacious antibody-drug conjugates." Bioconjugate chemistry 26.11 (2015): 2233-2242.

Van Maarseveen, Jan H., W. Seth Horne, and M. Reza Ghadiri. "Efficient route to C2 symmetric heterocyclic backbone modified cyclic peptides." Organic letters 7.20 (2005): 4503-4506.

VanBrunt, Michael P., et al. "Genetically encoded azide containing amino acid in mammalian cells enables site-specific antibody—drug conjugates using click cycloaddition chemistry." Bioconjugate chemistry 26.11 (2015): 2249-2260.

Wang, Hua, et al. "Selective in vivo metabolic cell-labeling-mediated cancer targeting." Nature chemical biology 13.4 (2017): 415-424.

Waser, Jérôme, et al. "Hydrazines and azides via the metal-catalyzed hydrohydrazination and hydroazidation of olefins." Journal of the American Chemical Society 128.35 (2006): 11693-11712.

(56) References Cited

OTHER PUBLICATIONS

Waser, Jérôme, Hisanori Nambu, and Erick M. Carreira. "Cobalt-catalyzed hydroazidation of olefins: convenient access to alkyl azides." Journal of the American Chemical Society 127.23 (2005): 8294-8295.

Wilson, John P., et al. "Proteomic analysis of fatty-acylated proteins in mammalian cells with chemical reporters reveals S-acylation of histone H3 variants." Molecular & Cellular Proteomics 10.3 (2011): M110-001198.

Winz, Marie-Luise, et al. "Nucleotidyl transferase assisted DNA labeling with different click chemistries." Nucleic acids research 43.17 (2015): e110-e110.

Yang, Yang, et al. "Biosynthetically inspired divergent approach to monoterpene indole alkaloids: total synthesis of mersicarpine, leuconodines B and D, Teuconoxine, melodinine E, leuconolam, and rhazinilam." Organic letters 16.23 (2014): 6216-6219.

Yasui, Kengo, et al. "Unsymmetrical ketone synthesis via a three-component connection reaction of organozincs, allylating agents, and carbon monoxide." The Journal of Organic Chemistry 60.5 (1995): 1365-1380.

Yoon, Hwa In, et al. "Bioorthogonal copper free click chemistry for labeling and tracking of chondrocytes in vivo." Bioconjugate chemistry 27.4 (2016): 927-936.

Yount, Jacob S., et al. "Palmitoylome profiling reveals S-palmitoylation-dependent antiviral activity of IFITM3." Nature chemical biology 6.8 (2010): 610-614.

Yuan, Yong-An, et al. "Iron-catalyzed direct diazidation for a broad range of olefins." Angewandte Chemie Jan. 11, 2016; 55(2): 534-538.

Zaro, Balyn W., et al. "Chemical reporters for fluorescent detection and identification of O-GlcNAc-modified proteins reveal glycosylation of the ubiquitin Tigase NEDD4-1." Proceedings of the National Academy of Sciences 108.20 (2011): 8146-8151.

Zeglis, Brian M., et al. "Enzyme-mediated methodology for the site-specific radiolabeling of antibodies based on catalyst-free click chemistry." Bioconjugate chemistry 24.6 (2013): 1057-1067.

Zhang, Chengwei, et al. "Silver-catalyzed radical phosphonofluorination of unactivated alkenes." Journal of the American Chemical Society 135.38 (2013): 14082-14085.

Zheng, Tianqing, et al. "Tracking N-acetyllactosamine on cell-surface glycans in vivo." Angewandte Chemie 123.18 (2011): 4199-4204.

Zhu, Hai-Tao, et al. "Process safety assessment of the iron-catalyzed direct olefin diazidation for the expedient synthesis of vicinal primary diamines." Organic process research & development 21.12 (2017): 2068-2072.

Zhu, Yuchao, et al. "Silver-catalyzed decarboxylative azidation of aliphatic carboxylic acids." Organic letters 17.19 (2015): 4702-4705.

Zimmerman, Erik S., et al. "Production of site-specific antibody—drug conjugates using optimized non-natural amino acids in a cell-free expression system." Bioconjugate chemistry 25.2 (2014): 351-361.

Zhdankin V V et al: "Preparation and chemistry of stable azidoiodinanes: 1-Azido-3,3-bis(trifluoromethyl)-3-(1 H)-1 ,2-benziodoxol and 1-Azido-1,2-benziodoxol-3-(1 H)-one", Tetrahedron Letters, Elsevier, Amsterdam, NL, vol. 35, No. 52, Dec. 26, 1994, pp. 9677-9680.

Zhou, Huan et al: "Copper-Catalyzed Ligand-Free Diazidation of Olefins with TMSN 3 in CH 3 CN or in H 2 O", Organic Letters, vol. 19, No. 22, Nov. 17, 2017, pp. 6120-6123.

Nielsen et al: "Asymmetric conjugate addition of azide to @a,@b-unsaturated nitro compounds catalyzed by cinchona alkaloids", Tetrahedron, Elsevier Sience Publishers, Amsterdam, NL, vol. 63, No. 26, May 23, 2007, pp. 5849-5854.

Ehrenfreund, Josef et al: "Reaktionen polyvalenter Jodverbindungen IV1) Reaktionen van (Diacetoxyjod)benzol/Trimethylsilylazid mit Olefinen", Justus Liebigs Annalen der Chemie, Mar. 26, 1973, pp. 290-300.

Extended European Search Report issued in corresponding application No. 19826551.4, dated Nov. 24, 2021, 9 pages.

Communication Pursuant to Article 94(3) EPC issued in EP Application No. 19826551.4-1110; dated Dec. 19, 2022; 4 pages.

ENVIRONMENTALLY-FRIENDLY HYDROAZIDATION OF OLEFINS

CROSS-REFERENCE TO RELATED APPLICATIONS

This is a national stage application filed under 35 U.S.C. § 371 of PCT International Application No. PCT/US2019/039925, filed Jun. 28, 2019, entitled "ENVIRONMENTALLY-FRIENDLY HYDROAZIDATION OF OLEFINS," which application claims the benefit of provisional U.S. Application No. 62/692,227 filed Jun. 29, 2018. The entirety of these applications are this application is incorporated by reference.

STATEMENT REGARDING FEDERALLY FUNDED RESEARCH

This invention was made with government support under Grant no. GM110382 awarded by the National Institutes of Health. The government has certain rights in the invention.

FIELD OF THE INVENTION

The present invention provides processes for the synthesis of organic azides, intermediates for the production thereof, and compositions related thereto.

BACKGROUND OF THE INVENTION

Nitrogen atoms are common components of small-molecule pharmaceuticals and other biomaterials. While processes for the introduction of nitrogen into molecules by functional group transformations have been employed for decades, those that proceed by the direct functionalization of inexpensive hydrocarbon starting materials are less common. Processes for hydrocarbon nitrogen functionalization that avoid the use of toxic transition metals are even rarer. Heavy metal contamination must be removed or avoided altogether in the synthesis of compounds that are intended for use in biological systems. Further, many well-established processes for the introduction of nitrogen in molecules are not environmentally friendly due to their use of stoichiometric levels of reagents.

There is a clear need for more efficient, atom-economical, and environmentally-friendly processes for the synthesis of nitrogen-containing molecules.

There is also a need for processes for the synthesis of nitrogen-containing molecules that do not use heavy metals.

SUMMARY OF THE INVENTION

The present invention provides processes for the synthesis of organic azides or azide-functionalized oligomers or polymers by the reaction of an olefin, a silyl azide, and a hydrogen bond donor in the presence of an organic promoter, which is accomplished in an environmentally-friendly and atom-economical manner that does not require the use of metal catalysis. The organic azides provided hereby can be used to create a wide range of nitrogen-containing organic molecules, including those of pharmaceutical and biological interest. The process can also be used to make nitrogen-containing industrial organic compounds.

In particular, the present processes allow for the synthesis of organic azides from cheap olefin feedstocks instead of more expensive pre-functionalized materials that often require multiple transformations and purifications to obtain the desired product. The present process is significantly more atom economical than previous azide synthetic processes that produced stoichiometric levels of byproducts. The processes described herein also allow for the direct synthesis of hydroazidation products without the use of heavy metals, instead using an organic promoter to mediate the transformation. The prior art metal-mediated or catalyzed transformations often require significant additional purification steps to remove metal contaminants from the final products. This is particularly necessary in pharmaceutical and biological applications where metal contamination can often have detrimental toxicity. Additionally, the lack of heavy metals avoids the risk of accidental formation of explosive metal azide byproducts. The present processes are also safer for operators because they avoid the use of stoichiometric quantities of the highly volatile, toxic, and explosive reagent hydrazoic acid, and instead use silyl azide reagents that are commercially available and easier to handle. In addition, the presently disclosed processes are redox neutral, avoiding the use of stoichiometric oxidants, stoichiometric reductants, or the use of energy-intensive electrochemical processes to facilitate the transformation, an improvement over many azidation processes that have been previously reported. The currently disclosed process goes through a free radical-based mechanism to produce the organic azides from simple olefins.

According to the prior art, alkyl azides are typically prepared by nucleophilic displacement of a leaving group, such a halogen or sulfonate, with sodium azide. Hydroazidation reactions involving addition across a double bond have been more rarely reported. Markovnikov addition of hydrazoic acid ($HN_3$) has been reported across a limited subset of strained and reactive olefins, most likely preceding through the intermediacy of stabilized tertiary and benzylic carbocations (see Hassner, A. et al. Journal of Organic Chemistry 1984, 49, 4237; and Breton, G. W. et al. Journal of Organic Chemistry 1992, 57, 6646). Erick Carreira and coworkers have reported a cobalt-catalyzed Markovnikov hydroazidation reaction using electrophilic sulfonyl azides (see Waser, J. et al. Journal of the American Chemical Society 2005, 127, 8294; and Waser, J. et al. Journal of the American Chemical Society 2006, 128, 11693), Dale Boger and coworkers have similarly reported an iron-mediated Markovnikov hydroazidation reaction using sodium azide (see Leggans, E. K. et al. Organic Letters 2012, 14, 1428).

Until now, anti-Markovnikov hydroazidations of unfunctionalized olefins have been comparatively under-developed. Multi-step stoichiometric processes are more common. A four-step hydroboration-oxidation-mesylation-azidation sequence results in a formal anti-Markovnikov hydroazidation of an olefin (e.g., see Yang, Y. et al. Organic Letters 2014, 16, 6216). Phillipe Renaud and coworkers have reported a two-step hydroazidation protocol wherein a stoichiometric amount of an intermediate organoborane is formed via anti-Markovnikov olefin hydroboration, and the organoborane is subsequently reacted with a sulfonyl azide in the presence of a radical initiator to furnish an organic azide in a second step (see Kapat, A. et al. Journal of the American Chemical Society 2011, 133, 13890; and Meyer D. and Renaud, P. Angewandte Chemie International Edition 2017, 56, 10858). Shunsuke Chiba, Fabien Gagosz, and coworkers have described an anti-Markovnikov hydroazidation reaction that requires the presence of benzylic groups within the substrate so that they may be used as hydrogen donors (see Lonca, G. H. et al. Angewandte Chemie International Edition 2017, 56, 11440-11444).

Hao Xu and coworkers have reported on an iron-catalyzed diazidation reaction of olefins that uses a stoichiometric amount of either a benziodoxole or organic peroxide oxidant (see Yuan, Y.-A. of al. Angewandte Chemie International Edition 2016, 55, 534; Zhu, H.-T. et al. Organic Process Research Development 2017, 21, 2068; and Shen, S.-J. et al. ACS Catalysis 2018, 8, 4473). While this reaction scheme advances the art, it still includes the use of metal catalysis.

In the present invention, the azide is typically added in an anti-Markovnikov orientation across the double bond. Thus, this process provides a means to obtain anti-Markovnikov nitrogen-bearing addition products in an environmentally friendly fashion.

In one aspect, a process is provided for the synthesis of an organic azide comprising combining an olefin, a silyl azide, a hydrogen bond donor, and an organic promoter such that an organic azide is formed. In another aspect, a process is provided for the synthesis of an organic azide of Formula III comprising mixing an olefin of Formula I, a silylazide of Formula II, a hydrogen bond donor, and an organic promoter such than an organic azide of III is formed. In another aspect, a process for the synthesis of an organic azide is provided as illustrated in Scheme 1:

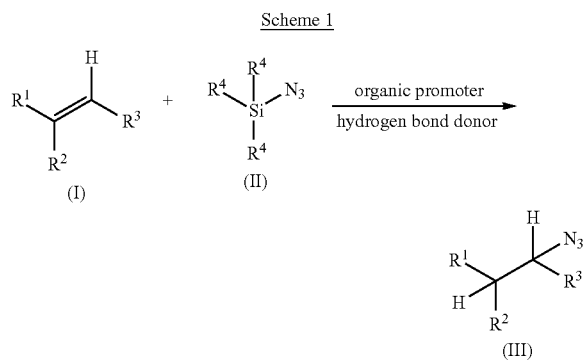

wherein:

$R^1$ and $R^2$ are independently selected from hydrogen, alkyl, cycloalkyl, heteroalkyl, and heterocycloalkyl, wherein each of $R^1$ and $R^2$ that is not hydrogen may be optionally substituted with one or more substituents that do not adversely affect the desired reaction, for example a substituent selected from oxo, halo, cyano, azido, nitro, $R^7$, —$NOR^7$, —$N(R^7)$, —$(C=O)R^7$, —$(C=O)OR^7$, —$(C=O)N(R^7)(R^7)$, —$O(C=O)R^7$, —$N(R^7)(C=O)R^7$, —$O(C=O)N(R^7)(R^7)$, and —$N(R^7)(C=O)OR^7$;

wherein at least one of $R^1$ and $R^2$ is not hydrogen;

$R^3$ is selected from hydrogen, alkyl, cycloalkyl, heteroalkyl, and heterocycloalkyl, wherein $R^3$ other than hydrogen may be optionally substituted with one or more substituents that do not adversely affect the desired reaction, for example a substituent selected from oxo, halo, cyano, azido, nitro, $R^7$, —$OR^7$, —$N(R^7)(R^7)$, —$(C=O)R^7$, —$(C=O)OR^7$, —$(C=O)N(R^7)(R^7)$, —$O(C=O)R^7$, —$N(R^7)(C=O)R^7$, —$O(C=O)N(R^7)(R^7)$, and —$N(,R^7)(C=O)OR^7$; or $R^1$ and $R^2$ or $R^2$ and $R^3$ are taken together with the carbons to which they are attached to form a cycloalkyl ring or an heterocycloalkyl ring, wherein each cycloalkyl or heterocycloalkyl ring can be optionally substituted with one or more substituents that do not adversely affect the desired reaction, for example a substituent selected from oxo, halo, cyano, azido, nitro, $R^7$, —$OR^7$, —$N(R^7)(R^7)$, —$(C=O)R^7$, —$(C=O)OR^7$, —$(C=O)N(R^7)(R^7)$, —$O(C=O)R^7$, —$N(R^7)(C=O)R^7$, —$O(C=O)N(R^7)(R^7)$, and —$N(R^7)(C=O)OR^7$;

$R^4$ is independently selected at each occurrence from alkyl and cycloalkyl;

the organic promoter is selected from:

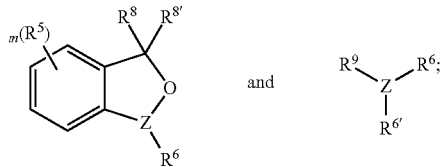

$R^5$ is independently selected from hydrogen, halo, cyano, azido, nitro, $R^7$, —$OR^7$, —$N(R^7)(R^7)$, —$(C=O)R^7$, —$(C=O)OR^7$, —$(C=O)N(R^7)(R^7)$, —$O(C=O)R^7$, —$N(R^7)(C=O)R^7$, —$(C=O)N(R^7)(R^7)$, and —$N(R^7)(C=O)OR^7$;

m is 1, 2, 3, or 4;

Z is 1;

$R^6$ and $R^{6'}$ are independently selected from —$O(C=O)R^7$, —$O(SO_2)(R^7)$, hydroxyl, and azido;

$R^7$ is independently selected at each occurrence from hydrogen, alkyl, aryl, heteroalkyl, heteroaryl, cycloalkyl, heterocycloalkyl, and trialkylsilyl, each of which $R^7$ other than hydrogen may be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy; or two $R^7$ groups may be brought together with the atoms to which they are attached to from a cycloalkyl, heterocycloalkyl, aryl, or heteroaryl ring, each of which ring may be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxy, amino, alkylatmino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy;

$R^8$ and $R^{8'}$ are independently selected from hydrogen, halo, cyano, azido, nitro, $R^7$, —$OR^7$, —$N(R^7)(R^7)$, —$(C=O)R^7$, —$(C=O)OR^7$, —$(C=O)N(R^7)(R^7)$, —$O(C=O)R^7$, —$N(R^7)(C=O)R^7$, —$O(C=O)N(R^7)(R^7)$, and —$N(R^7)(C=O)OR^7$; or $R^8$ and $R^{8'}$ may be brought together with the carbon to which they are attached to form a cycloalkyl or heterocycloalkyl ring, each of which ring may be optionally substituted with one or more substituents that do not adversely affect the desired reaction, for example a substituent selected from oxo, halo, cyano, azido, nitro, $R^7$, —$OR^7$, —$N(R^7)(R^7)$, —$(C=O)R^7$, —$(C=O)OR^7$, —$(C=O)N(R^7)(R^7)$, —$O(C=O)R^7$, —$N(R^7)(C=O)R^7$, —$O(C=O)N(R^7)(R^7)$, and —$N(R^7)(C=O)OR^7$; or $R^8$ and $R^{8'}$ are brought together to form an oxo or imino group; or $R^9$ is aryl or heteroaryl, for example phenyl, pyridyl, pyrazinyl, or quinolinyl, wherein $R^9$ may be optionally substituted with one or more substituents that do not adversely affect the desired reaction, for example a substituent selected from oxo, halo, cyano, azido, nitro, $R^7$, —$OR^7$, —N($R^7$)($R^7$), —(C=O) $R^7$, —(C=O)O$R^7$, —(C=O)N($R^7$)($R^7$), —O(C=O) —N($R^7$)(C=O)$R^7$, —O(C=O)N($R^7$)($R^7$), and —N($R^7$)(C=O)O$R^7$; and the hydrogen bond donor is water and optionally a second hydrogen bond donor selected from formic acid, an alkylcarboxylic acid, a (cycloalkyl)carboxylic acid, a (heteroalkyl)carboxylic acid, a (heterocycloalkyl)carboxylic acid, an arylcarboxylic acid, an (heteroaryl)carboxylic acid, sulfuric acid, an alkylsulfonic acid, a (cycloalkyl)sulfonic acid, a (heteroalkyl)sulfonic acid, a (heterocycloalkyl)sulfonic acid, a arylsulfonic acid, and a (heteroaryl)sulfonic acid, each of which second hydrogen bond donor other than formic acid and sulfuric acid can be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one aspect, the organic azide formed by the process shown in Scheme I produces the anti-Markovnikov addition product or comprises at least about 50% or more of the anti-Markovnikov addition product.

In another aspect, a process is provided for the synthesis of azide-containing oligomers or polymers from simple olefin starting materials. The azide-substituted oligomeric or polymeric compounds that are formed by this process are useful in the synthesis of new materials, such as new polymers for use in medical devices, or in bioconjugation reactions that may lead to new drug delivery methods, for example biologic-polymer-drug conjugates. This oligomerization or polymerization method allows for the preparation of these materials without metal contamination, again allowing ready use in biological systems without concern for toxic contamination.

In another aspect, a process is provided for the synthesis of an azide-containing oligomer or polymer comprising mixing an olefin, a silylazide, a hydrogen bond donor, and an organic promoter, wherein the olefin is substituted with at least one electron withdrawing group, such that an azide-containing oligomer or polymer is formed. In another aspect, a process is provided for the synthesis of an oligomer or polymer of Formula V comprising mixing an olefin of Formula IV, a silyl azide of Formula II, an organic promoter, and a hydrogen bond donor such that an oligomer or polymer of Formula V is formed. In another aspect, a process for the synthesis of an azide-containing oligomer or polymer is provided as illustrated in Scheme 2:

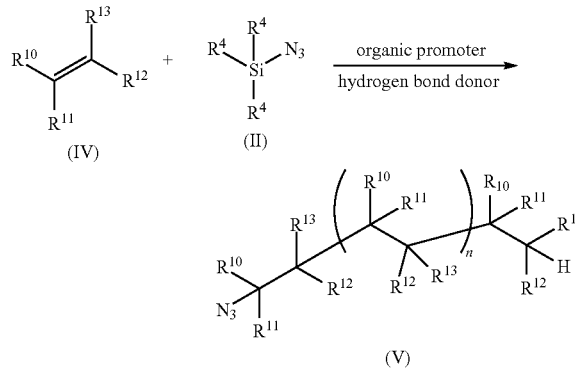

wherein $R^4$, $R^7$, the organic promoter, and the hydrogen bond donor are as defined above;

$R^{10}$, $R^{11}$, and $R^{12}$ are independently selected from hydrogen, halogen, cyano, —(C=O)$R^7$, —(C=O)O$R^7$, —(C=O)N($R^7$)($R^7$), alkyl, cycloalkyl, heteroalkyl, heterocycloalkyl, aryl, or heteroaryl, wherein each of $R^{10}$, $R^{11}$, and $R^{12}$ other than hydrogen, halogen, or cyano may be optionally substituted with one or more substituents that do not adversely affect the desired reaction, for example a substituent selected from oxo, halo, cyano, azido, nitro, $R^7$, —O$R^7$, —N($R^7$)($R^7$), —(C=O) $R^7$, —(C=O)O$R^7$, —(C=O)N($R^7$)($R^7$), —O(C=O)$R^7$, —N($R^7$)(C=O)$R^7$, —O(C=O)N($R^7$)($R^7$), and —N($R^7$)(C=O)O$R^7$; or $R^{10}$ and $R^{11}$ or $R^{11}$ and $R^{12}$ may be brought together with the carbons to which they are attached to form a cycloalkyl ring or a heterocycloalkyl ring, each of which cycloalkyl or heterocycloalkyl ring may be optionally substituted with one or more substituents that do not adversely affect the desired reaction, for example a substituent selected from oxo, halo, cyano, azido, nitro, $R^7$, —O$R^7$, —N($R^7$)($R^7$), —(C=O)$R^7$, —(C=O)O$R^7$, —(C=O)N($R^7$)($R^7$), —(C=O)$R^7$, —N($R^7$)(C=O)$R^7$, —O(C=O)N($R^7$)($R_7$), and —N($R^7$)(C=O)O$R^7$;

or in an alternative embodiment, $R^{10}$ and $R^{11}$ may be brought together with the carbons to which they are attached to form a cycloalkyl ring or a heterocycloalkyl ring, each of which cycloalkyl or heterocycloalkyl ring may be optionally substituted with one or more substituents that do not adversely affect the desired reaction, for example a substituent selected from oxo, halo, cyano, azido, nitro, $R^7$, —O$R^7$, —N($R^7$)($R^7$), —(C=O)$R^7$, —(C=O)O$R^7$, —(C=O)N($R^7$)($R^7$), —O(C=O)$R^7$, —N($R^7$)(C=O)$R^7$, —O(C=O)N($R^7$)($R^7$), and —N($R^7$)(C=O)O$R^7$;

$R^{13}$ is selected from cyano, nitro, —(C=O)$R^{7a}$, —(C=O)O$R^{7a}$, and —(C=O)N($R^{7a}$)($R^{7b}$);

$R^{7a}$ and $R^{7b}$ are independently selected at each occurrence from hydrogen, alkyl, aryl, heteroalkyl, heteroaryl, cycloalkyl, heterocycloalkyl, and trialkylsilyl, each of which $R^{7a}$ and $R^{7b}$ other than hydrogen may be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy; or $R^{7a}$ and $R^{7b}$ may be brought together with the atoms to which they are attached to form a cycloalkyl or heterocycloalkyl ring, each of which ring may be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy; or $R^{10}$ and $R^{7a}$ may be brought together with the atoms to which they are attached to form a cycloalkyl or heterocycloalkyl ring, each of which ring may be optionally substituted with one or more substituents that do not adversely affect the desired reaction, for example a substituent selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy; and n is 1, 2, 3, 4, 5, 6, 7, 8, 9, 10, 11, 12, 13, 14, 15, 16, 17, 18, 19, 20, 21, 22, 23, 24, or 25.

In some aspects, the olefin is a terminal olefin. In other aspects, the olefin is an asymmetric internal olefin. In other aspects, the olefin is a trisubstituted olefin. In some embodiments, for example those represented in Scheme 2, the olefin contains an electron-withdrawing substituent.

In one aspect, the hydrogen bond donor is water. In another aspect, the hydrogen bond donor is water and a second hydrogen bond donor. In one embodiment, the second hydrogen bond donor is trifluoroacetic acid. In some embodiments, the hydrogen bond donor is a chiral hydrogen bond donor.

In another aspect, the process described herein is carried out in an organic solvent, a mixture of water and an organic solvent, or a mixture of two or more organic solvents. Exemplary solvents include acetone, ethyl acetate (EtOAc), dichloromethane ($CH_2Cl_2$), acetonitrile (MeCN), 1,2-dichloroethane (DCE), nitromethane, hexanes, pentane, toluene, benzene, petroleum ether, 2-butanone, chlorobenzene, chloroform ($CHCl_3$), cyclohexane, heptane, o-xylene, m-xylene, p-xylene, and combinations thereof. In on embodiment, the solvent is selected from ethyl acetate (EtOAc), dichloromethane ($Ch_2Cl_2$), or chloroform ($CHCl_3$). In one embodiment, the solvent is ethyl acetate (EtOAc). In one embodiment, the solvent is dichloromethane ($CH_2Cl_2$). In one embodiment, the solvent is chloroform ($CHCl_3$).

In another aspect, a compound used in or formed by the processes described herein can have at least one isotopic substitution. For example, a compound used in or formed by the processes described herein can have at least one deuterium atom. The inclusion of deuterium can affect the rate of a reaction or the stability of the final product, among other things. If the product is a pharmaceutical agent, substitution with deuterium can be used in metabolic profiling. In one non-limiting embodiment, a process is provided for the synthesis of a beta-deuteroalkyl azide of Formula VI as illustrated in Scheme 3:

incorporated. In some embodiments, a mixture of deuterium oxide and water is used instead of pure deuterium oxide in the reaction shown in Scheme 3.

In another non-limiting embodiment, the process is provided for the synthesis of a deuterated azide-containing oligomer or polymer of Formula XI as illustrated in Scheme 4:

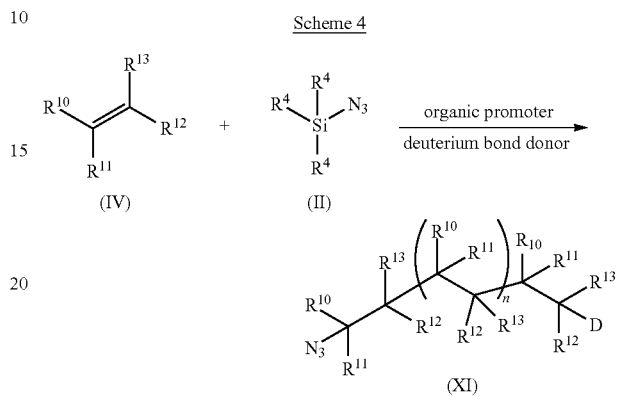

Wherein $R^4$, $R^{10}$, $R^{11}$, $R^{12}$, $R^{13}$, the organic promoter, and the deuterium bond donor are defined as above. In one embodiment, the deuterium is completely incorporated into the product of Formula XI. In another embodiment, the deuterium is partially incorporated into the product of Formula. XI, for example, about 10%, 20%, 30%, 40%, 50%, 60%, 70%, 80%, 90%, 95%, 99%, 99.9%, 99.99%, or 99.999% incorporated. In some embodiments, a mixture of deuterium oxide and water is used instead of pure deuterium oxide in the reaction shown in Scheme 4.

In another aspect, compounds are provided of Formula or Formula VIII:

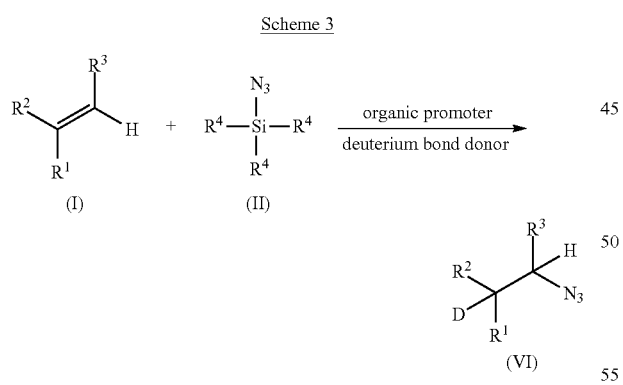

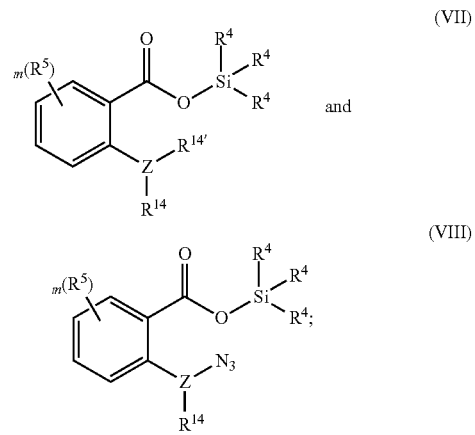

wherein $R^1$, $R^2$, $R^3$, $R^4$, and the organic promoter are defined as above; and the deuterium bond donor consists of deuterium oxide and optionally a deuterated acid selected from trifluoroacetic acid-d, acetic acid-$d_4$, trifluoromethanesulfonic acid-d, methanesulfonic acid-$d_4$, and formic acid-$d_2$. In one embodiment, the deuterium is completely incorporated into the product of Formula VIII. In another embodiment, the deuterium is partially incorporated into the product of Formula VIII, for example, about 10%, 20%, 30%, 40%, 50%, 60%, 70%, 80%, 90%, 95%, 99%, 99.9%, 99.99%, or 99.999% wherein $R^4$, $R^5$, $R^7$, Z, and m are defined as above; and $R^{14}$ and $R^{14'}$ are selected from —O(C=O)$R^7$ and —O($SO_2$)($R^7$).

In another aspect, processes are also provided for the use of the azide-containing product of the inventive process described herein with an alkyne to make a 1,2,3-triazole, for example using an azide-alkyne cycloaddition, in the presence or absence of copper. In one example, a ligand can be added to a biomolecule via the reaction described herein to create an organic azide derivative of an unsaturated starting material, which is then reacted with an alkyne-modified biomolecule. An organic azide formed from an olefin using the processes described herein can be conjugated to an alkyne-containing modified biomolecule using an azide-alkyne cycloaddition reaction.

In another aspect, processes are also provided for the use of the azide-containing product of the inventive process described herein with an alkyne to make a 1,2,3-triazole, for example using an azide-alkyne cycloaddition, in the presence or absence of copper. In one example, a ligand can be added to a biomolecule via the reaction described herein to create an organic azide derivative of an unsaturated starting material, which is then reacted with an alkyne-modified biomolecule. An organic azide formed from an olefin using the processes described herein can be conjugated to an alkyne-containing modified biomolecule using an azide-alkyne cycloaddition reaction.

In one aspect, a process for the conjugation of an organic ligand molecule to a modified biomolecule is provided, wherein the organic ligand molecule is an olefin and the modified biomolecule contains an alkynyl group, is provided comprising:

(a) converting the alkenyl group of the organic ligand molecule to an azidoalkyl group using one of the processes described herein;

(b) optionally purifying the organic ligand molecule; and (c) reacting the azido alkyl group of the organic ligand molecule with the alkynyl group of the modified biomolecule to form a 1,2,3-triazole group that covalently links the organic ligand molecule to the modified biomolecule.

In another aspect, a process for the conjugation of an organic ligand molecule to a modified biomolecule is provided, wherein the organic molecule ligand is an alkene and the modified biomolecule contains an alkynyl group, is provided comprising:

(a) converting the alkenyl group of the organic ligand molecule to an azidoalkyl group using the reaction shown in Scheme 1;

(b) optionally purifying the organic ligand molecule; and (c) reacting the azidoalkyl group of the organic ligand molecule with the alkynyl group of the modified biomolecule to form a 1,2,3-triazole group that covalently links the organic ligand molecule to the modified biomolecule.

In another aspect, a process for the conjugation of an azide-containing oligomer or polymer formed from an organic molecule containing an alkenyl group to a modified biomolecule, wherein the modified biomolecule contains an alkynyl group, is provided comprising:

(a) converting the alkenyl-containing organic molecule to an azide-containing oligomer or polymer using the reaction shown in Scheme 2;

(b) optionally purifying the azide-containing oligomer or polymer; and (c) reacting the azide group of the oligomer or polymer with the alkynyl group of the modified biomolecule to form a 1,2,3-triazole group that covalently links the oligomer or polymer to the modified biomolecule.

The biomolecule can be, in non-limiting embodiments, a protein, peptide, a nucleoside, nucleotide, polynucleotide, such as a polydeoxyribonucleotide or a polyribonucleotide, antibody, hormone, enzyme, structural protein, aptamer, m-RNA, cDNA, cell, including a lymphocyte, signaling agent, a sugar, a monosaccharide or polysaccharide, or a lipid or lipid-like molecule. The organic molecule may be a substrate, an inhibitor, a drug, a mediator of signaling, a fluorescent probe, or any other organic compound that has or can be modified to have an olefin-containing group that may be useful to conjugate with a biomolecule for any purpose. Step (c) in any embodiments of the bioconjugation process can be performed ex vivo, in vitro, or in vivo depending on the desired application.

Non-limiting aspects of the present invention include:

1) A process for the synthesis of an organic azide of Formula III by mixing an olefin of Formula I, a silyl azide of Formula II, an organic promoter, and a hydrogen bond donor until the organic azide product of Formula III is formed;

2) A process for the synthesis of an azide-containing oligomer or polymer of Formula V by mixing an olefin of Formula IV, a silyl azide of Formula II, an organic promoter, and a hydrogen bond donor until the azide-containing oligomer or polymer of Formula V is formed;

3) A process for the synthesis of a beta-deuteroalykl azide of Formula VI by mixing an olefin of Formula I, a silyl azide of Formula an organic promoter, and a deuterium bond donor until the deuterated azide product of Formula. VI is formed;

4) A process for the synthesis of a deuterated azide-containing oligomer or polymer of Formula XI by mixing an olefin of IV, a silyl azide of Formula II, an organic promoter, and a deuterium bond donor until the azide-containing oligomer or polymer of Formula XI is formed;

5) A compound of Formula VII or Formula VIII;

6) A composition comprising:
   a) a silyl azide of Formula II;
   b) an organic promoter of Formula IX or Formula X;
   c) water; and
   d) optionally a second hydrogen bond donor;

7) A composition comprising:
   a) a silyl azide of Formula II;
   b) an organic promoter of Formula IX of Formula X;
   c) an olefin of Formula I;
   d) water; and
   e) optionally a second hydrogen bond donor;

8) A composition comprising:
   a) a silyl azide of Formula II;
   b) an organic promoter of Formula IX or Formula X;
   c) an olefin of Formula IV;
   d) water; and
   e) optionally a second hydrogen bond donor;

9) A process for carrying out the conjugation of an olefin-containing organic compound to a biomolecule comprising reacting the product of the process of Scheme 1 with an alkyne-modified biomolecule to get a 1,2,3-triazole linked conjugate;

10) A process for carrying out the conjugation of an olefin-containing organic compound to a biomolecule comprising reacting the product of the process of Scheme 2 with an alkyne-modified biomolecule to get a 1,2,3-triazole linked conjugate; and 11) A kit comprising:
   a) a first composition containing a silyl azide of Formula III and optionally a first organic solvent;
   b) a second composition comprising a benziodoxole of Formula IV and optionally a second organic solvent; and
   c) a third composition comprising water, optionally a second hydrogen bond donor, and optionally a third organic solvent.

An additional non-limiting aspect of the present invention includes:

12) A kit comprising:
   a) a first composition containing a silyl azide of Formula III and optionally a first organic solvent;

b) a second composition comprising a benziodoxole of Formula IX and optionally a second organic solvent; and c) a third composition comprising water, optionally a second hydrogen bond donor, and optionally a third organic solvent.

Other embodiments will be clear to the skilled worker after reading the detailed disclosure herein, and all variations are intended to be included as part of the scope of the invention.

DETAILED DESCRIPTION OF THE INVENTION

Definitions

Compounds are described using standard nomenclature. Unless defined otherwise, all technical and scientific terms used herein have the same meaning as is commonly understood by one of skill in the art to which the invention belongs.

The compounds in any of the Formulas described herein may be in the form of a racemate, enantiomer, mixture of enantiomers, diastereomer, mixture of diastereomers, tautomer, N-oxide, or other isomer, such as a rotamer, as if each is specifically described unless specifically excluded by context.

The terms "a" and "an" do not denote a limitation of quantity, but rather denote the presence of at least one of the referenced item. The term "or" means "and/or". Recitation of ranges of values merely intend to serve as a shorthand method of referring individually to each separate value falling within the range, unless otherwise indicated herein, and each separate value is incorporated into the specification as if it were individually recited herein. The endpoints of all ranges are included within the range and independently combinable. All processes described herein can be performed in a suitable order unless otherwise indicated herein or otherwise clearly contradicted by context. The use of example, or exemplary language (e.g. "such as"), is intended merely to better illustrate the invention and does not pose a limitation on the scope of the invention unless otherwise claimed.

A dash ("-") that is not between two letters or symbols is used to indicate a point of attachment for a substituent. For example, (C=O)NH$_2$ is attached through the carbon of the keto (C=O) group.

"Alkyl" is a branched or straight chain saturated aliphatic hydrocarbon group. In one non-limiting embodiment, the alkyl group contains from about 1 to about 50 carbon atoms, more generally from 1 to about 36 carbon atoms, from 1 to about 12 carbon atoms, from 1 to about 8 carbon atoms, from 1 to about 6 carbon atoms, or from 1 to about 4 carbon atoms. In certain embodiments, the alkyl is $C_1$-$C_2$, $C_1$-$C_3$, or $C_1$-$C_4$, $C_1$-$C_5$, $C_1$-$C_6$, $C_1$-$C_7$, $C_1$-$C_8$, $C_1$-$C_9$, $C_1$-$C_{10}$. For example, the term $C_1$-$C_6$alkyl as used herein indicates a straight chain or branched alkyl group having from 1, 2, 3, 4, 5, or 6 carbon atoms and is intended to mean that each of these are described as an independent species. For example, the term $C_1$-$C_4$alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentance, 3-methylpentane, 2,2-dimethylbutane, and 2,3-dimethylbutane. In some embodiments, the alkyl group is optionally substituted as defined herein.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-C4alkyl, $C_1$-C3alkyl, $C_1$-C2alkyl, or $C_1$-C1alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "alkyl" is "substituted alkyl"

"Heteroalkyl" refers to an alkyl group as defined herein that contains at least one heteroatom, for example nitrogen, oxygen, sulfur, phosphorous, boron, or silicon, in place of a carbon atom at a position other than at the point of attachment. In some embodiments, "heteroalkyl" also includes groups that contain unsaturation between the heteroatom and a neighboring carbon in such a manner that results in the formation of a stable moiety, for example a —C=N-moiety.

"Cycloalkyl" is a saturated group containing all carbon rings and from 3 to 50 carbon atoms ("$C_3$-$C_{50}$cycloalkyl") and zero heteroatoms in a monocyclic or polycyclic (e.g. bicyclic or tricyclic) non-aromatic ring system. In some embodiments, a cycloalkyl group has 3 to 14 ring atoms ("$C_3$-$C_{14}$cycloalkyl"). In some embodiments, a cycloalkyl group has 3 to 10 ring atoms ("C3-$C_{10}$cycloalkyl"). In some embodiments, a cycloalkyl group has 3 to 9 ring atoms ("$C_3$-C9cycloalkyl"). In some embodiments, a cycloalkyl group has 3 to 8 ring atoms ("$C_3$-$C_8$cycloalkyl"). In some embodiments, a cycloalkyl group has 3 to 7 ring atoms ("$C_3$-$C_7$cycloalkyl"). In some embodiments, a cycloalkyl group has 3 to 6 ring atoms ("$C_3$-$C_6$cycloalkyl"). In some embodiments, a cycloalkyl group has 4 to 6 ring atoms ("$C_4$-$C_6$cycloalkyl"). In some embodiments, a cycloalkyl group has 5 to 6 ring atoms ("$C_5$-$C_6$cycloalkyl"). In some embodiments, a cycloalkyl group has 5 to 10 ring atoms ("$C_5$-$C_{10}$cycloalkyl"). Exemplary $C_3$-$C_{10}$cycloalkyl groups include, without limitation, cyclopropyl ($C_3$), cyclobutyl ($C_4$), cyclopentyl ($C_5$), cyclohexyl ($C_6$), cycloheptyl ($C_7$), cyclooctyl ($C_8$), cyclononyl ($C_9$), cyclodecenyl ($C_{10}$), and the like. In some embodiments, a cycloalkyl group may be a bicyclic alkyl group, for example a spirocyclic alkyl group, a fused bicyclic alkyl group, or a bridged bicyclic alkyl group. In some embodiments, "cycloalkyl" also includes ring systems wherein the cycloalkyl ring, as defined above, is fused with one heterocycloalkyl, aryl, or heteroaryl ring wherein the point of attachment is on the cycloalkyl ring, and in such instances, the number of carbon atoms continue to designate the number of carbons in the cycloalkyl ring system. In some embodiments, the cycloalkyl group is optionally substituted as defined herein.

In one embodiment "cycloalkyl" is a $C_3$-$C_8$cycloalkyl, $C_3$-$C_7$cycloalkyl, $C_3$-$C_7$cycloalkyl, $C_3$-$C_5$cycloalkyl, $C_3$-$C_4$cycloalkyl, $C_4$-$C_8$-cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example

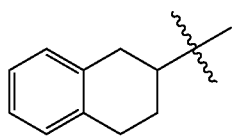 [SMILES: *C1CCc2ccccc2C1]

is an "cycloalkyl" group.

However,

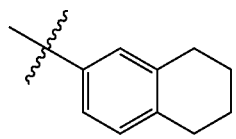 [SMILES: *c1ccc2c(c1)CCCC2]

is an "aryl" group.

In one embodiment "cycloalkyl" is a "substituted cycloalkyl"

The term "heterocycloalkyl" refers to a cycloalkyl group as defined herein that contains at least one heteroatom, for example nitrogen, oxygen, sulfur, phosphorous, boron, or silicon, in place of a carbon atom. Heterocycloalkyl groups comprise monocyclic 3-8 membered rings, as well as 5-16 membered bicyclic ring systems (which can include bridged, fused, and spiro-fused bicyclic ring systems). It does not include rings containing —O—O—, —O—S—, and —S—S- portions. In some embodiments, "heterocycloalkyl" also includes groups that contain unsaturation between the heteroatom and a neighboring carbon in such a manner that results in the formation of a stable moiety, for example a —C=N-moiety. In some embodiments, "heterocycloalkyl" also includes ring systems wherein the cycloalkyl ring, as defined above, is fused with one cycloalkyl, aryl, or heteroaryl ring wherein the point of attachment is on the heterocycloalkyl ring, and in such instances, the number of atoms continue to designate the number of atoms in the heterocycloalkyl ring system. In some embodiments, the cycloalkyl group is optionally substituted as defined herein. In some embodiments, the heterocycloalkyl group is optionally substituted as defined herein. Examples of heterocycloalkyl groups include saturated 3- to 6-membered heteromonocyclic groups containing 1 to 4 nitrogen atoms; saturated 3- to 6-membered heteromonocyclic groups containing 1 to 2 oxygen atoms and 1 to 3 nitrogen atoms; and saturated saturated 3- to 6-membered heteromonocyclic groups containing 1 to 2 sulfur atoms and 1 to 3 nitrogen atoms. Additional examples of heterocycloalkyl groups include aziridinyl, oxiranyl, thiiranyl, azetidinyl, 1,3-diazetidinyl, oxetanyl, thietanyl, pyrrolidinyl, pyrazolidinyl, imidazolidinyl, 2-pyrazolinyl, 2-imidazolinyl, tetrahydrofuranyl, 1,3-dioxolanyl, tetrahydrothienyl, pipetidinyl, piperazinyl, 1,2-oxathiolanyl, 1,3-oxathiolanyl, tetrahydropyranyl, 1,3-dioxanyl, thianyl, 1,3-dithianyl, 1,4-dithianyl, 1,3,5-trithianyl, morpholinyl, thiomorpholinyl, pyrrolizidinyl, indolinyl, isoindolinyl, decahydroisoquinolinyl, decahydroquinolinyl, 1,2,3,4-tetrahydroquinolinyl, quinuclidinyl, 1-azaadamantanyl, 2-azaadamantanyl, oxepanyl, azocanyl, thiocanyl, 1-oxaspiro[4.5]decanyl, 1,6-dioxaspiro[3,4]octanyl, 1-oxaspiro[4.4]nonanyl, 2-oxa-7-azaspiro[3.5]nonanyl, 1,4-dioxa-7-azaspiro[4.4]nonanyl, oxazolidinyl, isoxazolidinyl, thiazolidinyl, isothiazolidinyl, dioxolanyl, dithiolanyl, dihydrobenzofuranyl, and dihydrobenzothienyl.

In one embodiment "heterocycloalkyl" refers to a cyclic ring with one nitrogen and 3, 4, 5, 6, 7, or 8 carbon atoms.

In one embodiment "heterocycloalkyl" refers to a cyclic ring with one nitrogen and one oxygen and 3, 4, 5, 6, 7, or 8 carbon atoms.

In one embodiment "heterocycloalkyl" refers to a cyclic ring with two nitrogens and 3, 4, 5, 6, 7, or 8 carbon atoms.

In one embodiment "heterocycloalkyl" refers to a cyclic ring with one oxygen and 3, 4, 5, 6, 7, or 8 carbon atoms.

In one embodiment "heterocycloalkyl" refers to a cyclic ring with one sulfur and 3, 4, 5, 6, 7, or 8 carbon atoms.

Non-limiting examples of "heterocycloalkyl" include aziridine, oxirane, thiirane, azetidine, 1,3-diazetidine, oxetane, and thietane.

Additional non-limiting examples of "heterocycloalkyl" include pyrrolidine, 3-pyrroline, 2-pyrroline, pyrazolidine, and imidazollidine.

Additional non-limiting examples of "heterocycloalkyl" include tetrahydrofuran, 1,3-dioxolane, tetrahydrothiophene, 1,2-oxathiolane, and 1,3-oxathiolane.

Additional non-limiting examples of "heterocyclalkyl" include piperidine, piperazine, tetrahydropyran, 1,4-dioxane, thiane, 1,3-dithiane, 1,4-dithiane, morpholine, and thiomorpholine.

Additional non-limiting examples of "heterocyoalkyl" include indoline, tetrahydroquinoline, tetrahydroisoquinoline, and dihydrobenzofuran wherein the point of attachment for each group is on the heterocyclic ring.

For example,

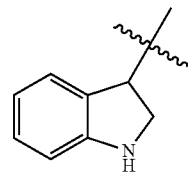 [SMILES: *C1CNc2ccccc21]

is a "heterocycloalkyl" group.

However,

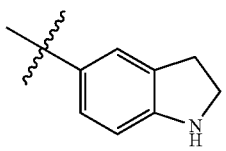 [SMILES: *c1ccc2c(c1)CCN2]

is an "aryl" group.

Non-limiting examples of "heterocycloalkyl" also include:

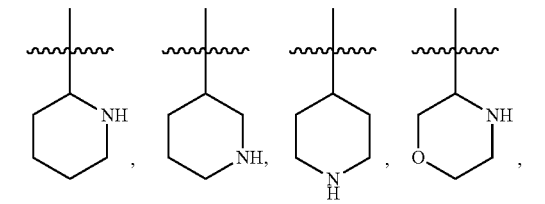

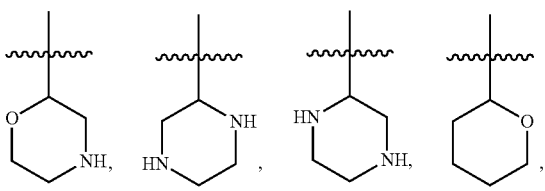

Additional non-limiting examples of "heterocycloalkyl" include:

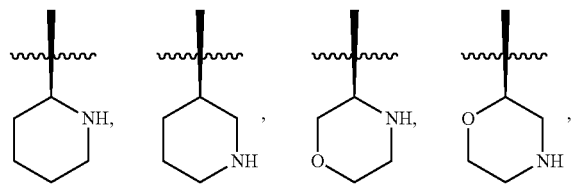

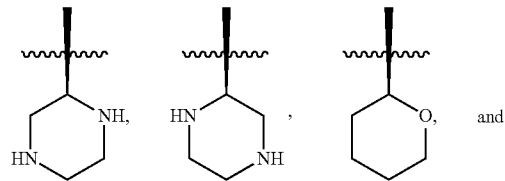

Additional non-limiting examples of "heterocycloalkyl" include:

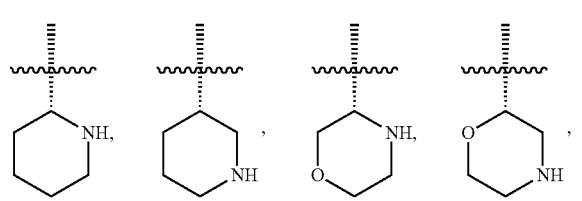

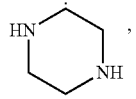
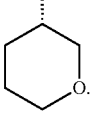
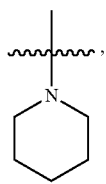 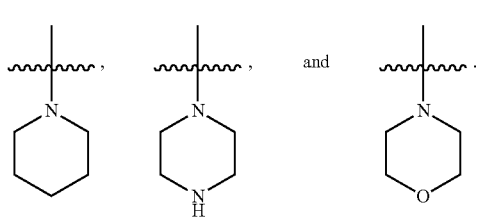 [SMILES: *N1CCCCC1 ; *N1CCNCC1 ; *N1CCOCC1] 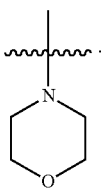

Non-limiting examples of "heterocycloalkyl" also include:

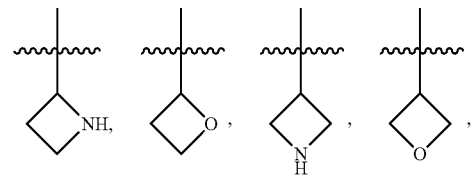

Non-limiting examples of "heterocycloalkyl" also include:

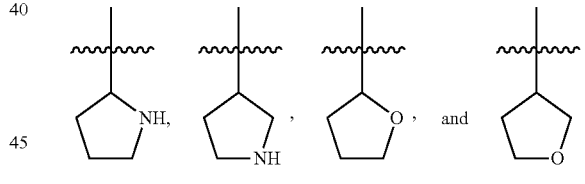

Additional non-limiting examples of "heterocycloalkyl" include:

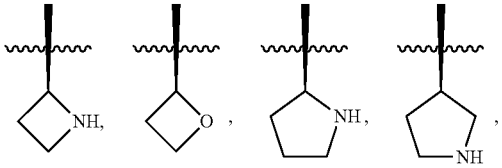

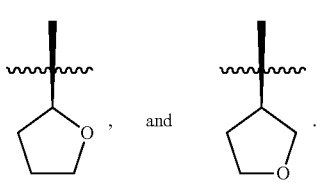

Additional non-limiting examples of "heterocycloalkyl" include:

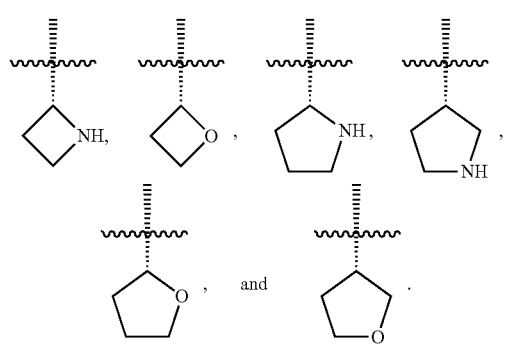

In one embodiment "heterocycloalkyl" is "substituted heterocycloalkyl".

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic system ("$C_6$-$C_{14}$aryl"). In some embodiments, an aryl group has 6 ring carbon atoms ("$C_6$aryl"; e.g., phenyl). In some embodiments, an aryl goup has 10 ring carbon atoms ("$C_{10}$aryl"; e.g., naphthyl such as 1-naphthyl and 2-naphthyl). In some embodiments, an aryl group has 14 ring carbon atoms ("$C_{14}$aryl"; e.g., anthracyl). "Aryl" also includes ring systems wherein the aryl ring, as defined above, is fused with one or more cycloalkyl or heterocycloalkyl groups wherein the point of attachment is on the aryl ring, and in such instances, the number of carbon atoms continue to designate the number of carbon atoms in the aryl ring system. The one or more fused cycloalkyl or heterocycloalkyl groups can be 4 to 7 or 5 to 7-membered cycloalkyl or heterocycloalkyl groups that optionally contain 1, 2, or 3 heteroatoms independently selected from nitrogen, oxygen, phosphorous, sulfur, silicon, and boron. In one non-limiting embodiment, aryl groups are pendant. An example of a pendant ring is a phenyl group substituted with a phenyl group. In some embodiments, the aryl group is optionally substituted as defined herein.

In one embodiment "aryl" is a 6 carbon aromatic group (phenyl).

In one embodiment "aryl" is a 10 carbon aromatic group (napthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

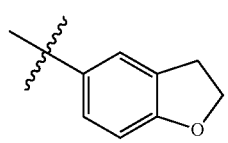 [SMILES: *c1ccc2c(c1)CCO2]

is an "aryl" group.

However,

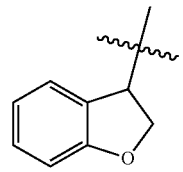 [SMILES: *C1COc2ccccc21]

is a "heterocycle" group.

In one embodiment "aryl" is a 6 carbon aromatic group fused to a cycloalkyl wherein the point of attachment is the aryl ring, Non-limiting examples of "aryl" include dihydroindene and tetrahydronaphthalene wherein the point of attachment for each group is on the aromatic ring.

For example

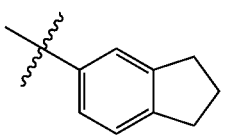 [SMILES: *c1ccc2c(c1)CCC2]

is an "aryl" group.

However,

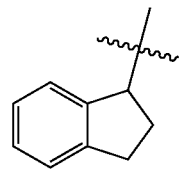 [SMILES: *C1CCc2ccccc21]

is a "cycloalkyl" group.

In one embodiment "aryl" is "substituted aryl".

The term "heteroaryl" denotes aryl ring systems that contain one or more heteroatoms selected from O, N, and S, wherein the ring nitrogen and sulfur atom(s) are optionally oxidized, and nitrogen atom(s) are optionally quaternized. Examples include, but are not limited to: unsaturated 5- to 6-membered heterotnonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, and triazolyl [e.g., 4H-1,2,4-triazolyl, 1H-1,2,3-triazolyl, and 2H-1,2,3-triazolyl]; unsaturated 5-to 6-membered heteromonocyclic groups containing an oxygen group, for example, pyranyl, 2-furyl, 3-furyl, etc.; unsaturated 5- to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazalolyl, isoxazolyl, and oxadiazolyl [e.g., 1,2,4-oxadiazolyl, 1,3,4-oxadiazolyl, and 1,2,5-oxadiazolyl]; and unsaturated 5- to 6-membered heteromonocyclic groups containing 1 to 2 sulfur atoms and 1 to 3 nitrogen atoms, for example, thiazolyl and thiadiazolyl [e.g., 1,3,4-thiadiazolyl and 1,2,5-thiadiazolyl]. "Heteroaryl" also refers to polycyclic aromatic ring systems containing heteroatoms within the ring, for example, 1,4-dihydropyrollo[3,2-b]pyrrolyl, 1,6-dihydropyrrolo[2,3-b]pyrrolyl, 6H-furo[2,3-b]pyrrolyl, 4H-furo[3,2-b]pyrrolyl, 4H-thieno[3,2-b]pyrrolyl, 6H-thieno[2,3-b]pyrrolyl, indolyl, isoindolyl, indolizinyl, indazolyl, benzimidazolyl, 7-azaindolyl, 6-azaindolyl, 5-azaindolyl, 4-azaindolyl, 7-azaindazolyl, pyrazole[1,5-a]

pyrimidinyl, purinyl, benzofuryl, isobenzofuryl, benzo[c]thienyl, benzo[b]thienyl, 1,2-benzisoxazolyl, 2,1-benzisoxazolyl, 2,1-benzisothiazolyl, benzoxazolyl, benzthiasolyl, benzo[c][1,2,5]thiadiazol, quinolinyl, isoquinolinyl, 4H-quinolizinyl, quinoxalinyl, phthalazinyl, quinazolinyl, cinnolinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, carbazolyl, dibenzofuryl, acridinyl, phenazinyl, phenoxazinyl, phenothiazinyl, and phenoxathiin:$_s$71. Additional examples of heteroaryl groups include azepinyl, 1,2-diazepinyi, 1,3-diazepinyl, 1,4-diazepinyl, thiepinyl, 1,4-thiazepinyl, and azocinyl. "Heteroaryl" also includes ring systems wherein the heteroaryl ring, as defined above, is fused with one or more cycloalkyl or heterocycloalkyl groups wherein the point of attachment is on the heteroaryl ring, and in such instances, the number of atoms continue to designate the number of atoms in the heteroaryl ring system. The one or more fused cycloalkyl or heterocycloalkyl groups can be 4 to 7 or 5 to 7-membered cycloalkyl or heterocycloalkyl groups that optionally contain 1, 2, or 3 heteroatoms independently selected from nitrogen, oxygen, phosphorous, sulfur, silicon, and boron. In one non-limiting embodiment, aryl groups are pendant.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

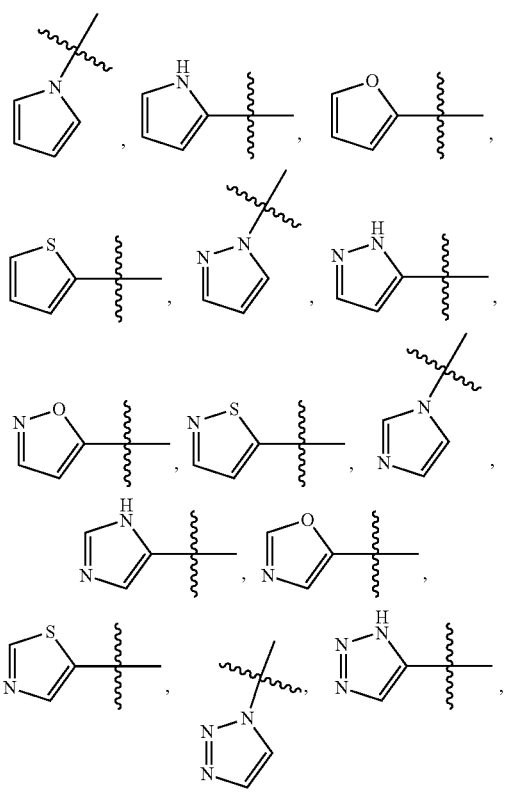

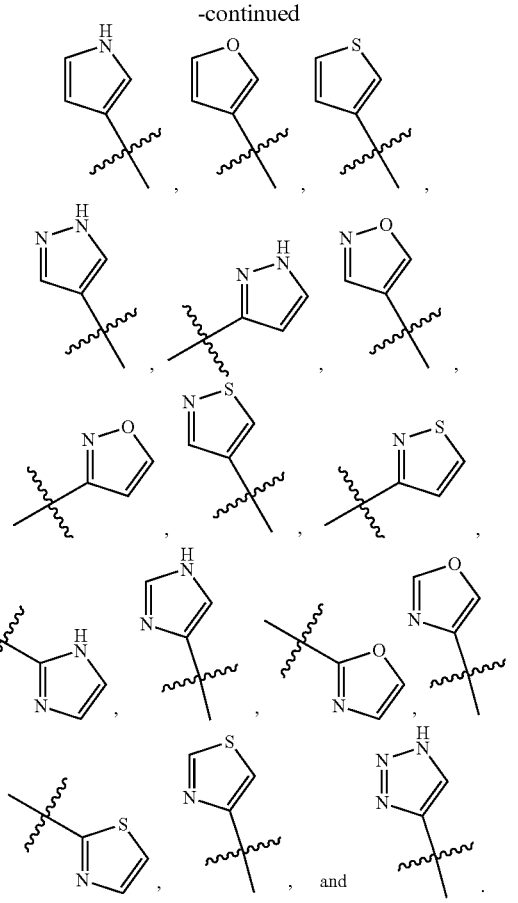

In one embodiment "heteroaryl" is a 6 membered aromatic group containing 1, 2, or 3 nitrogen atoms i.e, pyridinyl pyridazinyl, triazinyl, pyrimidinyl, and pyrazinyl).

Non-limiting examples of 6 membered "heteroaryl" groups with 1 or 2 nitrogen atoms include:

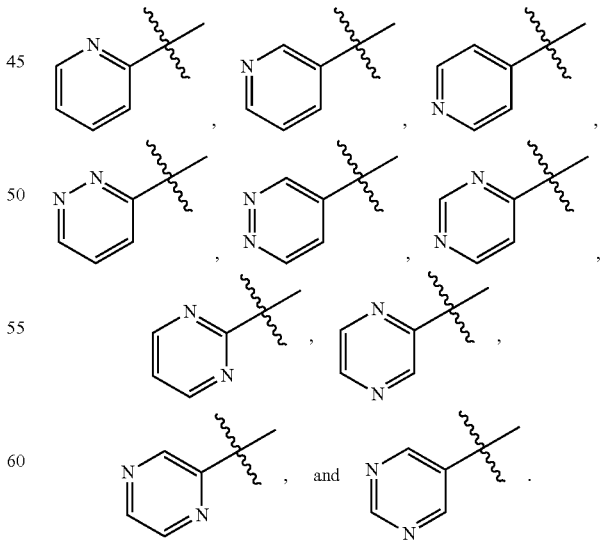

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

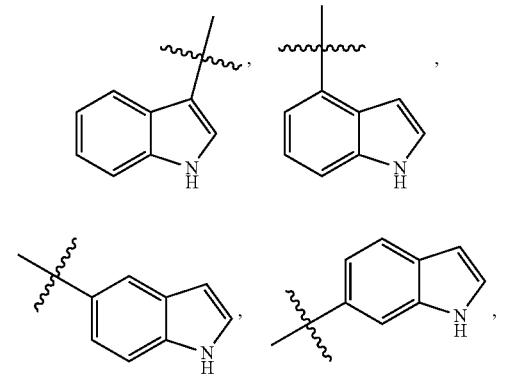

Additional non-limiting examples of "heteroaryl" groups that are bicyclic include:

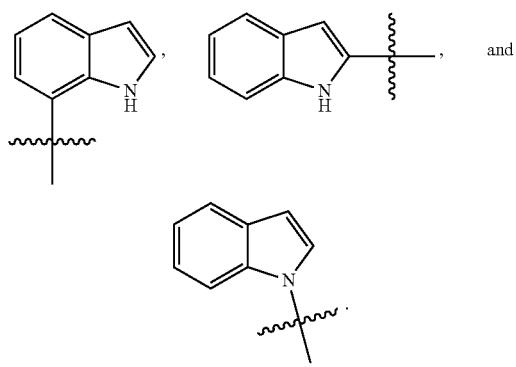

Additional non-limiting examples of "heteroaryl" groups that are bicyclic include:

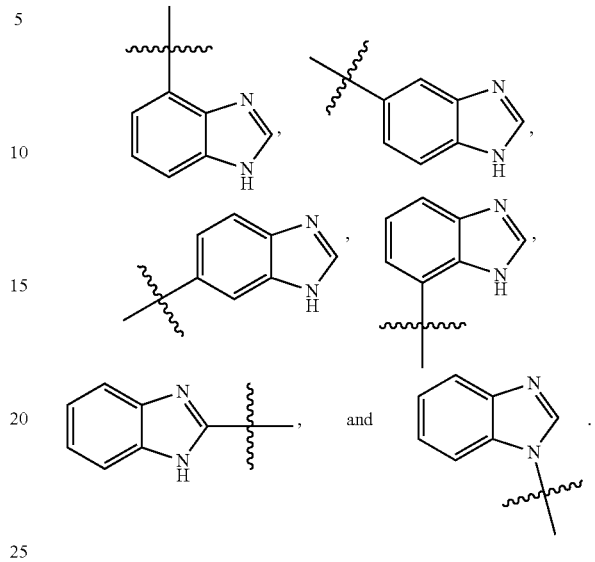

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

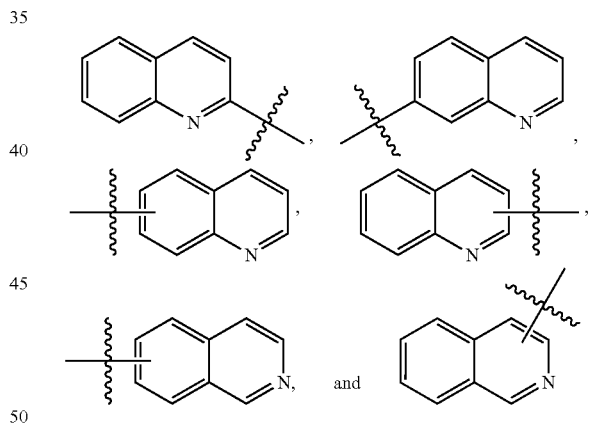

In one embodiment "heteroaryl" is "substituted heteroaryl"

The term "optionally substituted" denotes the substitution of a group herein by a moiety that forms a stable molecule and meets the desired purpose of the invention and includes, but is not limited to alkyl, heteroalkyl, cycloalkyl, heterocycloalkyl, aryl, heteroaryl, alkoxy, cycloalkoxy, heterocycloalkoxy, aryloxy, heteroaryloxy, amino, alkylamino, dialkylamino, arylamino, diarylatnino, heteroarylamino, alkylsufonatnino, atylsufonamino, alkylimino, arylimino, alkylsulfonimino, arylsulfonimino, hydroxyl, halo, sulfhydryl, alkylthio, arylthio, alkylsulfonyl, arylsulfonyl, acylamino, aminoacyl, aminothioacyl, amidino, guanidine, ureido, cyano, nitro, azido, acyl, thioacyl, acyloxy, carboxyl, carboxyl ester, alkanoyl, carboxamide, alkylsufinyl, haloalkyl, $B(OH)_2$, phosphate, phosphonate, and haloalkoxy. Such groups may be further substituted, for example with

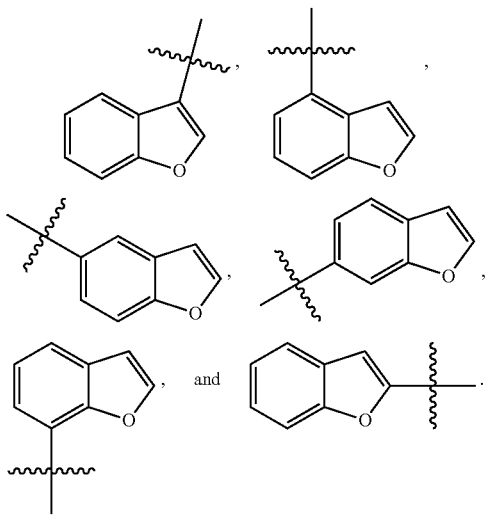

hydroxyl, alkyl, alkoxy, halogen, and amino, in such a manner that results in a stable moiety.

In one embodiment a group described herein that can be substituted with 1, 2, 3, or 4 substituents is substituted with one substituent.

In one embodiment a group described herein that can be substituted with 1, 2, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

Any compound used in or formed by the processes described herein may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvent are water, ethanol, dimethyl sulfoxide, acetone, and other common organic solvents. The term "hydrate" refers to a molecular complex comprising a compound as described herein and water. Solvates in accordance with this disclosure include those wherein the solvent may be isotopically substituted, e.g. $D_2O$, $d_6$-acetone, and $d_6$-DMSO. A solvate can be in a liquid or solid form.

Any compound used in or formed by the processes described herein may be modified by making inorganic or organic acid or base addition salts thereof. The salts of the present compounds can be synthesized from a parent compound that contains a basic or acidic moiety by conventional chemical processes. Generally, such salts can be prepared by reacting free acid forms of these compounds with a stoichiometric amount of the appropriate base (such as Na, Ca, Mg, or K hydroxide, carbonate, bicarbonate, or the like), or by reactive free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practical. Salts of the present compounds further include solvates of the compound and the compound salts.

Examples of salts as described herein include, but are not limited to, mineral or organic acid salts of basic residues such as amines; alkali or organic salts of acidic residues such as carboxylic acids; and the like. The salts described herein include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, make, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC-(CH2)n-COOH where n is 0-4, and the like, or using a different acid that produces the same counterion.

Olefin Reactants of Formula I and Formula IV

The process of the present invention involves an olefin reactant. In some embodiments, the olefin reactant is an asymmetric olefin, i.e., the two substituents attached to one of the olefinic carbons are not the same as the two substituents attached to the other olefinic carbon. In some embodiments, the olefin reactant contains a terminal olefin, i.e., one of the olefinic carbons has two hydrogen atoms, and therefore no carbon atoms, as substituents. In other embodiments, the olefin reactant contains a non-terminal olefin, meaning that each olefinic carbon has at least one non-hydrogen substituent. In some embodiments, the olefin reactant is a tri-substituted olefin containing three non-hydrogen substituents.

In some embodiments, for example embodiments of the process shown in Scheme 1, the olefin reactant is a compound of Formula I:

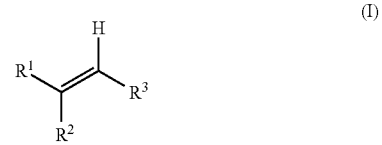

(I)

wherein $R^1$, $R^2$, and $R^3$ are defined as above.

Non-limiting examples of olefin reactants of Formula I that may be used in the present process include:

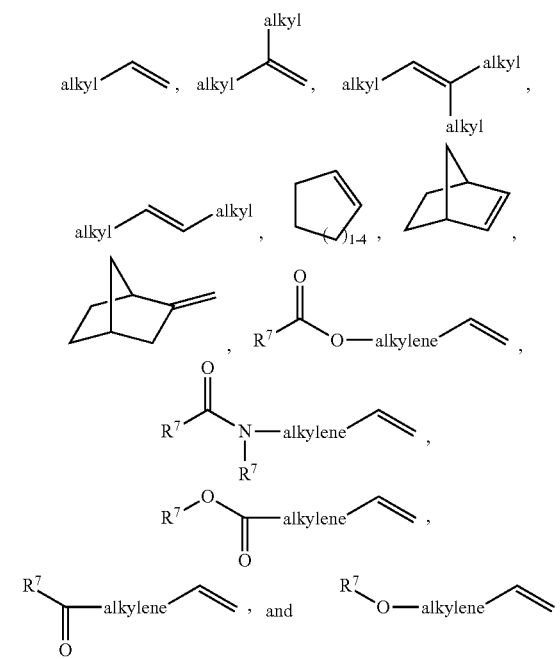

each of which may be optionally substituted with one or more substituents as described herein that do not adversely affect the desired reaction.

Non-limiting examples of olefin reactants of Formula I that may be used in the present process include:

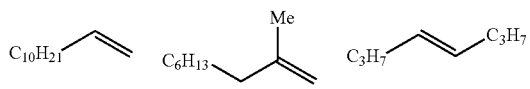

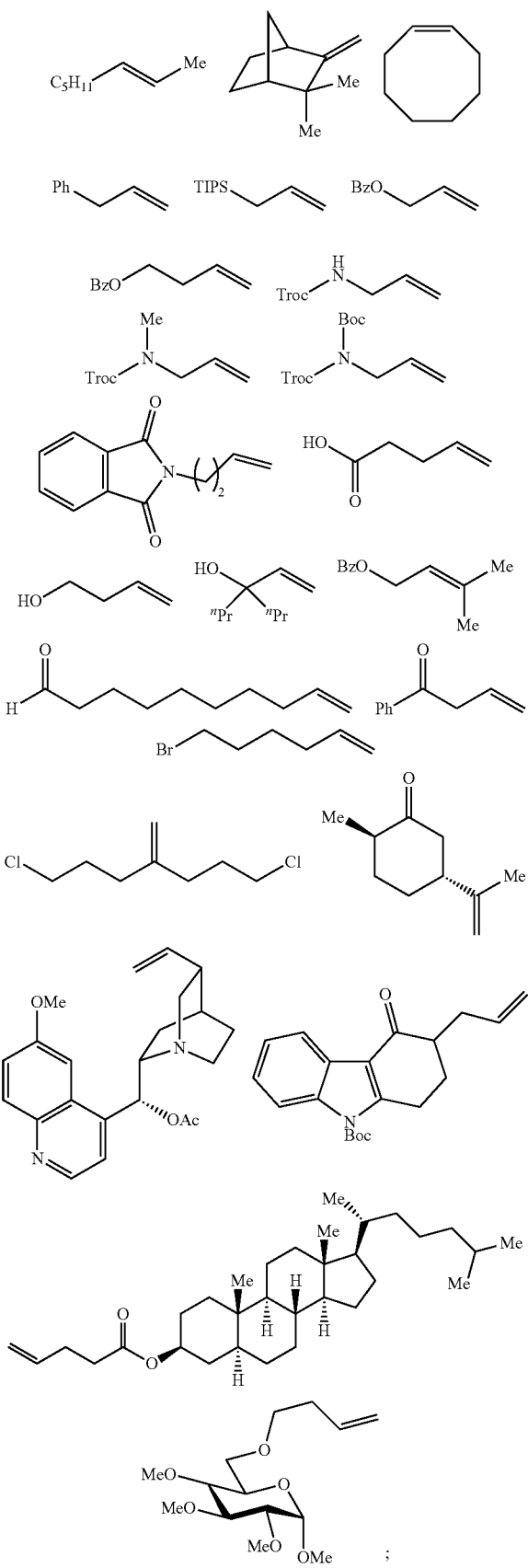

Additional non-limiting examples of olefin reactants of Formula I include

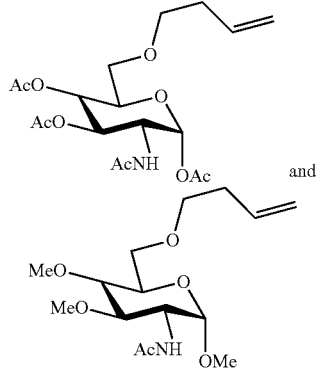

and each of which may be optionally substituted with one or more substituents as described herein that do not adversely affect the desired reaction.

In other embodiments, for example embodiments of the process shown in Scheme 2, the olefin reactant is an alkene containing an electron-withdrawing group, for example an enone, an acrolein, an acrylate, an acrylamide, or an acrylonitrile. In some embodiments, the olefin reactant is a compound of Formula IV:

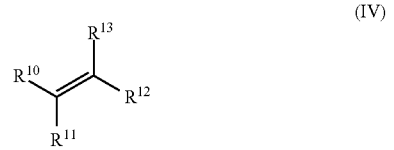

(IV)

wherein $R^{10}, R^{11}, R^{12}$ and $R^{13}$ are defined as above.

In one embodiment, the olefin reactant is a compound of Formula IVa:

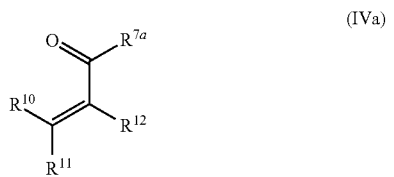

(IVa)

wherein $R^{10}$, $R^{11}$, $R^{12}$, and $R^{7a}$ are defined as above.

In one embodiment, the olefin reactant is a compound of Formula IVb:

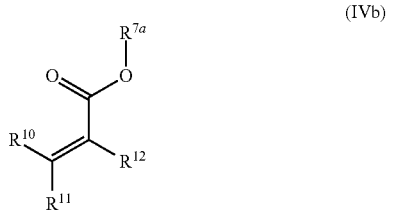

(IVb)

wherein $R^{10}$, $R^{11}$, $R^{12}$, and $R^{7a}$ are defined as above.

In one embodiment, the olefin reactant is a compound of Formula IVc:

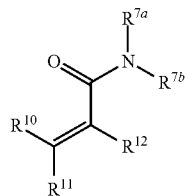
(IVc)

wherein $R^{10}$, $R^{11}$, $R^{12}$, and $R^{7a}$ and $R^{7b}$ are defined as above.

In one embodiment, the olefin reactant is a compound of Formula IVd:

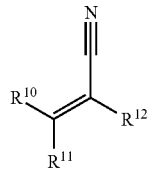
(IVd)

wherein $R^{10}$, $R^{11}$ and $R^{12}$ are defined as above.

In one embodiment, the olefin reactant is a compound of Formula IVe or Formula IVf:

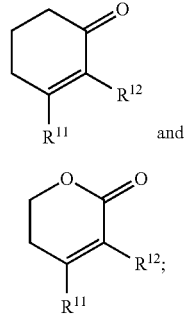
(IVe)
(IVf)

wherein $R^{11}$ and $R^{12}$ are defined as above.

Non-limiting examples of the olefin reactant of Formula IV include:

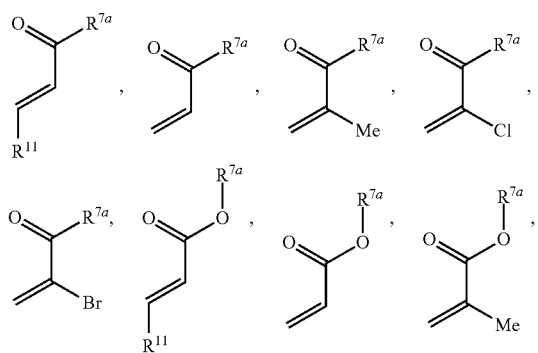

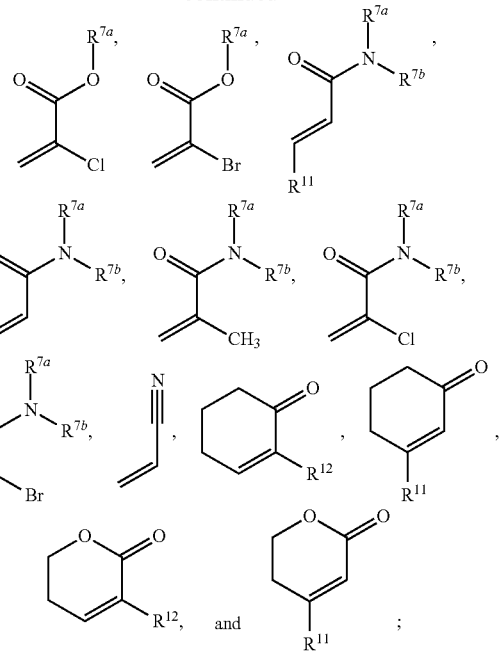

each of which may be optionally substituted with one or more substituents as described herein that do not adversely affect the desired reaction.

Additional non-limiting examples of the olefin reactant of Formula IV include:

-continued

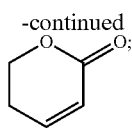

each of which may be optionally substituted with one or more substituents as described herein that do not adversely affect the desired reaction.

Silylazide Reactant of Formula II

The process of the present invention also includes a silylazide reactant. In some embodiments, the silylazide reactant is a trialkylazide. In some embodiments, the silylazide reactant is a compound of Formula II:

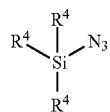

(II)

$R^4$ is independently selected at each occurrence from alkyl or cycloalkyl; or two $R^4$ groups may be brought together with the silicon to which they are attached to form a cycloalkyl ring.

In one embodiment, the silylazide reactant is trimethylsilylazide.

In another embodiment, the silylazide reactant is triethylsilylazide.

In another embodiment, the silylazide reactant is (tert-butyldimethylsilyl)azide.

Organic Promoters

The process of the present invention also includes an organic promoter. In some embodiments, the organic promoter is a compound of Formula IX or Formula X:

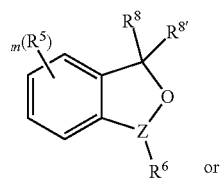

(IX)

or

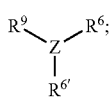

(X)

wherein Z is I; and
$R^5$, $R^6$, $R^{6'}$, $R^8$, $R^{8'}$, and m are defined as above.

In one embodiment, the organic promoter is a compound of Formula IXa:

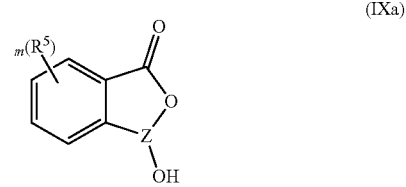

(IXa)

wherein $R^5$, Z and m are defined as above.

In another embodiment, the organic promoter is a compound of Formula IXb:

(IXb)

wherein $R^5$, $R^7$, Z, and m are defined as above. In preferred embodiments of Formula IXb, $R^7$ is an electron withdrawing substituent, for example trifluoromethyl or trichloromethyl.

In another embodiment, the organic promoter is a compound of Formula IXc:

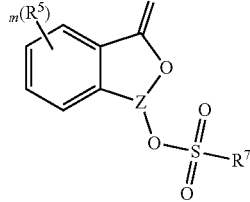

(IXc)

wherein $R^5$, $R^7$, Z, and m are defined as above. In preferred embodiments of Formula IXc, $R^7$ is an electron withdrawing substituent, for example trifluoromethyl or trichloromethyl.

In another embodiment, the organic promoter is a compound of Formula IXd:

(IXd)

wherein $R^5$, Z and m are defined as above.

In another embodiment, the organic promoter is a compound of the formula

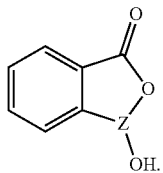

In another embodiment, the organic promoter is a compound of the formula

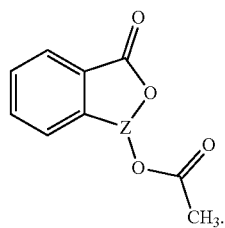

In another embodiment, the organic promoter is a compound of the formula

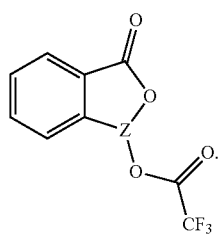

In another embodiment, the organic promoter is a compound of the formula

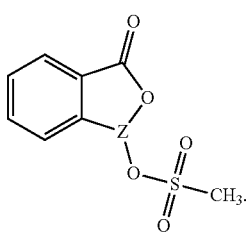

In another embodiment, the organic promoter is a compound of the formula

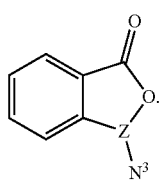

In one embodiment, the organic promoter is a compound of Formula Xa:

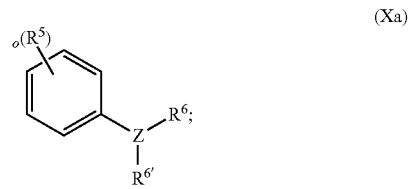

(Xa)

wherein $R^5$, $R^6$, $R^{6'}$, and Z are as defined above; and o is 1, 2, 3, 4, or 5.

In one embodiment, the organic promoter is a compound of Formula Xb:

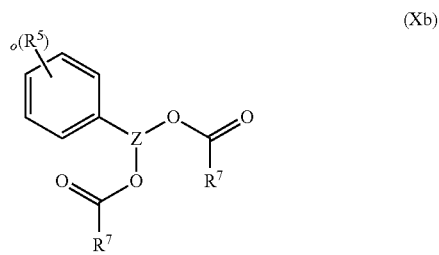

(Xb)

wherein $R^5$, $R^7$, Z, and o are defined as above. In preferred embodiment of Formula Xb, $R^7$ is an electron withdrawing substituent, for example trifluoromethyl or trichloromethyl.

In one embodiment, the organic promoter is a compound of the formula Xc:

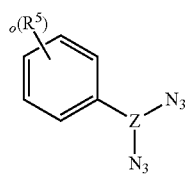

wherein $R^5$, Z, and o are defined as above.

In one embodiment, the organic promoter is a compound of the formula

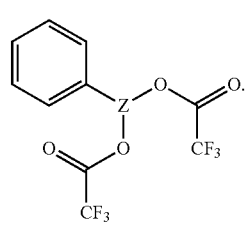

In one embodiment, the organic promoter is a compound of the formula
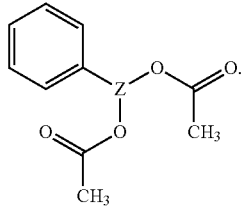
In another embodiment, a compound is provided of Formula VII:
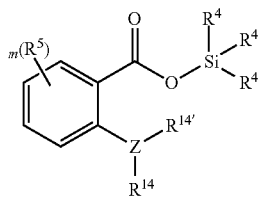
Wherein $R^4$, $R^5$, $R^{14}$, $R^{14'}$, Z, and m are defined as above.
Non-limiting examples of compounds of Formula VII include:
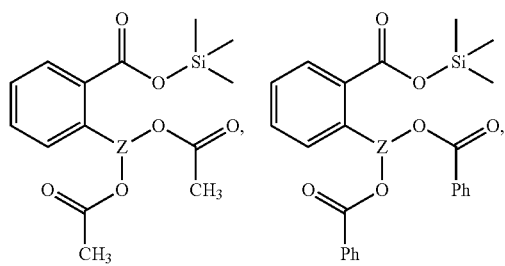
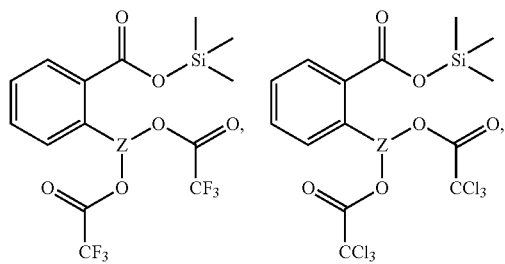
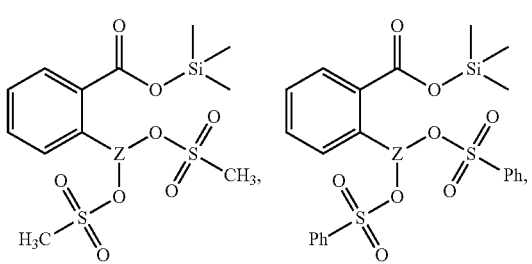
-continued
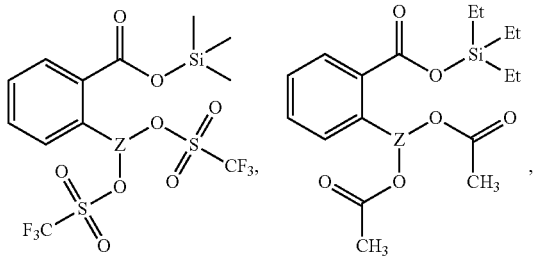
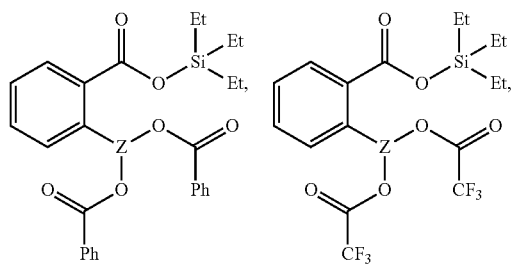
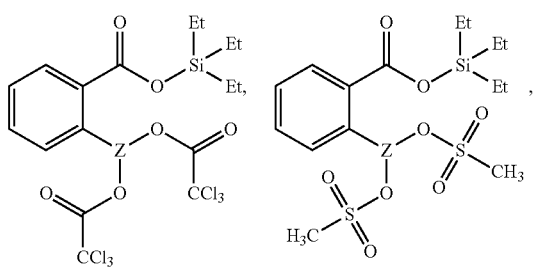
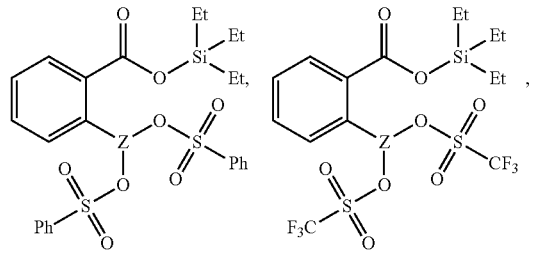
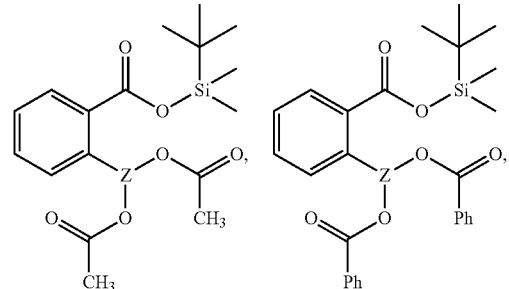
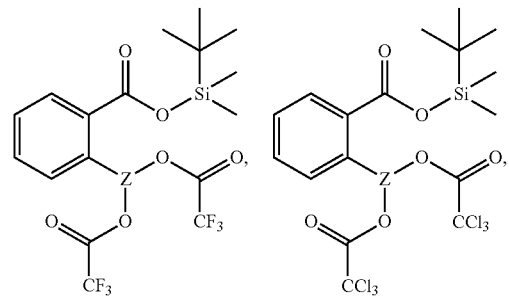

-continued

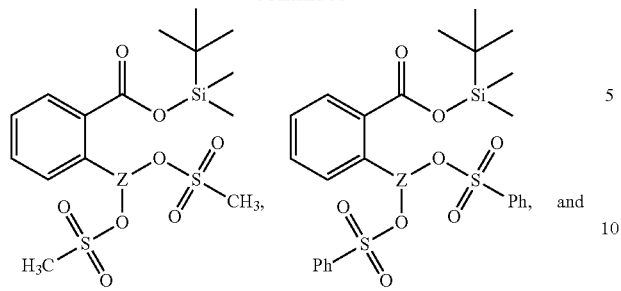

wherein Z is I. For example,

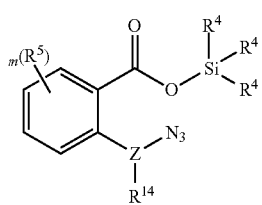

As the skilled worker can appreciate, the above molecules of Formula VII can be modified to have mixed alkyl groups on the silicon, for example two ethyl groups and one methyl group, and to have substituents on any apparent phenyl group, for example a methyl, methoxy, trifluoromethyl, chloro, or fluoro group.

In another embodiment, a compound is provided of Formula VIII:

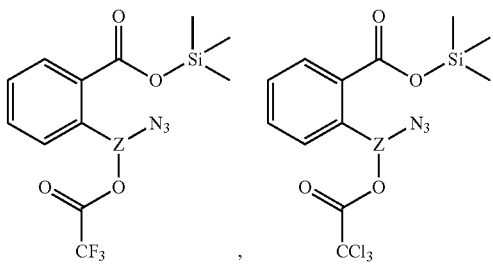

Wherein $R^4$, $R^5$, $R^{14}$, Z, and m are defined as above.

Non-limiting examples of compounds of Formula VIII include:

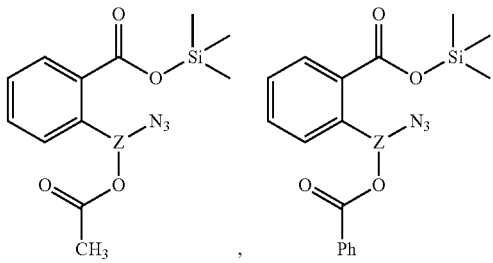

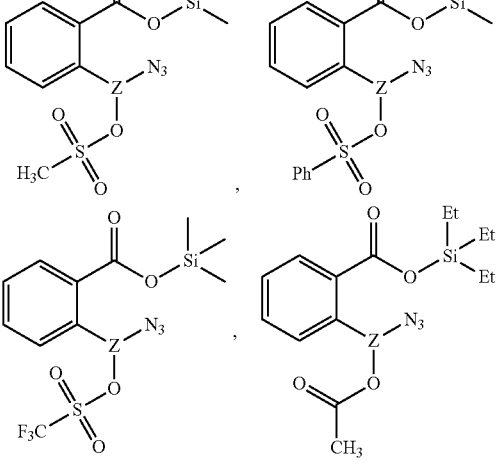

-continued

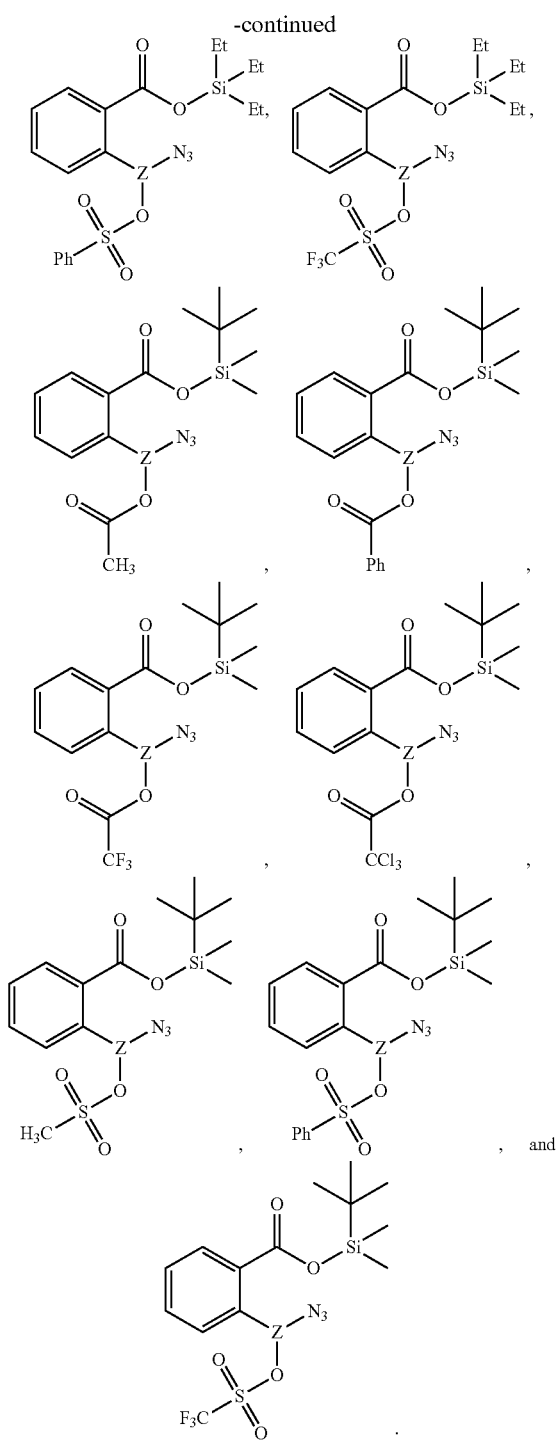

As the skilled worker can appreciate, the above molecules of Formula VII can be modified to have mixed alkyl groups on the silicon, for example two ethyl groups and one methyl group, and to have substituents on any apparent phenyl group, for example a methyl, methoxy, trifluoromethyl, chloro, or fluoro group, Hydrogen Bond Donors The process of the present invention includes the use of a hydrogen bond donor. In one embodiment, the hydrogen bond donor is water.

In some embodiments, the hydrogen bond donor comprises water and an optional second hydrogen bond donor. In some embodiments, the second hydrogen bond donor is selected from an organic acid or a mineral acid.

In one embodiment, the second hydrogen bond donor is formic acid.

In one embodiment, the second hydrogen bond donor is an alkylcarboxylic acid optionally substituted with one or more substituents selected from alkyl, heteroalkyl, cycloalkyl, heterocycloalkyl, aryl, heteroaryl, alkoxy, cycloalkoxy, heterocycloalkoxy, atyloxy, heteroaryloxy, amino, alkylamino, dialkylamino, arylamino, diarylamino, heteroarylamino, alkylsufonamino, arylsufonamino, alkylimino, arylimino, alkylsulfonimino, arylsulfonitnino, hydroxyl, halo, sulthydryl, alkylthio, arylthio, alkylsulfonyl, arylsulfonyl, acylamino, aminoacyl, aminothioacyl, amidino, guanidine, ureido, cyano, nitro, azido, acyl, thioacyl, acyloxy, carboxyl, carboxyl ester, alkanoyl, carboxamide, alkylsufinyl, haloalkyl, B (PH)$_2$, phosphate, phosphonate, and haloalkoxy. In one embodiment, the second hydrogen bond donor is trifluoroacetic acid.

In one embodiment, the second hydrogen bond donor is a (cycloalkyl)carboxylic acid optionally substituted with one or more substituents selected from alkyl, heteroalkyl, cycloalkyl, heterocycloalkyl, aryl, heteroaryl, alkoxy, atyloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is a (heteroalkyl)carboxylic acid optionally substituted with one or more substituents selected from alkyl, heteroalkyl, cycloalkyl, heterocycloalkyl, aryl, heteroaryl, alkoxy, aryloxyami no, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is a (heterocycloalkyl)carboxylic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is an arylcarboxylic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is a (heteroaryl)carboxylic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is sulfuric acid.

In one embodiment, the second hydrogen bond donor is an alkylsulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy. In one embodiment, the second hydrogen bond donor is methanesulfonic acid. In one embodiment, the second hydrogen bond donor is trifluoromethylsulfonic acid.

In one embodiment, the second hydrogen bond donor is an (cycloalkyl)sulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy, In one embodiment, the second hydrogen bond donor is a (heteroalkyl)sulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is a (heterocycloalkyl)sulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is an arylsulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the second hydrogen bond donor is a (heteroaryl)sulfonic acid optionally substituted with one or more substituents selected from alkyl, heteroalkyl, cycloalkyl, heterocycloalkyl, aryl, heteroaryl, alkoxy, aryloxyamino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy.

In one embodiment, the hydrogen bond donor is a chiral hydrogen bond donor. Representative examples of chiral hydrogen bond donors are described in Doyle. A. G. and Jacobsen, L. N. Chemical Reviews 2007, 107 , 5713, incorporated herein by reference in its entirety.

Amounts and Relative Ratios of Reaction Components

The absolute and relative amounts of the various components in the inventive process for making nitrogen-containing organic compounds can vary as desired to achieve the desired goal.

In some embodiments, the benziodoxole is typically present in an amount between about 5 and about 50 mol %) relative to the amount of olefin reactant. In one embodiment, the benziodoxole is present in an amount between about 5 and about 30 mol % relative to the amount of olefin reactant. In another embodiment, the benziodoxole is present in an about between about 7 and about 20 mol % relative to the amount of olefin reactant. In one embodiment, the benziodoxole is present in at least about 5 mol %, at least about 6 mol %, at least about 7 mol %, at least about 8 mol %, at least about 9 mol %, at least about 10 mol %, at least about 15 mol %, at least about 20 mol %, at least about 25 mol %, at least about 30 mol %, at least about 35 mol %, at least about 40 mol %, or at least about 50 mol %, relative to the amount of olefin reactant.

In some embodiments, the silylazide is typically present in an amount between about 1.8 and about 3.0 equivalents relative to the amount of olefin reactant. In one embodiment, the silylazide is present in an amount between about 2.0 and about 2.5 equivalents relative to the amount of olefin reactant. In one embodiment, the silylazide is present in at least about 1.8 equivalents, 1.9 equivalents, 2.0 equivalents, 2.1 equivalents, 2.2 equivalents, 2.3 equivalents, 2.4 equivalents, 2.5 equivalents, 2.6 equivalents, 2.7 equivalents, 2.8 equivalents, 2.9 equivalents, or 3.0 equivalents relative to the amount of olefin reactant. In one embodiment, the silylazide is present in an at least about the sum of the equivalents of the hydrogen bond donor and twice the equivalents of the benziodoxole.

In embodiments where water is the sole hydrogen bond donor, water is typically present in an amount between about 0.6 to about 1.5 equivalents relative to the amount of olefin reactant. In some embodiments, water is present in an amount between about 0.8 to about 1.2 equivalents relative to the amount of olefin reactant. In some embodiment, water is present in at least about 0.6 equivalents, 0.7 equivalents, 0.8 equivalents, 0.9 equivalents, 1.0 equivalents, 1.1 equivalents, 1.2 equivalents, 1.3 equivalents, 1.4 equivalents, or 1.5 equivalents relative to the amount of olefin reactant.

In embodiments where water is used in combination with a second hydrogen bond donor, the sum of the equivalents of water and the equivalents of the second hydrogen bond donor is typically between about 0.8 and about 1.2 relative to the amount of olefin reactant. In some embodiments, between about 0.6 and 0.8 equivalents of water and between about 0.2 and 0.6 equivalents of the second hydrogen bond donor are used. In one embodiment, about 0.6 equivalents of water and about 0.2 equivalents of the second hydrogen bond donor are used. In one embodiment, about 0.7 equivalents of water and about 0.2 equivalents of the second hydrogen bond donor are used. In one embodiment, about 0.8 equivalents of water and about 0.2 equivalents of the second hydrogen bond donor are used. In one embodiment, about 0.6 equivalents of water and about 0.6 equivalents of the second hydrogen bond donor are used.

Azide Products of Formula III and Formula IV

The processes of the present invention produce an organic azide product or an azide-containing oligomer or polymer product. In the hydroazidation reaction, the anti-Markovnikov product is the organic azide that results when the azido group attaches to the less substituted of the olefinic carbons. Thus when the olefin reactant is a terminal olefin, the anti-Markovnikov product is a primary organic azide.

In some embodiments, the product is substantially or exclusively the anti-Markovnikov product. In some embodiments, the product is a mixture of anti-Markovnikov and Markovnikov products, with the majority in the anti-Markovnikov orientation. In other embodiments, the anti-Markovnikov to Markovnikov orientation is in a ratio within the range of about 1:2 to 100:1, or within about 1:11 to 50:1. For example, the ratio of anti-Markovnikov to Markovnikov products is at at least about 1:1.5, at least about 1:1, at least about 2:1, at least about 3:1, at least about 4:1, at least about 5:1, at least about 10:1, at least about 20:1, at least about 50:1, or more.

Furthermore, in some embodiments the crude yield of anti-Markovnikov product (i.e. prior to purification) is at least about 50% (based on the amount of olefin reactant at the beginning of the reaction), at least about 60%, at least about 70%, at least about 80%, at least about 90%, at least about 95%, or greater.

In some embodiments, for example the reaction shown in Scheme 1, the organic azide product is a compound of Formula III:

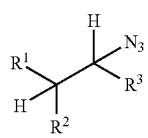
(III)

wherein $R^1$, $R^2$, and $R^3$ are defined as above.

In some embodiments, a product of Formula III is formed upon subjecting an olefin reactant of Formula I to the processes described herein, for example the reaction shown in Scheme 1.

In other embodiments, for example the reaction shown in Scheme 2, the product is an azide-containing oligomer or polymer of Formula V:

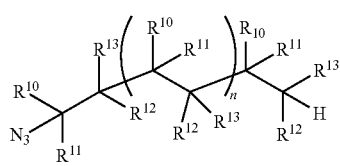
(V)

wherein $R^{10}$, $R^{11}$, $R^{12}$, $R^{13}$, and n are defined as above.

In some embodiments, for example the reaction shown in Scheme 2, the product is a mixture of compounds of Formula V having a range of values of n. For example, the product is a mixture of compounds of Formula V wherein n is from 1 to 25, from 5 to 20, from 6, to 19, from 8 to 15, or from 10 to 12. In some embodiment, the product is a mixture of compounds of Formula V wherein n is from 10 to 20, from 11 to 20, from 12 to 20, from 13 to 20, from 14 to 20, from 15 to 20, from 14 to 19, from 15 to 19, from 16 to 19, or from 17 to 18.

In some embodiments, a product of Formula V is formed upon subjecting an olefin of Formula IV to the processes described herein.

Mechanisms and Process Parameters

The process of the present invention may be conveniently carried out in an environmentally friendly non-metal containing one-pot process to create organic azides with anti-Markovnikov selectivity. By "one-pot" is meant that the olefin is combined with all necessary reactants to form the desired product in the same reaction vessel—no transfer and/or isolation of intermediate compounds is necessary.

While not wishing to be bound by any one theory, the mechanism for some embodiments of the present invention, for example the reaction shown in Scheme 1 wherein water is hydrogen bond donor, may be similar to that shown in Scheme 5:

Scheme 5

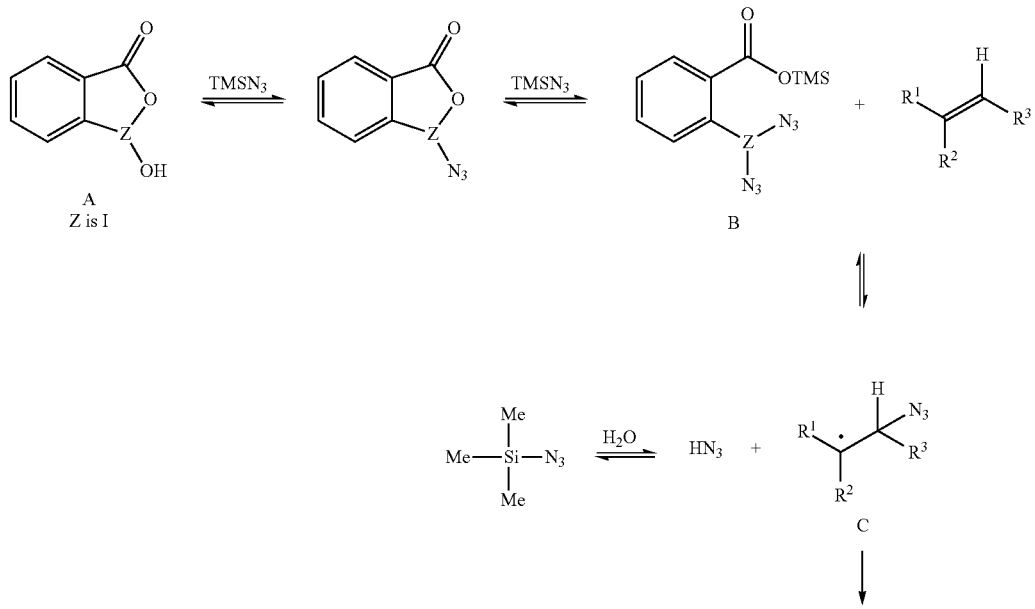

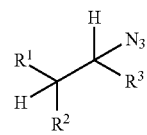

Reaction of the benziodoxole A with the silylazide provides a transient iodine(III) diazide species B which subsequently reacts with the olefin to form a beta-azidoalkyl radical species C. This species is then trapped by hydrazoic acid, formed by reaction of the silylazide and the hydrogen bond donor, to yield the desired organic azide product.

Also not wishing to be bound by any one theory, the mechanism for other embodiments of the present invention, for example the reaction shown in Scheme 1 wherein water and trifluoroacetic acid are the hydrogen bond donor, may be similar to that shown in Scheme 6:

mediate C upon reaction with another equivalent of trimethylsilyl trifluoracetate. Intermediate B may equilibrate to intermediate C by reaction with trimethylsilyl trifluoroacetate, and intermediate C may equilibrate with intermediate B by reaction with trimethylsilylazide. Intermediate B subsequently reacts with the olefin to form a beta-azido radical species. This radical species is then trapped by hydrazoic acid that was previously formed to yield the desired organic azide product.

Also not wishing to be bound by any one theory, the mechanism for other embodiments of the present invention,

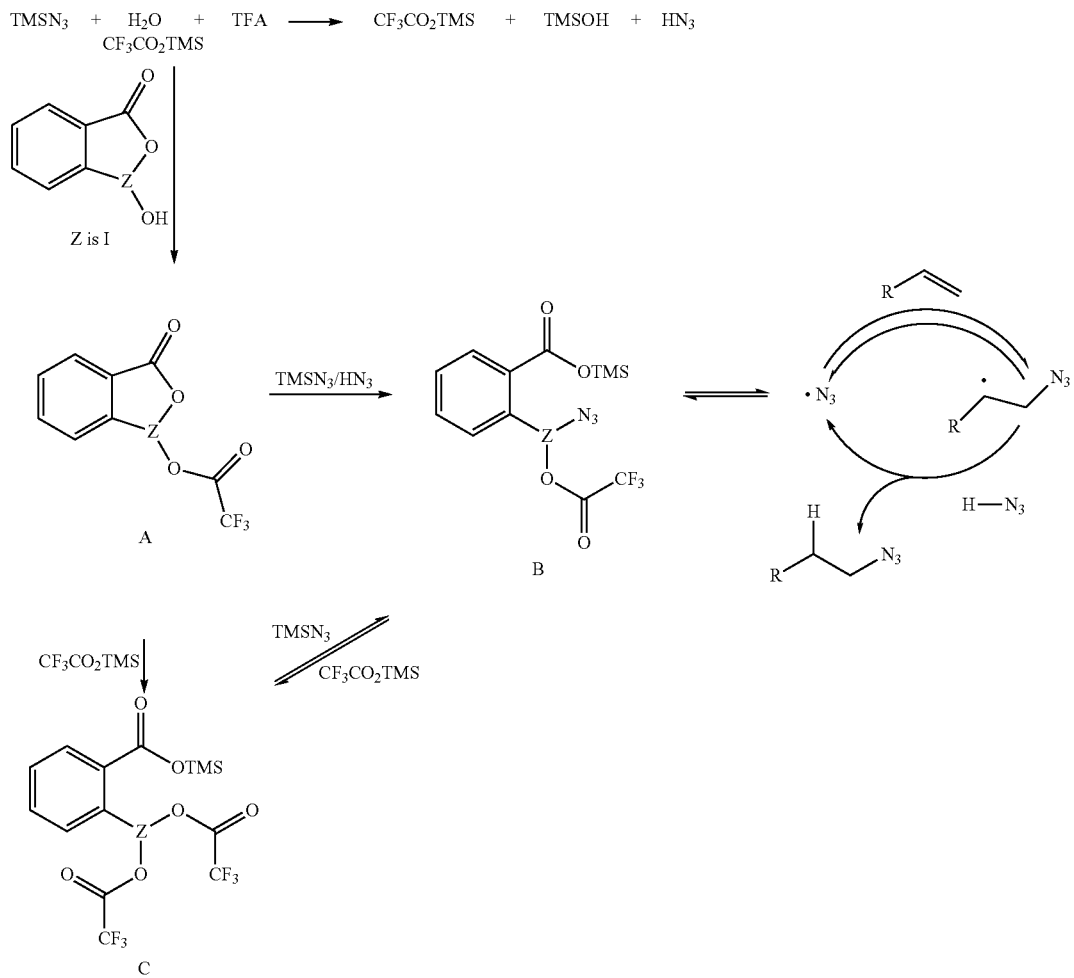

Reaction of trimethylsilylazide with water and trifluoroacetic acid provides trimethylsilyl trifluoroacetate and h.ydrazoic acid. Reaction of ttitnethylsilyl trifluoroacetate with the benziodoxole provides the trifluoroacetylated intermediate A, which may either be converted into intermediate B upon reaction with trimethylsilylazide or may form intermediate B upon reaction with trimethylsilylazide or may form interfor example the reaction shown in Scheme 1 wherein water and trifluoroacetic acid are the hydrogen bond donor and 3-oxo-1$\lambda^3$-benzo[d][1,2]iodaoxol-1(3H)-yl 2,2,2-trifluoroacetate is used as the organic promoter, may be similar to that shown in Scheme 7:

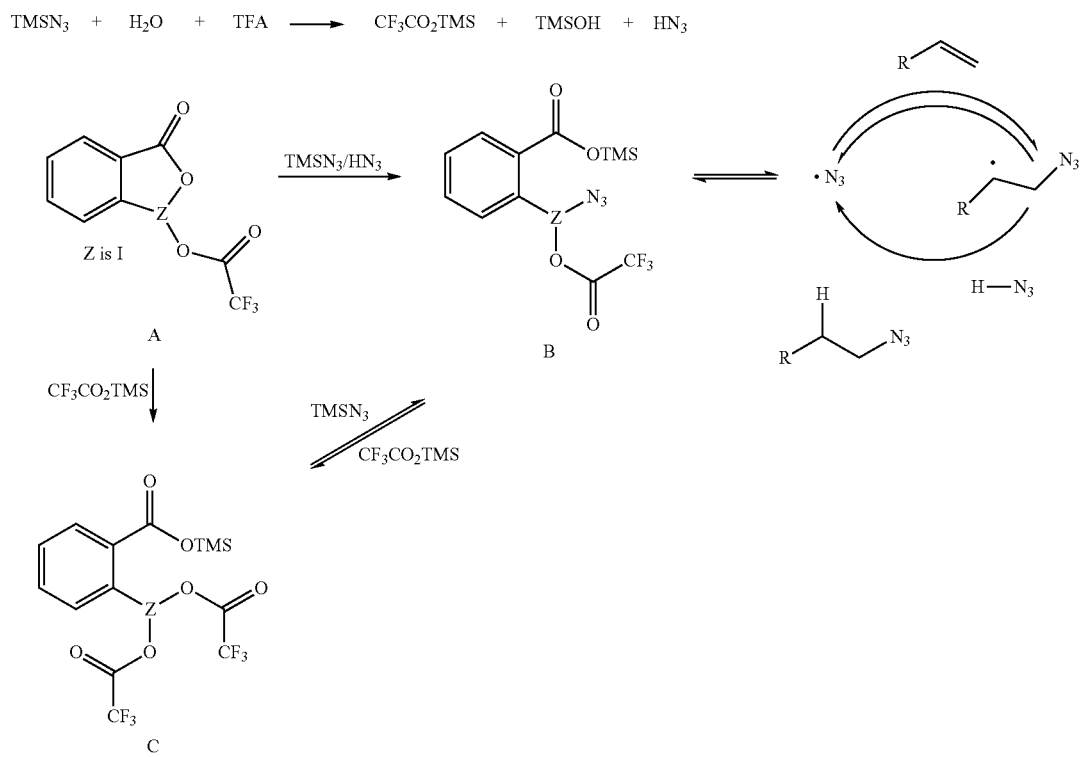

Scheme 7

Reaction of trimethylsilylazide with water and trifluoroacetic acid provides trimethylsilyt trifluoroacetate and hydrazoic acid. The benziodoxole A may subsequently be converted to either intermediate B on reaction with trimethylsilylazide or intermediate C upon reaction reaction with trimethylsilyl trifluoroacetate. Intermediate B may equilibrate to intermediate C by reaction with tritnethylsilyl trifluoroacetate, and intermediate C may equilibrate with intermediate B by reaction with trimethylsilylazide. Intermediate B subsequently reacts with the olefin to form a beta-azido radical species. This radical species is then trapped by hydrazoic acid that was previously formed to yield the desired organic azide product.

Any organic solvents may be used in this process that achieves the desired result. Exemplary solvents include acetone, ethyl acetate (EtOAc), dichloromethane($Ch_2Cl_2$), acetonitrile (MeCN), 1,2-dichloroethane (DCE), nitromethane, hexanes, pentane, toluene, benzene, petroleum ether, 2-butanone, chlorobenzene, chloroform ($CHCl_3$), cyclohexane, heptane, o-xylene, air-xylene, p-xylene, and combinations thereof. In on embodiment, the solvent is selected from ethyl acetate (EtOAc), dichloromethane ($CH_2Cl_2$), or chloroform ($CHCl_3$). In one embodiment, the solvent is ethyl acetate (EtOAc). In one embodiment, the solvent is dichloromethane ($CH_2Cl_2$). In one embodiment, the solvent is chloroform ($CHCl_3$).

In one aspect, the process is typically performed in an organic solvent at a concentration of the olefin reactant if at least about 1.0 molar. In some embodiments, the reaction is performed at an olefin reactant concentration between about 1.0 molar and about 2.3 molar. In some embodiments, the reaction is performed at a concentration of the olefin reactant of at least about 1.0 molar, at least about 1.1 molar, at least about 1.2 molar, at least about 1.3 molar, at least about 1.4 molar, at least about 1.5 molar, at least about 1.6 molar, at least about 1.7 molar, at least about 1.8 molar, at least about 1,9 molar, at least about 2.0 molar, at least about 2.1 molar, at least about 2.2 molar, at least about 2.3 molar, or more.

The processes of interest are typically performed at room temperature, i.e. a temperature between about 20° C. and 25° C., but may be performed at a lower temperature if deemed necessary, i.e. at a temperature of no less than about 4° C., no less than about 5° C., no less than about 10° C., no less than about 15° C., or no less than about 20° C.

In some embodiments, the processes of interest may further include appropriate purification and isolation steps to remove impurities and reactants from the product organic azide. Furthermore, when the product contains a mixture of anti-Markovnikov and Markovnikov products, the product may be purified the remove the undesired addition product.

In some embodiments, the processes of interest are suitable for preparation of organic azides on any desired scale, including preparatory/research scale and industrial scale. Thus, the reaction vessel in which the processes are carried out may be any convenient size, such as from microliter scale to multi-liter (at least about 5, 10, 100 liters, or greater) scale, Reaction times and reaction conditions (e.g., temperature, atmosphere, etc.) will vary and may be determined by reference to the examples and disclosure provided herein, as well as routine experimentation and consultation of the relevant literature when necessary. Typical reaction times are at least about 30 minutes, at least about 1 hour, at least about 2 hours, at least about 3 hours, at least about 4 hours, at least about 5 hours, at least about 6 hours, or longer. In some embodiments, the processes described herein are run under such conditions so as to achieve the desired result.

Isotopic Substitutions and Deuterium Incorporation Processes

The process of the present invention can be carried out with isotopic, typically deuterated, compounds or solvents. For example, Formula I, Formula II, Formula III, Formula IV, Formula V, Formula VI, Formula VII, Formula VIII, Formula IX, Formula X, Formula XI, the organic promoter, or the hydrogen bond donor, may be selected to have at least one desired isotopic substitution of an atom, at an amount above the natural abundance of the isotope, i.e. enriched. Isotopes are atoms having the same atomic number but different mass numbers, i.e. the same number of protons but a different number of neutrons.

Examples of isotopes that can be incorporated into compounds of the invention include isotopes of hydrogen, carbon, nitrogen, oxygen, phosphorous, fluorine, chlorine, and iodine such as $^2H$, $^3H$, $^{11}C$, $^{13}C$, $^4C$, $^{15}N$, $^{17}O$, $^{18}O$, $^{18}F$, $^{31}P$, $^{32}P$, $^{35}S$, $^{36}Cl$, and $^{125}I$, respectively. In one non-limiting embodiment, the product azide is used to produce an isotopically labeled compound that is employed in metabolic studies (with for example $^{14}C$), reaction kinetic studies (with for example $^2H$ or $^3H$), detection or imaging techniques, such as positron emission tomography (PET) or single-photon emission computer tomography (SPECT) including drug or substrate tissue distribution assays. In particular, an $^{18}F$ labeled compound may be particularly desirable for PET or SPECT studies. Isotopically labeled compounds produced using this invention can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95, or 99% or more enriched in an isotope at any location of interest. In one non-limiting embodiment, deuterium is 90, 95%, or 99% enriched at a desired location.

In one non-limiting embodiment, the substitution of one or more hydrogen atoms for a deuterium atom can be provided in any one of Formula I, Formula II, Formula III, Formula IV, Formula V, Formula VI, Formula VII, Formula VIII, Formula IX, Formula X, or Formula XI. In one non-limiting embodiment, the substitution of a hydrogen atom for a deuterium occurs within a group selected from $R^1$, $R^2$, $R^3$, $R^4$, $R^5$, $R^6$, $R^{6'}$, $R^7$, $R^{7a}$, $R^{7b}$, $R^{7c}$, $R^8$, $R^{8'}$, $R^9$, $R^{10}$, $R^{11}$, $R^{12}$, and $R^{13}$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, $OCD_3$, etc.). In certain other embodiments, when two substituents are combined to form a cycle the unsubstituted carbons may be deuterated.

In one embodiment, a process is provided for the synthesis of a beta-deuteroalkyl azide of Formula VI as illustrated in Scheme 3 above, wherein $R^1$, $R^2$, $R^3$, $R^4$, and the organic promoter are defined as above; and the deuterium bond donor consists of deuterium oxide and optionally a deuterated acid selected from trifluoroacetic acid-d, acetic acid-$d_4$, trifluoromethanesulfonic acid-d, methanesulfonic acid-$d_4$, and formic acid-$d_2$. In one embodiment, the deuterium is 100% incorporated into the product of Formula VI. In another embodiment, the deuterium is partially incorporated into the product of Formula VI, for example, about 10%, 20%, 30%, 40%, 50%, 60%, 70%, 80%, 90%, 95%, 99%, 99.9%, 99.99%, or 99.999% incorporated.

In one embodiment, a process is provided for the synthesis of deuterated azide-containing oligomer or polymer of Formula XI as illustrated in Scheme 4 above, wherein $R^4$, $R^{10}$, $R^{11}$, $R^{12}$, $R^{13}$, and the organic promoter are defined as above; and the deuterium bond donor consists of deuterium oxide and optionally a deuterated acid selected from trifluoroacetic acid-d, acetic acid-$d_4$, trifluoromethanesulfonic acid-d, methanesulfonic acid-$d_4$, and formic acid-$d_2$. In one embodiment, the deuterium is 100% incorporated into the product of Formula XI. In another embodiment, the deuterium is partially incorporated into the product of Formula XI, for example, about 10%, 20%, 30%, 40%, 50%, 60%, 70%, 80%, 90%, 95%, 99%, 99.9%, 99.99%, 99.999% incorporated,

Subsequent Transformations of the Organic Azide Products

An organic azide as formed by the present process may be the final desired product, or it may be used as an intermediate through one or more additional reactions to provide a final desired. nitrogen-containing product. The reactions of organic azides have been extensively studied, the results of which are summarized in several reviews (see Brase, S. et al. Angewanche Chemie Internation Edition 2005, 44, 5188; Huang, D. and Yan. G. Adv. Synth. Catal. 2017, 359, 1600-1619; and Scriven, E. F. V. and Turnbull, K. Chem. Rev. 1988, 88, 297-368; each of which is incorporated herein by reference in its entirety). Thus in one embodiment, the process further comprises a subsequent step for transformation of the formed organic azide product. Non-limiting representative examples of possible transformations of the organic azide products are provided below.

An organic azide may be reacted with an alkyne in the presence of a metal catalyst to provide a triazole (see Tornoe, C. W. et al. Journal of Organic Chemistry 2002, 67, 3057; and Rostovtsev, V. V. et al. Angewandte Chemie International Edition 2002, 41, 2596). A representative example of this reaction is provided in Scheme 8 wherein $R^A$ is alkyl optionally substituted with aryl and $R^B$ is alkyl optionally substituted alkoxy, aryloxy, or aryl. In an alternative embodiment, and $R^A$ and $R^B$ are independently any variable defined herein.

Scheme 8

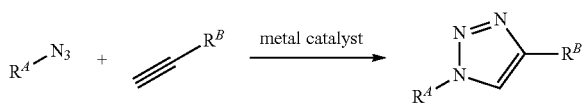

An organic azide may be converted to thermally, photochetnically, or with a metal catalyst into a reactive nitrene intermediate that may subsequently undergo a number of transformations such as cycloadditions or C—H insertions (see Dequirez, G. et al. Angewandie Chemie Internation Edition 2012, 51, 7384 for a review of modern nitrene chemistry). A representative example of this type of reaction is provided in Scheme 9:

Scheme 9

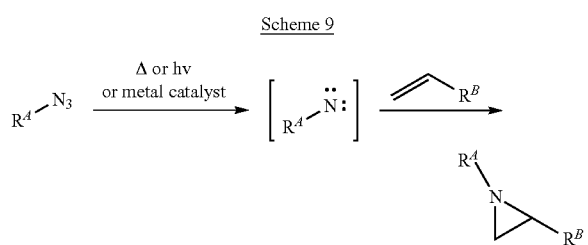

An organic azide can be reacted with a trialkyl or triaryl phosphine to form an iminophosphorane (see Gololobov, Y.G. and Kasukhin, L.F. Tetrahedron 1992, 48, 1353). This iminophosphorane intermediate can be reacted with water to form a primary amine or with an electrophile such as a ketone to form an imine. A representative example of these types of reactions is provided in Scheme 10 wherein R is alkyl or aryl, and $R^C$ and $R^D$ are independently selected from hydrogen and alkyl optionally substituted with aryl. In an alternative embodiment, R, $R^C$ and $R^D$ are independently any variable defined herein.

Scheme 10

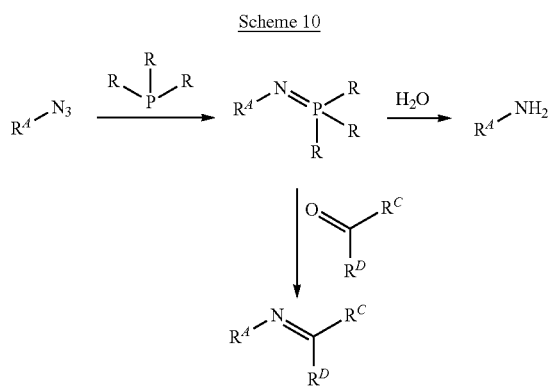

Bioconjugation Processes

In another aspect, processes are also provided for the conjugation of olefin-containing molecules to biomolecules of interest, i.e. for the covalent linkage of olefin-containing compounds to biomolecules of interest. An organic azide or azide-containing oligotner or polymer formed from an olefin using the processes described herein can be conjugated to an alkyne-containing modified biomolecule using an azide-alkyne cycloaddition reaction.

In one aspect, a process for the conjugation of an organic molecular ligand group to a modified biomolecule, wherein the organic molecular ligand contains an alkenyl group and the modified biomolecule contains an alkynyl group, is provided comptising:

(a) converting the alkenyl group of the organic molecular ligand to an azidoalkyl group using one of the processes described herein;

(b) optionally purifying the organic molecular ligand; and (c) reacting the azidoalkyl group of the organic molecular ligand with the alkynyl group of the modified biomolecule to form a 1,2,3-triazole group that covalently links the organic molecule to the modified biomolecule.

In another aspect, a process for the conjugation of an organic molecular ligand to a modified biomolecule, wherein the organic molecular ligand contains an alkenyl group and the modified biomolecule contains an alkynyl group, is provided comptising:

(a) converting the alkenyl group of the organic molecular ligand to an azidoalkyl group using the reaction shown in Scheme 1;

(b) optionally purifying the organic molecular ligand; and (c) reacting the azidoalkyl group of the organic molecular ligand with the alkynyl group of the modified biomolecule to form a 1,2,3-triazole group that covalently links the organic molecule to the modified biomolecule.

In another aspect, a process for the conjugation of an azide-containing oligomer or polymer formed from an organic molecular ligand to a modified biomolecule, wherein the organic molecular ligand contains an alkenyl group and the modified biomolecule contains an alkynyl group, is provided comprising:

(a) converting the alkenyl-containing organic molecular ligand to an azide-containing oligomer or polymer using the reaction shown in Scheme 2;

(b) optionally purifying the azide-containing oligomer or polymer; and (c) reacting the azide group of the oligomer or polymer with the alkynyl group of the modified biomolecule to form a 1,2,3-triazole group that covalently links the oligomer or polymer to the modified biomolecule.

The biomolecule can be a polypeptide including a protein, a polynucleotide such as a polydeoxyribonucleotide or a polyribonucleotide, a monosaccharide or polysaccharide, or a lipid or lipid-like molecule. The organic molecule may be a substrate, an inhibitor, a drug, a fluorescent probe, or any other olefin-containing group that may be useful to conjugate with a biomolecule for any purpose. Step (c) in any embodiments of the bioconjugation process can be performed ex vivo, in vitro, or in vivo depending on the desired application.

In one embodiment, reaction of the azidoalkyl group of the alkynyl group of the modified biomolecule occurs via a copper-catalyzed azide-alkyne cycloaddition (CuAAC) (see Tornoe, C. W. et al. Journal of Organic Chemistry 2002, 67, 3057; and Rostovtsev, V. V. et al. Angewandte Chemie International Edition 2002, 41, 2596, the entireties of which are incorporated herein by reference). The CuAAC reaction leads to selective formation of the 1,4-substituted 1,2,3-triazole product. The CuAAC reaction can be performed over a wide range of temperatures (0-160° C.) and pH values (4-12), and can even be performed in water. Typically sodium ascorbate is used as a reducing agent for the copper catalyst in a 3- to 10-fold excess, but hydrazine and hydroxylamine have also been used. Copper-stabilizing ligands may be also added to prevent unwanted copper-mediated oxidation of any functionality of the biomolecule, for example histidine and arginine residues in a polypeptide. Representative examples of copper-stabilizing ligands as used in bioconjugation applications include:

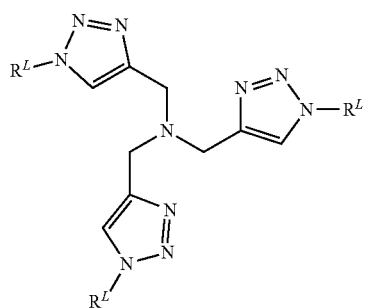

wherein $R^L$ can be benzyl, tert-butyl, or 3-hydroxypropyl.

Representative examples of the CuAAC reaction and its application in bioconjugation are described in: Bock, V. D. et al. European Journal of Organic Chemistry 2006, 51-68; Hen, C. D. et al. Pharmaceutical Research 2008, 25. 2216-2230; Himo, F. et al. Journal of the American Chemical Society 2005, 127, 210-216; Rodionov, V. O. et al. Angewandte Chemie International Edition 2005, 44, 2210-2215; Golas, P. L. et al. Macromolecules 2006, 39, 6451-6457; Hong, V. et al. Angewandte Chemie International Edition 2009, 48, 9879-9883; Besanceney-Webler, C. et al. Angewandte Chemie International Edition 2011, 50, 8051-8056; and Agard, N. J. et al. Journal of the American Chemical Society 2004, 126, 15046-15047; each of which is incorporated herein by reference in its entirety.

In one embodiment, the reaction of the azidoalkyl group of the alkynyl group of the modified biomolecule occurs via a strain-promoted azide-alkyne cycloaddition (SPAAC). The alkenyl group as used in the SPAAC reaction is housed within a cyclooctynyl ring. The high degree of ring stain (18 kcal/mol) allows the reaction to proceed under mild conditions with relatively fast reaction times. Solubility of the cyclooctynyl group in water can typically be increased by the inclusion of polyethyleneglycol (PEG) or sulfonate groups along the point of attachment to the biornolecule. The SPAAC reaction typically results in a mixture of 1,4-triazole regioisomers. Representative examples of cyclooctynyl groups that can be used include:

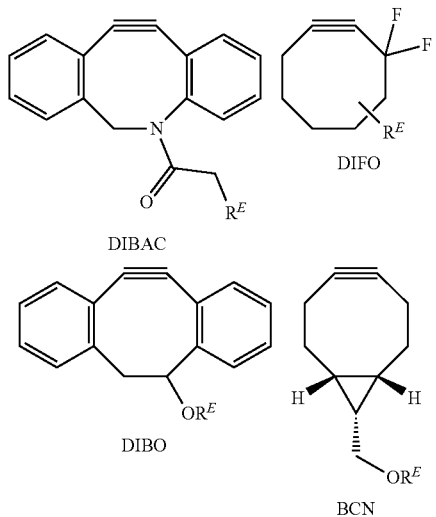

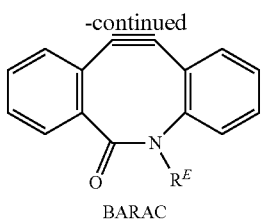

BARAC wherein $R^E$ is the biomolecule or a modified derivative thereof.

In some embodiments, a photolabile "caged" cyclooctynyl variant is used. These variants reveal the reactive alkyne functionality upon exposure to 350 nm light, allowing for spatially controlled bioconjugation reactions. A representative example of photoinduced cyclooctynyl release is provided in Scheme 11 below wherein $R^F$ is a substituted or unsubstituted alkyl. In an alternative embodiment, $R^F$ is any van able defined herein.

Scheme 11

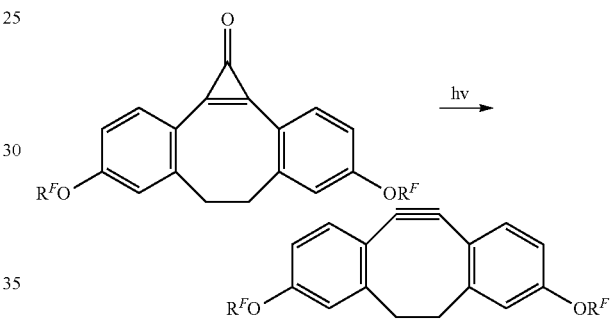

Representative examples of the SPAAC reaction and its application in bioconjugation are described in: Agard, N. J. et al. Journal of the American Chemical Society 2004, 126, 15046-15047; Baskin, J. M. et al. PNAS 2007, 104, 16793-16797; .Andronov, A, et al. Synthesis 2014, 46, 669-677; Dommerholt, J. et al. Topic in Current Chemistry 2016, 374, 16; Arumugam, S. et al. Pure and Applied Chemistry 2013, 85, 1499-1513; and Manova, R. et al. Angewandte Chemie International Edition 2011, 50, 5428-5430: each of which is incorporated herein by reference in its entirety.

The alkyne group may be installed on the biomolecule in its intact state or may be incorporated into the biomolecule during synthesis or through post translational modification. The functionalization of intact biomolecules to form modified biomolecules as described herein typically occurs by N-hydroxysuccinimide (NHS) mediated amide bond formation with an amine or carboxylic acid functionality on the biomolecule or by substitution of a thiol group on the biomolecule with a maleimide group.

NHS esters are commonly used to functionalize amino groups on biomolecules due to their aqueous compatibility and selectivity for primary amines on lysine residues or at the N-terminus of polypeptides. A representative example of addition of an alkynyl group using an NHS ester is provided in Scheme 12 below:

Scheme 12

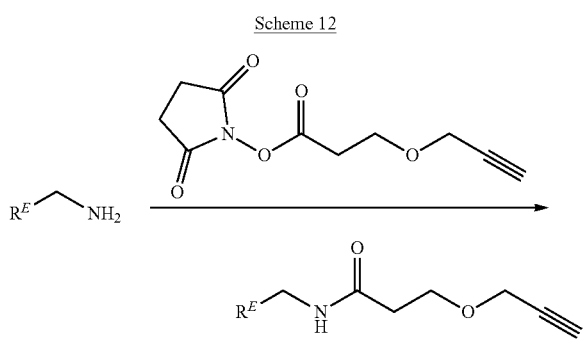

wherein $R^E$ is the biomolecule or a modified derivative thereof. In the absence of amino groups, other functional groups such as alcohols and thiols may alternatively be modified.

Alternatively, carboxylic acid functional groups on the biomolecule can be functionalized via in situ formation of the NHS ester by reaction with NHS and a coupling reagent (for example DCC or EDC) followed by subsequent reaction with an amino-substituted alkyne reagent. A representative example of this type of reaction is provided in Scheme 13 below:

Scheme 13

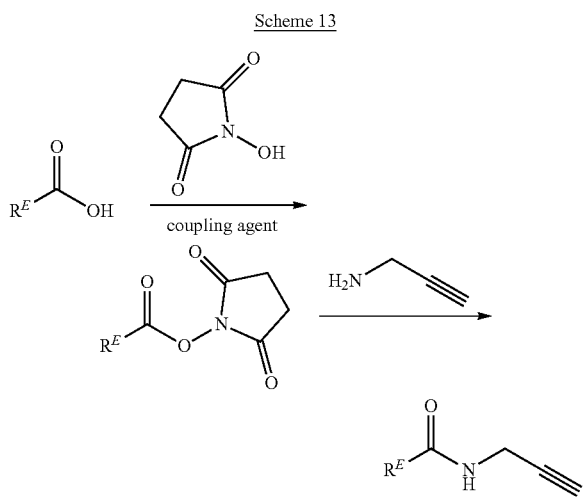

wherein $R^E$ is the biomolecule or a modified derivative thereof. Functionalization reactions involving NHS esters can be run in aqueous buffers at a pH of 7 to 9 for larger biomolecules, but may be run in organic solvents for smaller biomolecules that do not require aqueous solvation. The use of amine-containing buffers such as tris or glycine should be avoided except to quench the functionalization reaction upon completion. Additional details about using NHS esters to functionalize biomolecules can be found in Chan, A. O. et al. Journal of the American Chemical Society 2012, 134, 2589-2598, incorporated herein by reference in its entirety.

Thiol groups present on biomolecules, for example cysteine residues, may be functionalized with an alkyne group by reaction with a substituted maleimide reagent. A representative example of this type of functionalization is provided in Scheme 14 below:

Scheme 14

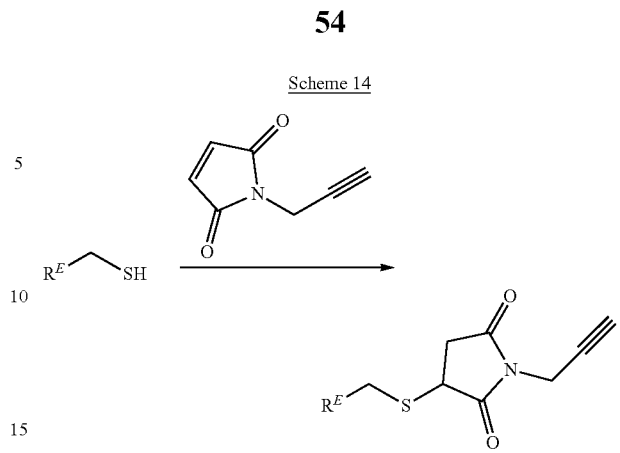

wherein $R^E$ is the biomolecule or a modified derivative thereof. Functionalization reactions involving NHS esters can be run in aqueous buffers at pH 6 to 8. At lower pH values, the reaction tends to be slower but to produce more of the thioether product, while at higher pH values the reaction proceeds faster but with higher levels of hydrolysis of the formed product. The use of thiol-containing buffers such as dithiothreitol (DTT) and beta-mercaptoethanol (BME) should be avoided when using this functionalization procedure. Additional details about using maleimides to functionalize biomolecules can be found in: Fontaine, S. D. et al: Bioconjugate Chemistry 2015, 26, 145-152; and Northrup, B. H. et al. Polymer Chemistry 2015, 6, 3415-3430; each of which is incorporated herein by reference in its entirety.

In some embodiments, the alkyne functional group may be incorporated into the sequence of a polypeptide by using an unnatural amino acid (UNA) that contains the alkyne functional group. The alkyne functional group may be placed via site-specific functionalization, wherein a single amino acid in the polypeptide contains the modification, or by residue-specific functionalization, wherein a particular amino acid is replaced quantitatively throughout the polypeptide. Additional details about using UAAs to functionalize biomolecules can be found in: Kim, S. et al. Bioorganic and Medicinal Chemistry 2016, 24, 5816-5822; Maza., J. C. et al. Bioconjugate Chemistry 2015, 26, 1884-1889; Zimmerman, E. S. et al. Bioconjugate Chemistry 2014, 25, 351-361; and Swiderska, K, W. et al. Bioorganic and Medicinal Chemistry 2017, 25, 3685-369:3; each of which is herein incorporated by reference in its entirety.

Site-specific functionalization is typically used for small polypeptides using solid phase peptide synthesis. Representative examples of UAAs that may be used during solid phase peptide synthesis to incorporate an alkyne functional group include:

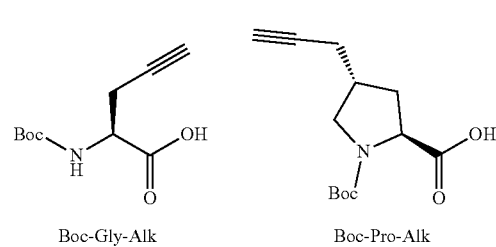 [SMILES: C#CC[C@H](NC(=O)OC(C)(C)C)C(=O)O ; C#CC[C@@H]1C[C@@H](C(=O)O)N(C(=O)OC(C)(C)C)C1]

Boc-Gly-Alk          Boc-Pro-Alk

Additional details regarding the incorporation of UAAs into a biomolecule using solid phase peptide synthesis can be found in: Mulder, G. E, et al. Chemical Communications 2012, 48, 10007-10009; Das, S. et al. Angewandte Chemie International Edition 2015, 54, 13219-13224; Empting, M. et al. Angewandie Chemie International Edition 2011, 50, 5207-5211; van Maarseveen, J. H. et al. Organic Letters 2005, 7, 4503-4506; Torres, 0. et al. ChemBioChem 2008, 9, 1701-1705; Lim, S. I. et al. Journal of Controlled Release 2013, 170, 219-223; VanBrunt, M. P. et al. Bioconjugate Chemistry 2015, 26, 2249-2260; each of which is incorporated herein by reference in its entirety.

Alternatively, site-specific functionalization can be used for polypeptides that cannot be formed using solid phase peptide synthesis by using an engineered tRNA unique for the target codon in the polypeptide's mRNA sequence. For residue-specific functionalization, UAAs are included in cell growth medium and incorporated into the primary sequence of the expressed polypeptide. Residue-specific functionalization tends to provide heterogeneous incorporation of the UAAs that may result in altered physical and chemical properties of the polypeptide. Representative examples of UAAs that may be used in these approaches to incorporate an alkyne functional group include:

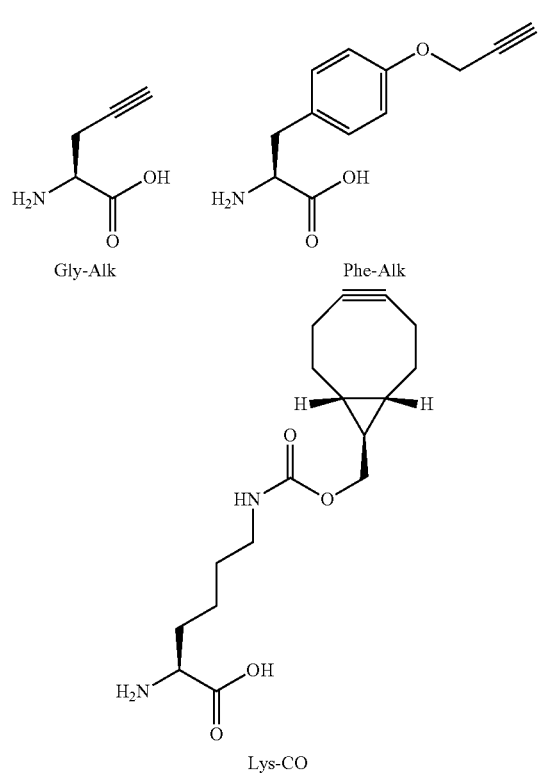

Gly-Alk    Phe-Alk

Lys-CO

Additional details regarding residue-specific functionalization can be found in: Budisa, N. Angewandte Chemie International Edition 2004, 43, 6426-6463; and Johnson, J. A. et al. Current Opinion in Chemical .Biology 2010, 14, 774-780; each of which is incorporated herein by reference in its entirety.

If no alterations of the amino acid residues in the polypeptide sequence can be made without detriment to critical side chain interactions, a heterobifunctional linker containing the alkyne functionality and either a carboxylic acid or amine moiety may be placed on either the N-terminus or C-terminus of the peptide, respectively, as the final step of solid phase peptide synthesis. Representative example heterobifunctional linkers that may be used in this type of approach include:

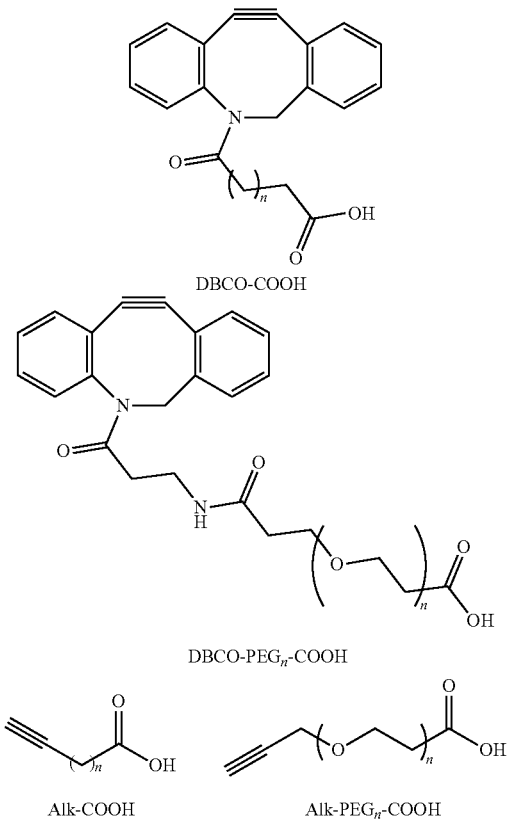

DBCO-COOH

DBCO-PEG$_n$-COOH

Alk-COOH    Alk-PEG$_n$-COOH

Additional examples of the use of heterobifunctional linkers as described above in bioconjugation include: Sola, L. et al. Langmuir 2016, 32, 10284-10295; Bayramoglu, G. et al, Industrial & Engineering Chemistry Research 2014, 53, 4554-4564; Ciao, Y. et al. Industrial & Engineering Chemistry Research 2014, 53, 16777-16784; Hartwell, B. L. et al. Biomacromolecules 2017, 18, 1893-1907; Nuhn. L. et al. Angewandte Chemie International Edition 2013, 52, 10652-10656; Gori, A. et al. Bioconjugate Chemistry 2016, 27, 2669-2677; Goswami, L. N. et al. Organic & Biomolecular Chemistry 2013, 11, 1116-1126; Gong, H. et al. Bioconjugate Chemisny 2016, 27, 217-225; van Geel, R. et al. Bioconjugate Chemistry 2015, 26, 2233-2242; and Anami, Y. et al. Organic & Biomolecular Chemistry 2017, 15, 5635-5642; each of which is incorporated herein by reference in its entirety.

If the polypeptide of interest is expressed within cells, post-translational modifications that contain an alkyne functional group can be used. The post translational modification may comprise an alkyne-containing modified sugar, modified lipid, or modified isoprenoid derivative. For example, an acetylated modified sugar may be added to growth medium, and subsequent to internalization, nonspecific hydrolases and esterases remove the acetate groups and release the modified sugar bearing the alkyne group. The modified sugar may subsequently glycosylate proteins of interest, allowing for later conjugation. Representative examples of modified sugars containing alkyne groups that may be used for post-translational modifications include:

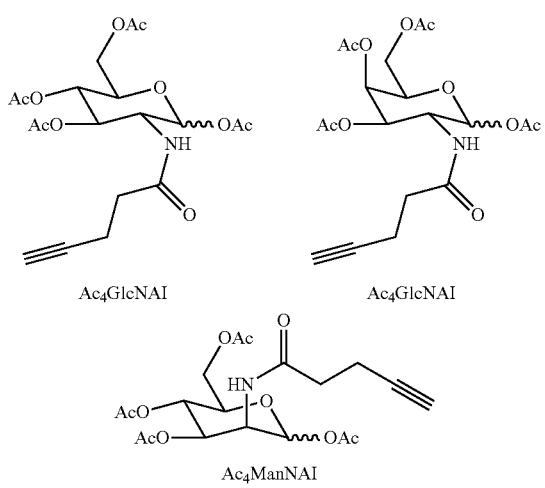

Ac4GlcNAI  Ac4GlcNAI

Ac4ManNAI

Representative examples of modified lipids or isoprenoids containing alkyne groups that may be used for post-translational modifications include:

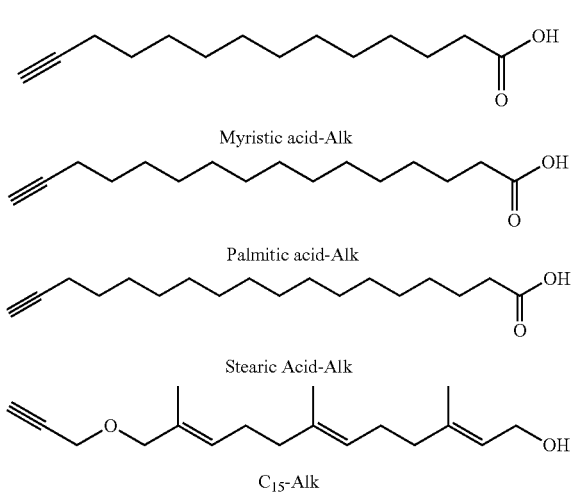

Myristic acid-Alk

Palmitic acid-Alk

Stearic Acid-Alk $C_{15}$-Alk

Additional details regarding the use of post-translational modification to introduce functionality for bioconjugation can be found in: Wang, H. et al. Natural Chemical Biology 2017, 13, 415-424; Yoon, H. I. et al. Bioconjugate Chemistry 2016, 27, 927-936; Besancey-Webler, C. et al, Bioorganic & Medicinal Chemistry Letters 2011, 21, 4989-4992; Dehnert, K. W, et al. ACS Chemical Biology 2011, 6, 547-552; Hart, C. et al. Methods in Molecular Biology 2011, 698, 459-484; Zaro, B. W. et al. PNAS 2011, 108, 8146-8151; Rangan, K. J. et al. Journal of the American Chemical Society 2010, 132, 10628-10629; Martin, B. R. et al. Nature Methods 2009, 6, 135-138; Wilson, J. P. et al. Molecular & Cellular Proteomics 2011, 10, M110.001198; Kho, Y. et al. PNAS 2004, 101, 12479-12484; Yount, J. S. et al. Natural Chemical Biology 2010, 6, 610-614; Martin, B. R. et al. Nature Methods 2011, 9, 84-89; Palsuledesai, C. C. et al. ACS Chemical Biology 2016, 11, 2820-2828; Degraw, A. J. et al. Chemical Biology & Drug Design 2010, 76, 460-471; and Charron, G. et al. Molecular BioSystems 2011, 7, 67-73; each of which is incorporated herein by reference in its entirety.

In other embodiments, alkyne modified nucleic acids or membrane components may be used to install a reactive handle in actively synthesized DNA, RNA, or cell membranes within a cell. Some representative examples of modified nucleotides that may be incorporated into polynucleotides for bioconjugation include:

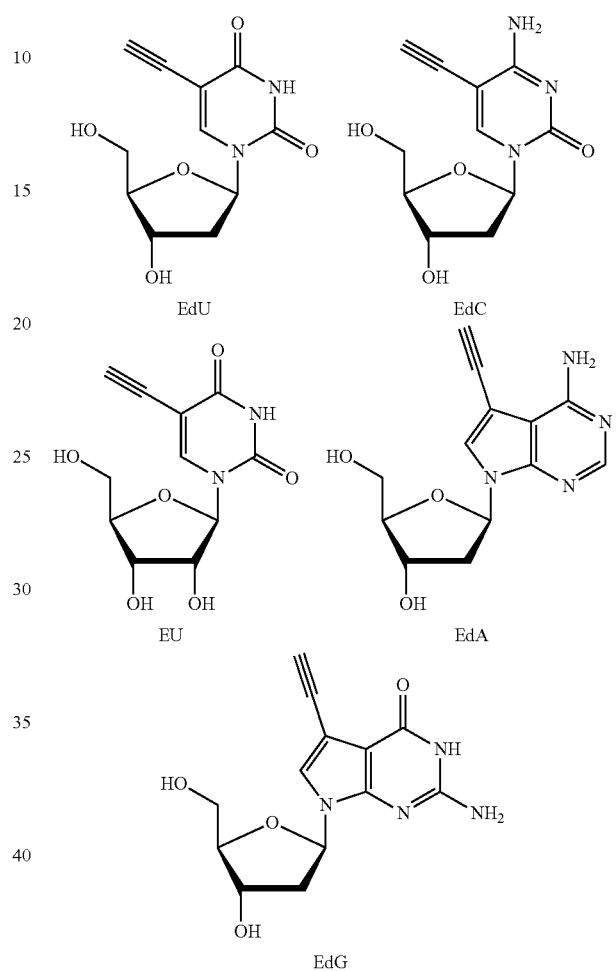

EdU  EdC

EU  EdA

EdG

A representative example of a modified phospholipid precursor that may be used for cell membrane bioconjugation includes:

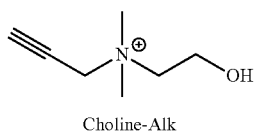

Choline-Alk

Additional details regarding the use of modified nucleotides or membrane components for bioconjugation can be found in: Neef, A. B. et al. ChemBioChem 2012, 13, 1750-1753; Marks, S. I. et al, Bioconjugate Chemistry 2011, 22, 1259-1263; Winz, M. L. et al. Nucleic Acids Research 2015, 43, e110; Sawant, A. A. et al. Nucleic Acids Research 2016, 44, e16; Jao, C. Y. et al. PNAS 2009, 106, 15332-15337; and Taskova, M. et al. Bioconjugate Chemistry 2017, 28, 768-774; each of which is incorporated herein by reference in its entirety.

Additional strategies for bioconjugation and its use in biological applications as can be used in the present invention are described in: Taskova, V. et al. Bioconjugate Chemistry 2017, 28, 768-774; Kim, S. et al. Bioorganic & Medicinal Chemistry 2016, 24, 5816-5822; Kirshenhaum, K. et al. ChemBioChem 2002, 3, 235-237; Laughlin, S. T. and Bertozzi, C. R. PNAS 2009, 106, 12-17; Zheng, T. et al. Angewandte Chemie 2011, 123, 4199-4204; Li, X, et al. Angewandte Chemie International Edition 2014, 53, 7179-7182; Zeglis, B. M. et al. Bioconjugate Chemistry 2013, 24, 1057-1067; Kim, a W. et al. Journal of Fluorine Chemistry 2015, 28, 142-147; Kulkarni, C. et al. Bioconju,gate Chemistry 2017, 28, 1041-1047; Puthenveetil, S. et al. Bioconnigate Chemistry 2016, 27, 1030-1039; and Lee, M. T. et al. Chemical Science 2017 8, 2056-2060; each of which is incorporated herein by reference in its entirety.

EXPERIMENTAL EXAMPLES OF THE PRESENT INVENTION

General Procedures

All reactions were performed in oven-dried or flame-dried round-bottom flasks and vials.

Stainless steel syringes and cannula were used to transfer air- and moisture-sensitive liquids. Flash chromatography was performed using silica gel 60 (230-400 mesh) from Sigma-Aldrich.

Materials

Commercial reagents were purchased from Sigma-Aldrich, Fluka, EM Science, and Lancaster and used as received. All solvents were used after being freshly distilled unless otherwise noted.

Instrumentation

Proton nuclear magnetic resonance ($^1$H NMR) spectra and carbon nuclear magnetic resonance ($^{13}$C NMR) spectra were recorded on a Bruker UltraShield-400 (400 MHz) nuclear magnetic resonance spectrometer. Chemical shifts for protons are reported in parts per million downfield from tetramethylsilane and are referenced to the NMR solvent residual peak (CHCl$_3$ δ 7.26). Chemical shifts for carbons are reported in parts per million downfield from tetramethylsilane and are referenced to the carbon resonances of the NMR solvent (CDCl$_3$ δ 77.0). Data are represented as follows: chemical shift, multiplicity (br=broad, s=singlet, d=doublet, t=triplet, q=quartet, m=multiple° , coupling constants in Hertz (Hz), and integration. When $^{19}$F NMR is used for quantitative purpose (dr determination) 30 degrees pulse and a longer delay time (d1=5 s) were employed and the receiver gain was manually set as 32. The mass spectroscopic data were obtained at the Georgia State University mass spectrometry facility using a Micromass Platform II single quadrupole instrument. Infrared (IR) spectra were obtained using a Perkin Elmer Spectrum 100 FT-IR spectrometer. Data are represented as follows: frequency of absorption (cm $^{-1}$) and absorption strength (s=strong, m=medium, w=weak).

Abbreviations

The following abbreviations are used in the synthetic schemes:
Boc$_2$O di-tert-butyl dicarbonate
CH$_2$Cl$_2$ dichloromethane
DCC N,N'-dicyclohexylcarbodiimide
DMAP 4-dimethylaminopyridine
Et$_2$O diethyl ether
EtOAc ethyl acetate
$^i$PR$_2$NH diisopropylamine
MeCN acetonitrile
MeI methyl iodide
MeOH methanol
Ns 4-nitrobenzenesulfonyl
TEA triethylamine
TEMPO 2,2,6,6,-tetramethyl-1-piperidinyloxy
TFa trifluoroacetic acid
THF tetrahydrofuran
TIPS triisopropylsilyl
TLC thin layer chromatography
Troc 2,2,2-trichloroethoxycarbonyL

EXAMPLE 1

Synthesis of 1-Aziododoecane by Procedure 1

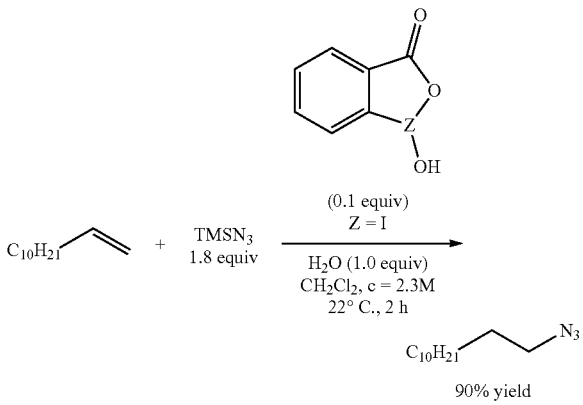

1-Dodecene is commercially available and was distilled before use.

To a flame-dried sealable 2-dram vial equipped with a stir bar were added 1-dodecene (222 µL, 1.0 mmol, 1.0 equiv) and 1-hydroxy-1λ$^3$-benzo[d][1,2]iodaoxol-3(1H)-one (27 mg, 0.1 mmol, 0.1 equiv). After this vial was evacuated and backfilled with N$_2$ twice, anhydrous CH$_2$Cl$_2$ (0.2 mL) and H$_2$O (18 µL, 1.0 mmol, 1.0 equiv) were added via syringes. Freshly opened trimethylsilylazide (237 ∞L, 1.8 mmol, 1.8 equiv) was added to the reaction and the mixture was stirred for 2 h at 22° C. until the olefin was fully consumed (monitored by TLC). The reaction was cooled to 0° C., Hexanes (2 mL) and saturated NaHCO$_3$ solution (1.5 mL) were added to quench the reaction and to neutralize the residual hydrazoic acid. The organic phase was separated from the aqueous phase, and the aqueous phase was extracted with hexanes (3 mL×3). The combined organic phase was washed with brine (2 mL) and dried over Na$_2$SO$_4$. After concentration in vacuo, the residue was purified through column chromatography (100% hexanes) to afford 1-azidododecane as colorless oil (190 mg, 90% yield) which is a known compound (see Hays, D.S. et al The Journal of Organic Chemistry 1998, 63, 2796).

EXAMPLE 2

Synthesis of 1-Azidododecane by Procedure 2

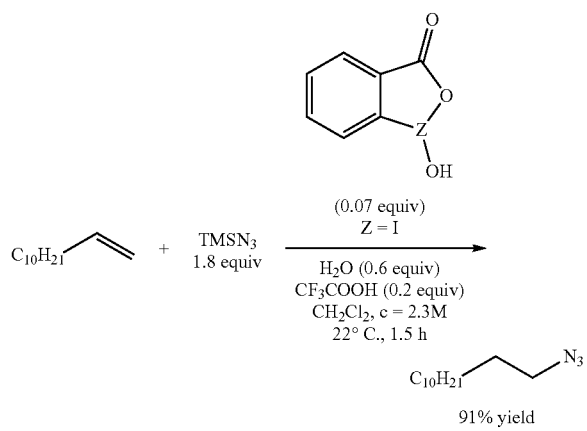

To a flame-dried sealable 2-dram vial equipped with a stir bar were added 1-dodecene (222 μL, 1.0 mmol, 1,0 equiv) and 1-hydroxy-1λ³-benzo[a][1,2]iodaoxol-3(1H)-one (19 mg, 0.07 mmol, 0.07 equiv), After this vial was evacuated and backfilled with $N_2$ twice, anhydrous $CH_2Cl_2$ (0.2 mL) and $H_2O$ (11 μL, 0.6 mmol, 0.6 equiv) were added via syringes. After the vial was cooled to 0° C., freshly distilled trimethylsilylazide (237 μL, 1.8 mmol, 1.8 equiv) was added to the reaction followed by the addition of trifluoroacetic acid (TFA) (15 μL, 0.2 mmol, 0.2 equiv). The mixture was warmed up to 22° C. and kept stirring for 1.5 h until the olefin was fully consumed (monitored by TLC). The reaction was cooled to 0° C., hexanes (2 mL) and saturated $NaHCO_3$ solution (1.5 mL) were added to quench the reaction and to neutralize the residual hydrazoic acid. The organic phase was separated from the aqueous phase, and the aqueous phase was extracted with hexanes (3 mL×3). The combined organic phase was washed with brine (2 mL) and dried over $Na_2SO_4$. After concentration in vacuo, the residue was purified through column chromatography (100% hexanes) to afford 1-azidododecane as colorless oil (192 mg, 91% yield).

EXAMPLE 3

Synthesis of 1-Azidododecane by Procedure 3

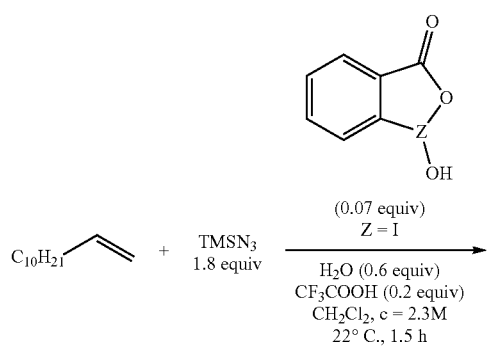

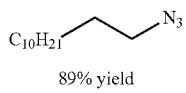

To a flame-dried sealable 2-dram vial equipped with a stir bar were added 1-dodecene (222 μL, 1.0 mmol, 1,0 equiv) and 1-hydroxy-1λ³-benzo[d][1,2]iodaoxol-3(1H)-one (19 mg, 0.07 mmol, 0.07 equiv). After this vial was evacuated and backfilled with $N_2$ twice, anhydrous $CH_2Cl_2$ (0.2 mL) and trifluoroacetic acid (15 μL, 0.2 mmol, 0.2 equiv) were added via syringes and the mixture was stirred at room temperature for 5 min. During this time, the solution first became homogenous, and then white precipitates formed. $H_2O$ (11 μL, 0.6 mmol, 0.6 equiv) and trimethylsilylazide (239 μL, 1.8 mmol, 1.8 equiv) were added to the reaction and the mixture was stirred at room temperature for 1.5 h until the olefin was fully consumed (monitored by TLC). The reaction was cooled to 0° C. Hexanes (2 mL) and saturated $NaHCO_3$ solution (1.5 mL) were added to quench the reaction and to neutralize the residual hydrazoic acid. The organic phase was separated from the aqueous phase, and the aqueous phase was extracted with hexanes (3 mL×3). The combined organic phase was washed with brine (2 mL) and dried over $Na_2SO_4$. After concentration in mew), the residue was purified through column chromatography (100% hexanes) to afford 1-azidododecane as colorless oil (189 mg, 89% yield).

EXMAPLE 4

Synthesis of 3-Oxo-1λ³-benzo[d][1,2]iodaoxol-1 (3H)-yl2,2,2-trifluoroacetate

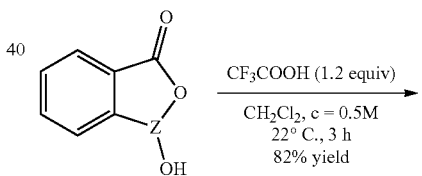

To a flame-dried flask (25 mL) equipped with a stir bar was added 1-hydroxy-1λ³-benzo[d][1,2]iodaoxol-3(1H)-one (1.0 g, 3.8 mmol, 1.0 equiv). After the flask was evacuated and backfilled with $N_2$ twice, anhydrous $CH_2Cl_2$ (7.6 mL) was added, followed by the addition of trifluoroacetic acid (TFA) (0.35 mL, 4.55 mmol, 1.2 equiv) via syringe. The reaction was stirred for 3 h at 22° C., during this period, the mixture first became homogenous, and then white precipitates formed. After stirred for 3 h, the precipitate was filtered and washed with $CH_2Cl_2$ (5 mL×2), then dried in in vacuo to afford 3-oxo-1λ³-benzo[d][1,2]iodaoxol-1(3H)-yl 2,2,2-trifluoroacetate as a white solid (1.12 g, 82% yield, m.p. 212-214° C.).

IR $\nu_{max}$ (neat)/cm$^{-1}$: 3115 (w), 3092 (w), 3066 (w), 1705 (s), 1671 (s), 1589 (m), 1570 (m), 1463 (m), 1443 (m), 1385 (s), 1279 (s), 1244 (s), 1168 (s), 1144 (s), 1108 (s), 856 (s), 826 (s), 780 (s), 753 (s), 731 (s), 696 (m); $^1$H NMR (400 MHz, CD$_3$OD) δ 6 8.16 (dd, J=7.6, 1.4 Hz, 1H), 8.03-7.95 (m, 1H), 7,87 (d, J=7.8 Hz, 1H), 7.74 (td, J=7.5, 0.9 Hz, 1H); $^{13}$C NMR (100 MHz, CD$_3$OD) δ 170.2, 158.3 (q, J=40.1 Hz), 135.1, 131.8, 130.6, 130.5, 126.3, 118.9, 112.3 (q, J=285.0 Hz); $^{19}$F NMR (376 MHz, CD$_3$OD) 6-77.76.

EXAMPLE 5

Synthesis of 1-Azidododecane Using Catalytic 3-Oxo-1λ$^3$-benzo[d][1,2]iodnoxol-1(3H)-yl2,2,2-trifluoroacetate

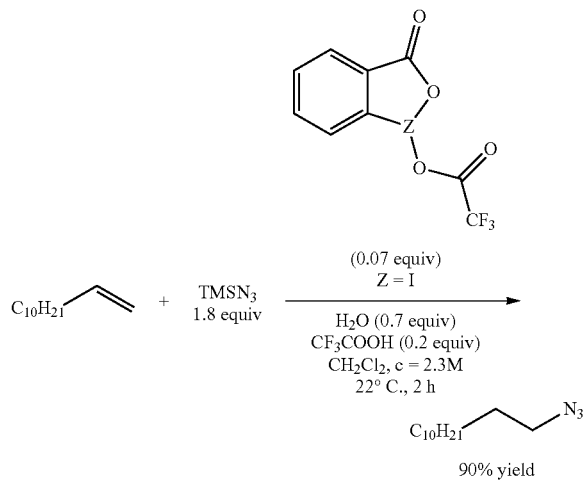

To a flame-dried sealable 2-dram vial equipped with a stir bar were added 1-dodecene (222 μL, 1.0 mmol, 1.0 equiv) and 3-oxo-1λ$^3$-benzo[d][1,2]iodaoxol-1(3H)-yl2,2,2-trifluoroacetate (25 mg, 0.07 mmol, 0.07 equiv). After this vial was evacuated and backfilled with N$_2$ twice, anhydrous CH$_2$Cl$_2$ (0.2 mL) and H$_2$O (13 μL, 0.7 mmol, 0.7 equiv) were added via syringes. After the vial was cooled to 0° C., freshly distilled trimethylsilylazide (237 μL, 1.8 mmol, 1.8 equiv) was added to the reaction followed by the addition of trifluoroacetic acid (15 μL, 0.2 mmol, 0.2 equiv). The mixture was warmed up to 22° C. and kept stirring for 2 h until the olefin was fully consumed (monitored by TLC). The reaction was cooled to 0° C., Hexanes (2 mL) and saturated NaHCO$_3$ solution (1.5 mL) were added to quench the reaction and to neutralize the residual hydrazoic acid. The organic phase was separated from the aqueous phase, and the aqueous phase was extracted with hexanes (3 mL×3). The combined organic phase was washed with brine (2 mL) and dried over Na$_2$SO$_4$. After concentration in vacuo, the residue was purified through column chromatography (100% hexanes) to afford 1-azidododeca.ne as colorless oil (190 mg, 90% yield).

EXAMPLE 6

Synthesis of 1-Azido-2-methyhlonane

2-Methylnon-l-ene is commercially available and was distilled before use.

The reaction was carried out on a 1.0 mmol scale and Procedure 1 of Example 1 was applied. The crude product was purified through column chromatography (100% hexanes) to afford the desired product 1-azido-2-methyl-nona.ne as a colorless oil (161 mg, 88% yield).

IR $\nu_{max}$ (neat)/cm$^{-1}$: 2958 (m), 2925 (s), 2856 (m), 2094 (s), 1460 (m), 1380 (m), 1272 (s), 723 (w); $^1$H NMR (400 MHz, CDCl$_3$) δ 3.21 (dd, J=12.0, 5.9 Hz, 1H), 3.09 (dd, J=12.0, 7.0 Hz, 1H), 1.76-1.63 (m, 1H), 1.42-119 (m, 12H), 0.95 (d, J=6.7 Hz, 3H), 0.89 (t, J=6.8 Hz, 3H); $^{13}$C NMR (100 MHz, CDCl$_3$) δ 57.9, 34.1, 33.5, 31.8, 29.7, 29.2, 26.8, 22.7, 17.7, 14.1; LRMS: m/z (EI) calcd for C$_{10}$H$_{21}$N$^+$, [M−N$_2$]$^+$, 155.2, found 155.2.

EXAMPLE 7

Synthesis of 4-Azidooctane (E)-Oct-4-ene is commercially available and was distilled before use.

The reaction was carried out on a 1.0 mmol scale. Procedure 2 of Example 2 was applied with several modifications: 0.2 equiv of 1-hydroxy-1λ³-benzo[d][1,2]iodaoxol-3(1H)-one and 2.0 equiv of trimethylsilylazide were used; and the reaction was set up at 0° C. and slowly warmed to 22° C. over 0.5 h, then was kept stirring for another 2 h at 22° C. The crude product was purified through column chromatography (100% hexanes) to afford 4-azidooctane as a colorless oil (110 mg, 71% yield).

IR $v_{max}$ (neat)/cm$^{-1}$: 2960 (s), 2934 (s), 2874 (m), 2093 (s), 1466 (m), 1252 (s), 1119 (w), 950 (w), 719 (m); $^1$H NMR (400 MHz, CDCl$_3$) δ 3.37-3.07 (m, 1H), 1.61-1.39 (m, 5H), 1.38-1.21 (m, 5H), 0.99-0.84 (m, 6H); $^{13}$C NMR (100 MHz, CDCl$_3$) δ 62.8, 36.5, 34.1, 28.3, 22.5, 19.3, 13.9, 13.8; LRMS: m/z (EI) calcd for C$_8$H$_{17}$N$^+$, [M−N$_2$]$^+$, 127.1, found 127.1.

EXAMPLE 8

Synthesis of 2-Azidooctane and 3-Azidooctane

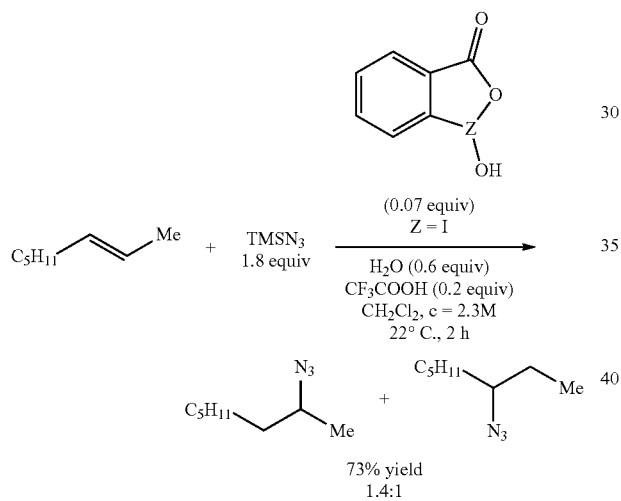

73% yield
1.4:1

(E)-Oct-2-ene is commercially available and was distilled before use.

The reaction was carried out on a 1,0 mmol scale and Procedure 2 of Example 2 was applied.

The crude product was purified through column chromatography (100% hexanes) to afford a 1.4:1 mixture of 2-azidooctane and 3-azidooctane as a colorless oil (113 mg, 73% yield).

IR $v_{max}$ (neat)/cm$^{-1}$: 2959 (m) 2931 (s), 2859 (m), 2093 (s), 1458 (m), 1380 (m), 1248 (s), 1050 (w), 902 (w), 726 (w); 2-Azidooctane: $^1$H NMR (400 MHz, CDCl$_3$) δ 3.49-3.31 (m, 1H), 1.68-1.26 (m, 10H), 1.23 (d, J=6,5 Hz, 3H), 0.92-0.80 (m, 3H); $^{13}$C NMR (100 MHz, CDCl$_3$) δ 58.0, 36.2, 31.7, 29.0, 26.0, 22.5, 19.4, 14.0; 3-Azidooctane: $^1$H NMR (400 MHz, CDCl$_3$) δ 3.27-3.06 (m, 1H), 1.68-1.26 (m, 10H), 0.97 (t, J=7.4 Hz, 3H), 0.92-0.80 (m, 3H ); $^{13}$C NMR (100 MHz, CDCl$_3$) δ 64.6, 33.9, 31.6, 27.4, 25.8, 22.5, 13.9, 10.4; LRMS: m/z (EI) calcd for C$_8$H17N$^+$, [M−N$_2$]$^+$, 127.1, found 127.1.

EXAMPLE 9

Synthesis of 2-Azidobicyclo[2.2.1]heptane

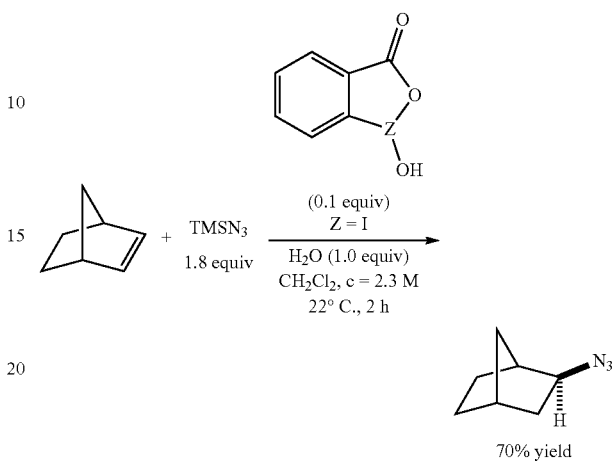

70% yield

Bicyclo[2.2.1]hept-2-ene is commercially available and was used directly without further purification.

The reaction was carried out on a 1.0 mmol scale and Procedure 1 of Example 1 was applied. The crude product was purified through column chromatography (100% hexanes) to afford 2-azidobicyclo[2.2.1]heptane as a colorless oil (96 mg, 70% yield) which is a known compound) see Breton, G. W. et al. The Journal of Organic Chemistry 1992, 57, 6646).

EXAMPLE 10

Synthesis of (1,R,3,S,4S)-3-(Azidomethyl)-2,2-dimethylbicyclo[2.2.1]heptane

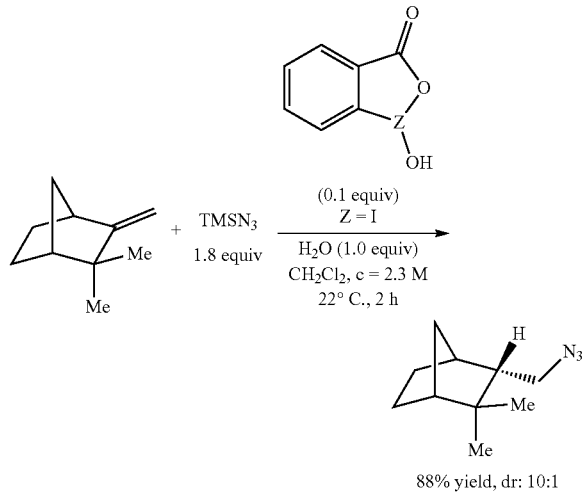

88% yield, dr: 10:1

(+)-Camphene is commercially available and was used directly without further purification.

The reaction was carried out on a 1.0 mmol scale and Procedure 1 of Example 1 was applied. The crude product was purified through column chromatography (100% hexanes) to afford (1R,3S,4S)-3-(azidomethyl)-2,2-dimethylbicyclo[2.2.1]heptane as a colorless oil (158 mg, 88% yield, dr:10:1).

IR $\nu_{max}$ (neat)/cm$^{-1}$: 2955 (s), 2879 (m), 2086 (s), 1464 (m), 1366 (m), 1264 (s), 1116 (w), 895 (m); $^1$H NMR (400 MHz, CDCl$_3$) δ 3.2.5 (d, J=8.2 Hz, 2H), 2.26 (s, 1H), 1.77 (s, 1.66 (dt, J=12.1, 3.8 Hz, 2H), 1.60-1.47 (m, 1H), 1.39-1.25 (m, 3H), 1.22 (d, J=9.9 Hz, 1H), 1.00 (s, 3H), 0.85 (s, 3H); $^{13}$C NMR (100 MHz, CDCl$_3$) δ 50.0, 49.5, 49.0, 40.7, 37.0 (2 carbon merged), 32.2, 24.5, 20.7, 20.2; LRMS: m/z (EI) calcd for C$_{10}$H$_{17}$N$^+$, [M−N$_2$]$^+$, 151.1, found 151.1.

The relative stereochemistry was determined by X-ray crystallographic analysis of N-(((1S,2S,4R)-3,3-dimethylbicyclo[2.2.1]heptan-2-yl)methyl)-4-nitrobenzenesulfonamide synthesized by the procedure below:

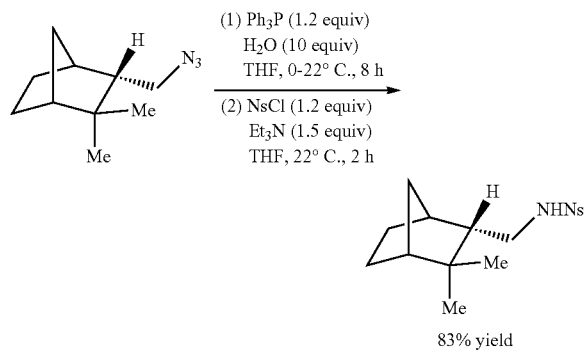

83% yield

To a flask (25 mL) equipped with a stir bar was added (1R,3S,4S)-3-(azidomethyl)-2,2-dimethylbicyclo[2.2.1]heptane (150 mg, 0.84 mmol, 1.0 equiv), H$_2$O (0.15 mL, 8.37 mmol, 10 equiv) and TELF (6 mL). After the flask was evacuated and backfilled twice with N$_2$, a solution of triphenylphosphine (262 mg, 1.0 mmol, 1.2 equiv) in THF (2. mL) was added drop-wise at 0 ° C. The mixture was warmed up to 22° C. and stirred for 8 h (monitored by TLC until the azide starting material was fully consumed). Subsequently, 4-nitrobenzenesulfonyl chloride (222 mg, 1.0 mmol, 1.2 equiv) in THF (5 mL) and Et$_3$N (0.17 mL, 1.26 mmol, 1.5 equiv) were added to the above mixture drop-wise at 0° C. The resulting solution was warmed up to room temperature and kept stirring for additional 2 h. After concentration iii veno, the residue was purified through column chromatography (hexanes/EtOAc: from 50:1 to 6:1) to afford N-(((1S, 2S,4R-3,3-dimethylbicyclo[2.2.1]heptan-2-yl)methyl)-4-nitrobenzenesulfonamide as a white solid (235 mg, 83% yield, m.p. 125-127° C.).

IR $\nu_{max}$ (neat)/cm$^{-1}$: 3292 (m), 3108 (w), 2956 (m), 2876 (m), 1529 (s), 1348 (s), 1162 (s), 1094 (m), 853 (m), 735 (s), 686 (m); $^1$H NMR (400 MHz, CDCl$_3$) δ 8.38 (d, J=8.8 Hz, 2H), 8.06 (d, J=8.8 Hz, 2H), 4.34 (t, J=5.7 Hz, 1H), 3.02 (dt, J=12.3. 6.2 Hz, 1H), 2.92 (ddd, J=12.2, 10.1, 5.6 Hz, 1H), 2.12 (s, 1H), 1.75 (s, 1H), 1.61-1.45 (m, 3H), 1.35-1.15 (m, 3H), 1.15-1.02 (m, 1H), 0.94 (s, 3H), 0.78 (s, 3H); $^{13}$C NMR (100 MHZ, CDCl$_3$) δ 150.0, 145.8, 128.3, 124.4, 49.9, 48.9, 41.5, 40.0, 37.0, 36.8, 32.3, 24.3, 20.7, 19.9; HRMS (ESI, m/z): calcd for C$_{16}$H$_{22}$N$_2$O$_4$SNa$^+$, [M+Na$^+$], 361.1192, found 361.1190.

N-(((1S,2S,4R)-3,3-Dimethylbicyclo[2.2.1]heptan-2-yl) methyl)-4-nitrobenzenesulfonamide was recrystallized from EtOAc/hexanes and analyzed by X-ray crystallography.

EXAMPLE 11

Synthesis of Azidocyclooctane

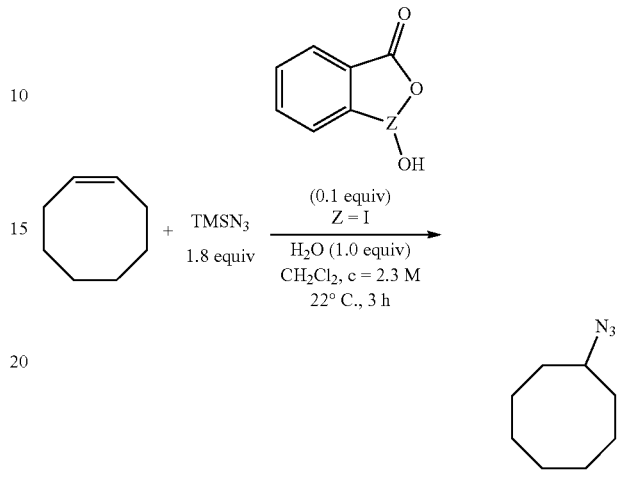

70 yield (Z)-Cyclooctene is commercially available was distilled before use.

The reaction was carried out on a 1.0 mmol scale and Procedure 1 of Example 1 was applied. The crude product was purified through column chromatography (100% hexanes) to afford the azidocyclooctane as a colorless oil (107 mg, 70% yield) which is a known compound (see Waser, J., et al. Journal of the American Chemical Society 2006, 128, 11693).

EXAMPLE 12

Synthesis of (3-Azidopropyl)benzene and (2-Azidopropyl)benzene

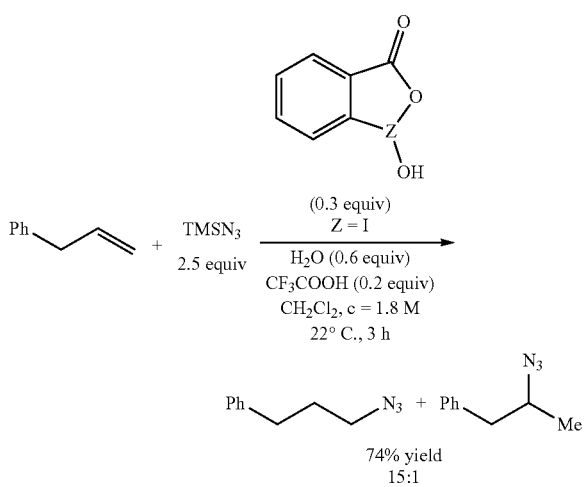

74% yield
15:1

Allybenzene is commercially available and was distilled before use.

The reaction was carried out on a 1.0 mmol scale. Procedure 2 of Example 2 was applied with some modifications: 0.3 equiv of 1-hydroxy-1λ³-benzo[d][1,2]iodaoxol-3(1H)-one and 2.5 equiv of trimethylsilylazide were used. The crude product was purified through column chromatography (100% hexanes) to afford a 15:1 mixture of (3-azidopropyl)benzene and (2-azidopropyl)benzene as a colorless oil (119 mg, 74% yield) which are known compounds (see Ngai, M. H. et al. Chemical Communications 2010, 46, 8335; Zhu, Y. et al. Organic Letters 2015, 17, 4702).

The structure was additionally confirmed by $^1$H and $^{13}$C NMR analysis of its derivatives N-(3-phenylpropyl)acetamide and N-(1-phenylpropan-2-yl)acetamide synthesized by the procedure below:

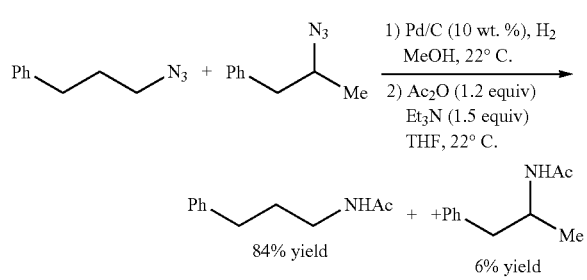

To a 25 mL 2-neck round bottom flask equipped with a stir bar and a three-way adapter was added Pd/C (32 mg, 10 wt. %). After the flask was evacuated and backfilled twice with $N_2$, a solution of the mixture of (3-azidopropyl)benzene and (2-azidopropyl)benzene (322 mg, 2.0 mmol, 1.0 equiv) in MeOH (10 mL) was added. The mixture was degassed with brief evacuation and backfilled three times with $H_2$, and then vigorously stirred under $H_2$ balloon at 22° C. for 5 h (monitored by TLC until the azide starting material was fully consumed). The solution was filtered through a Celite pad and washed with MeOH (10 mL). The combined filtrates were concentrated to afford the crude amine, which was then dissolved in 15 mL THF. $Ac_2O$ (22.7 μL, 2.4 mmol, 1.2 equiv) and $Et_3N$ (417 μL, 3.0 mmol, 1.5 equiv) were added to the above mixture drop-wise successively at 0° C. The resulting mixture was warmed up to room temperature and kept stirring for additional 2 h until the amine intermediate was fully consumed (monitored by TLC). After concentration in vacuo, the residue was subsequently purified through column chromatography (hexanes/EtOAc: from 20:1 to 2:1) to afford N-(3-phenylpropyl)acetamide as a colorless oil (298 mg, 84% yield) along with N-(1-phenytpropan-2-yl)acetamide as a colorless oil (21 mg, 6% yield).

N-(3-Phenylpropyl)acetamide: IR $v_{max}$ (neat)/cm$^{-1}$: 3284 (w), 1647 (s), 1551 (s), 1496 (m), 1454 (m), 1437 (m), 1368 (m), 1266 (s), 1031 (w), 733 (s), 699 (s); $^1$H NMR. (400 MHz, CDCl$_3$) δ 7.28-7.26 (m, 2H), 7.19-7.16 (m, 3H), 5.44 (s, 1H), 3.28 (dd, J=13.2, 6.9 Hz, 2H), 2.69-2.62 (m, 2H), 1.93 (s, 3H), 1.89-1.79 (m, 2H); $^{13}$C NMR (100 MHz, CDCl$_3$) δ 170.0, 141.4, 128.5, 128.3, 126.0, 39.3, 33.3, 31.2, 23.3; HRMS (EST, m/z): calcd for $C_{11}H_{15}NONa^+$, [M+Na]$^+$, 200.1046, found 200.1042.

N-(1-Phenylpropan-2-yl)acetamide: fit $v_{max}$ neat)/cm$^{-1}$: 3285 (w), 1651 (s), 1549 (m), 1516 (m), 1454 (m), 1373 (m), 1265 (s), 1031 (w), 732 (s), 701 (s); $^1$H NMR (400 MHz, CDCl$_3$) δ 7.39-7.04 (m, 5H), 5.26 (s, 1H), 4.26 (dp, J=13.6, 6.7 Hz, 1H), 2.83 (dd, J=13.5, 5.7 Hz, 1H), 2.72 (dd, J=13.5, 7.2 Hz, 1H), 1.93 (s, 3H), 1.10 (d, J=6.7 Hz, 3H); $^{13}$C NMR (100 MHz, CDCl$_3$) δ169.2, 137.8, 129.5, 128.4, 126.4, 46.0, 42.3, 23.5, 19.9; HRMS (ESI, m/z): calcd for $C_{11}H_{15}NONa^+$, [M+Na]$^+$, 200.1046, found 200.1042.

EXAMPLE 13

Synthesis of (3-Azidopropyl)triisopropylsilane

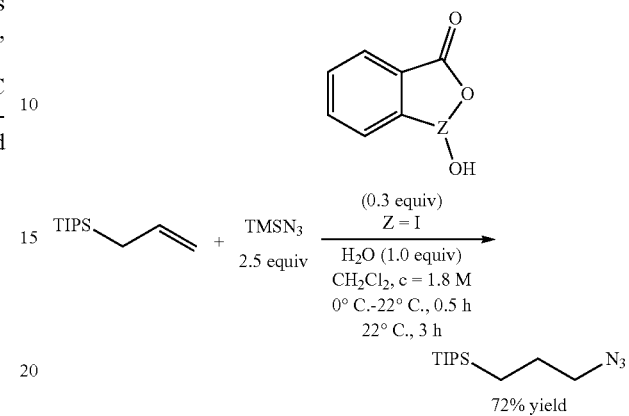

Allyltriisopropylsilane was prepared using a known procedure (see Murakami, K. et al. The Journal of Organic Chemistry 2009, 74, 1415).

The reaction was carried out on a 1.0 mmol scale. Procedure 1 of Example 1 was applied. with several modifications: 0.3 equiv of 1-hydroxy-1λ³-benzo[d][1,2]iodaoxol-3(1H)-one and 2.5 equiv of trimethylsilylazide were used; and the reaction was set up at 0° C. and slowly warmed to 22° C. over 0.5 h, then was kept stifling for another 3 h at 22° C. The crude product was purified through column chromatography (hexanes/EtOAc: from 100:1 to 50:1) to afford (3-azidopropyl)triisopropylsilane as a colorless oil (174 mg, 72% yield).

IR $v_{max}$ (neat)/cm$^{-1}$: 2941 (s), 2891 (m), 2866 (s), 2092 (s), 1462 (m), 1242 (m), 1015 (m), 881 (s), 727 (s), 696 (s); $^1$H NMR (400 MHz, CDCl$_3$) δ 3.24 (t, J=6.9 Hz, 2H), 1.76-1.59 (m, 2H), 1.08-1.04 (m, 21H), 0.65-0.60 (m, 2H); $^{13}$C NMR (100 MHz, CDCl$_3$) δ 55.0, 24.1, 18.8, 10.9, 6.5; LRMS: m/z (EI) calcd for $C_{12}H_{27}NSi^+$, [M–N$_2$]$^+$, 213.2, found 213.2.

EXAMPLE 14

Synthesis of 3-Azidopropyl Benzoate

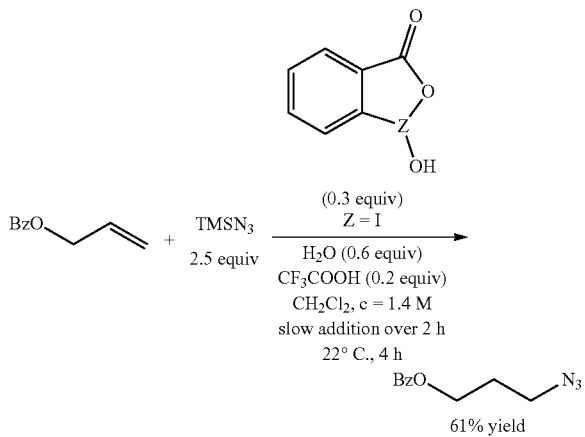

Allyl benzoate was prepared using a known procedure (see Cossy, J. et al. Tetrahedron: Asymmetry 1999, 10, 3859).

The reaction was carried out on a 1.0 mmol scale. Procedure 2 of Example 2 was applied with several modifications: 0.3 equiv of1-hydroxy-1λ³-benzo[d][1,2]iodaoxol-3(1H)-one and 2.5 equiv of trimethylsilylazide were used; and allyl benzoate in CH$_2$Cl$_2$ (0.2 mL) was slowly added to the reaction over 2 h, then was kept stirring for another 2 h at 22° C. The crude product was purified through column chromatography (hexanes/EtOAc: from 100:1 to 10:1) to afford 3-azidopropyl benzoate as a colorless oil (125 mg, 61% yield) which is a known compound (see Baruah, M. and Bols, M. Synlett 2002, 2002, 1111).

EXAMPLE 15

Synthesis of 4-Azidobutyl Benzoate

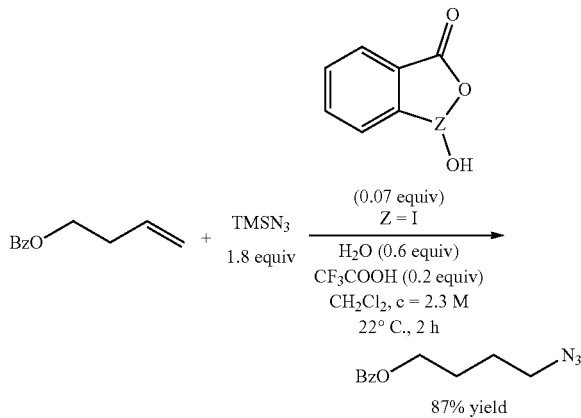

But-3-en-1-yl benzoate was prepared using a known procedure (see Bogen, S. et al. Bioorganix & Medicinal Chemistry Letters 2008, 18, 4219).

The reaction was carried out on a 1.0 mmol scale and Procedure 2 of Example 2 was applied. The crude product was purified through column chromatography (hexanes/EtOAc: 100:1 to 10:1) to afford 4-azidobutyl benzoate as a colorless oil (191 mg, 87% yield) which is a known compound (see Bates, R. W. et al. Organic Letters 2009, 11, 3706).

EXAMPLE 16

Synthesis of 2,2,2-Trichloroethyl (3-Azidopropyl)carbamate and 2,2,2-Trichloroethyl (2-Azidopropyl)carbamate

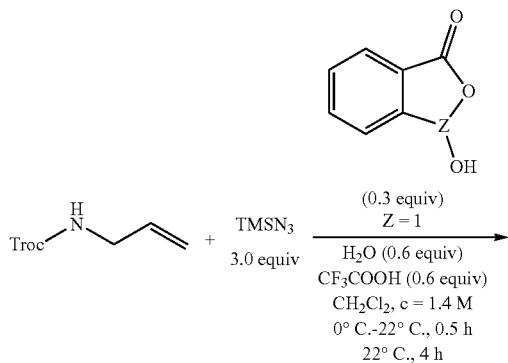

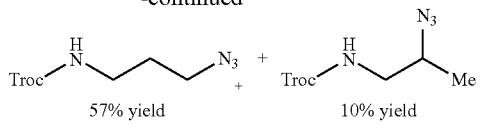

2,2,2-Trichloroethyl allylcarbamate was prepared using a known procedure (see Kazuhiro, M. et al. Bulletin of the Chemical Society of Japan 1987, 60, 1021).

The reaction was carried out on a 1,0 mmol scale. Procedure 2 of Example 2 was applied with several modifications: 0.3 equiv of 1-hydroxy-1λ³-benzo[d][1,2]iodaoxol-3(1H)-one, 3.0 equiv of trimethylsilylazide, and 0.6 equiv of trifluoroacetic acid were used; and the reaction was set up at 0° C., slowly warmed to 22° C. over 0.5 hours, and was kept stirring for another 4 h at 22° C. The crude product was purified through column chromatography (hexanes/EtOAc: from 100:1 to 5:1) to afford 2,2,2-Trichloroethyl (3-Azidopropyl)carbamate as a colorless oil (157 mg, 57%) along with 2,2,2-Trichloroethyl (2-Azidopropyl)carbamate as a colorless oil (28 mg, 10% yield).

2,2,2-Trichloroethyl (3-Azidopropyl)earbamate: IR $v_{max}$ (neat)/cm$^{-1}$: 3337 (br), 2949 (w), 2094 (s), 1712 (s), 1522 (s), 1453 (m), 1240 (s). 1144 (s), 1036 (m), 814 (s), 721 (s); $^1$H NMR (400 MHz, CDCl$_3$, 330 K) δ 5.13 (br s, 1H), 4.72 (s, 2H), 3.38 (t, J=6.5 Hz, 2H), 3.33 (dd, J=13.0, 6.6 Hz, 2H), 1.83 (p, J=6,6 Hz, 2H); $^{13}$C NMR (100 MHz, CDCl$_3$, 298 K) δ 154.6, 95.5. 74.5, 48.9, 38.7, 28.9; HRMS (ESI, m/z): calcd for C$_6$H$_9$Cl$_3$N$_4$O$_2$Na$^+$, [M+Na]$^+$, 296.9683, found 296.9681.

2,2,2-Trichloroethyl (2-Azidopropyl)carbamate: IR $v_{max}$ (neat)/cm$^{-1}$: 3337 (br), 2936 (w), 2113 (s), 1717 (s), 1520 (s), 1453 (m), 1231 (s), 1153 (s), 1025 (m), 812 (s), 722 (s); $^1$H NMR (400 MHz, CDCl$_3$) δ 5.26 (br s, 1H), 4.79-4.67 (m, 2H), 3.78-3.67 (m, 1H), 3.49-3.38 (m, 1H), 3.10 (ddd, J=13.9, 8.0, 5.6 Hz, 1H), 1.30 (d, J=6.6 Hz, 3H); $^{13}$C NMR (100 MHz, CDCl$_3$) δ 154.6, 95.4, 74.6, 57.4, 46.1, 16.7; HRMS (ESI, m/z): calcd for C$_6$H$_9$Cl$_3$N$_4$O$_2$Na$^+$, [M+Na]$^+$, 296.9683, found 296.9681.

EXAMPLE 17

Preparation of 2,2,2-Trichloroethyl Allyl(methyl)carbamate

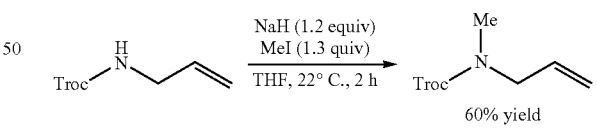

To a flame-dried flask (100 mL) equipped with a stir bar was added 2,2,2-trichloroethyl allylcarbatnate (1.44 g, 6.2 mmol, 1.0 equiv). After flask was evacuated and backfilled with N$_2$ twice, anhydrous THF (40 mL) was added. After the flask was cooled to 0° C., sodium hydride (298 mg, 7.44 mmol, 1.2 equiv, 60% in mineral oil) was added to the solution portion-wise. The reaction mixture was stirred for 30 min at 0° C. before a solution of methyl iodide (0.5 mL, 8.06 mmol, 1.3 equiv) in THF (5 mL) was added via a syringe. The reaction was warmed to 22° C. and kept stirring for 2 h until the starting material was fully consumed (monitored by TLC). EtOAc (15 mL) and saturated NH$_4$Cl solution (10 mL) were added to quench the reaction. The organic phase was separated from the aqueous phase, and the aqueous phase was extracted with EtOAc (20 mL×3). The combined organic phase was washed with brine (20 mL) and dried over $Na_2SO_4$. After concentration in vacuo, the residue was purified through column chromatography (hexanes/EtOAc: from 50:1 to 5:1) to afford 2,2,2-trichloroethyl allyl(methyl)carbamate as yellow oil (917 mg, 60% yield).

IR $v_{max}$ (neat)/cm$^{-1}$: 2952 (w), 1714 (s), 1458 (m), 1402 (s), 1278 (m), 1232 (s), 1157 (s), 1114 (m), 1051 (m), 834 (m), 759 (m), 717 (s); $^1$H NMR (400 MHz, CDCl$_3$, 298 K): rotamer 1: δ 5.86-5.71 (m, 1H), 5.22-5.15 (m, 2H), 4.75 (s, 2H), 3.93 (d, J=5.2 Hz, 2H), 2.96 (s, 3H); rotamer 2: δ 5.86-5.71 (m, 1H), 5.22-5.15 (m, 2H), 4.75 (s, 2H), 3.93 (d, J=5.2 Hz, 2H), 2.94 (s, 3H); $^1$H NMR (400 MHz, CDCl$_3$, 330 K): δ 5.86-5.71 (m, 1H), 5.22-5.15 (m, 2H), 4.76 (s, 2H), 3.94 (d, J=5.6 Hz, 2H), 2.96 (s, 3H); $^{13}$C NMR (100 MHz, CDCl$_3$, 298 K): rotamer 1: δ 154.5, 132.5, 117.5, 95.7, 75.1, 51.8, 34.5; rotamer 2: δ 154.3, 132.5, 117.4, 95.6, 75.1, 51.4, 33.6; HRMS (ESI, m/z): calcd for $C_7H_{10}Cl_3NO_2Na^+$, [M+Na]$^+$, 267.9669, found 267.9665.

Note: in the $^1$H NMR spectra of compound 2,2,2-trichloroethyl allyl(methyl)carbamate, two single peaks (2.96 and 2.94 ppm, s) belong to the methyl group were observed at 298 K and these two signals coalesced at 330 K. Therefore, we assigned one of the signals as the chemical shift from the rotamer of the other conformer.

EXAMPLE 18

Synthesis of 2,2,2-Trichloroethyl (3-Azidopropyl)(methyl)carbamate

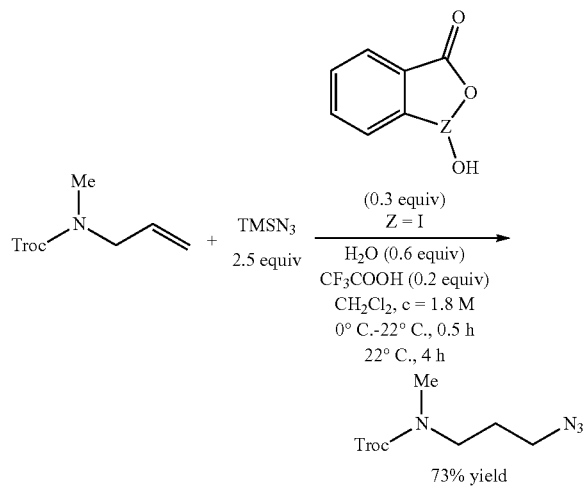

73% yield

The reaction was carried out on a 1.0 mmol scale. Procedure 2 of Example 2 was applied with several modifications: 0.3 equiv of 1-hydroxy-1λ$^3$-benzo[d][1,2]iodaoxol-3(1H)-one and 3.0 equiv of trimethylsilylazide were used; and the reaction was set up at 0° C., slowly warmed to 22° C. over 0.5 hours, and was kept stirring for another 4 h at 22° C. The crude product was purified by column chromatography (hexanes/EtOAc: from 100:1 to 5:1) to afford 2,2,2-trichloroethyl (3-azidopropyl)(methyl)carbamate as a colorless oil (211 mg, 73% yield).

IR $v_{max}$ (neat)/cm$^{-1}$: 2950 (w), 2094 (s), 1714 (s), 1404 (s), 1193 (s), 1142 (s), 1065 (m), 759 (m), 715 (s); $^1$H NMR (400 MHz, CDCl$_3$, 298 K): rotamer δ 4.74 (s, 2H), 3.45-3.32 (m, 4H) 3.00 (s, 3H), 1.90-1.65 (m, 2H); rotamer 2: δ 4.73 (s, 2H), 3.45-3.32 (m, 4H), 2.98 (s, 3H), 1.90-1.65 (m, 2H); $^1$H NMR (400 MHz, CDCl$_3$, 330 K) δ 8 4.74 (s, 2H), 3.42 (t, J=6.8 Hz, 2H), 3.34 (t, J=6.6 Hz, 2H), 2.99 (s, 3H), 1.98-1.79 (m, 2H); $^{13}$C NMR (100 MHz, CDCl$_3$, 298 K): rotamer 1: δ 154.5, 95.7, 75.1, 48.8, 46.9, 35.3, 27.3; rotamer 2: δ 154.3, 95.6, 75.1, 48.8, 46.5, 34.4, 26.8; HRMS (ESI, m/z): calcd for $C_7H_{11}Cl_3N_4O_2Na^+$, [M+Na]$^+$, 310.9840, found 310.9842.

Note: in the $^1$H NMR spectra of 2,2,2-trichloroethyl (3-azidopropyl)(methyl)carbamate, two single peaks (3.00 and 2.98 ppm, s) belong to the methyl group were observed at 298 K. It was observed that these two signals coalesced at 330 K; therefore, we assigned one of the signals as the chemical shift from the rotamer of the other conformer.

EXAMPLE 19

Preparation of tert-Butyl Allyl(2,2,2-trichloroethyl)dicarbamate

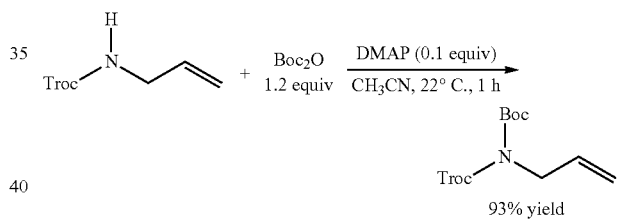

93% yield

To a flame-dried flask (100 mL) equipped with a stir bar were added ,2,2-trichloroethyl allylcarbamate (2,0 g, 8.6 mmol, 1.0 equiv) and Boc$_2$O (2.25 g, 10.3 mmol, 1.2 equiv). After this flask was evacuated and backfilled with N$_2$ twice, anhydrous CH$_3$CN (45 mL) was added, followed by the addition of DMAP (105 mg, 0.86 mmol, 0.1 equiv) in CH$_3$CN (2 mL) via a syringe. The reaction mixture was stirred for 1 h at 22° C. until the starting material was fully consumed (monitored by TLC), then the reaction mixture was evaporated in vacuo, the residue was purified through column chromatography (hexanes/EtOAc: from 50:1 to 10:1) to afford tert-butyl allyl(2,2,2-trichloroethyl)dicarbamate as yellow oil (2.66 g, 93% yield).

IR $v_{max}$ (neat)/cm$^{-1}$: 2982 (w), 1801 (m), 1759 (m), 1717 (s), 1427 (m), 1370 (s), 1344 (s), 1220 (s), 1120 (s), 1061 (m), 851 (m), 810 (m), 716 (s); $^{-1}$H NMR (400 MHz, CDCl$_3$) δ 5.98-5.76 (m, 1H), 5.29-5.10 (m, 2H), 4.81 (s, 2H), 4.30 (dt, J=5.6, 1.3 Hz, 2H), 1.52 (s, 9H); $^{13}$C NMR (100 MHz, CDCl$_3$) δ 151.7, 151.3, 132.7, 117.3, 94.5, 83.7, 75.6, 48.8. 27.9; LRMS (ESI, m/z): calcd for $C_{11}H_{16}Cl_3NO_4Na^+$, [M+Na]$^+$, 354.00, found 354.07.

EXAMPLE 20

Synthesis of tert-Butyl 2,2,2-Trichloroethyl(3-azidopropyl)dicarbamate

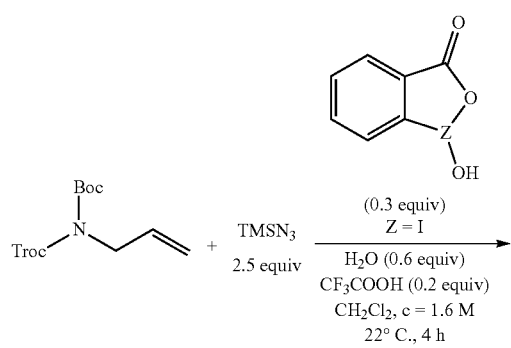

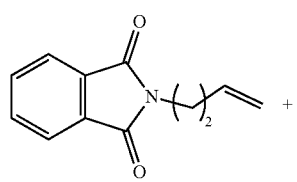

63% yield

The reaction was carried out on a 1.0 mmol scale. Procedure 2 of Example 2 was applied with some modification: 0.3 equiv of 1-hydroxy-1$\lambda^3$-benzo[d][1,2]iodaoxol-3(1H)-one and 2.5 equiv of trimethylsilylazide were used. The crude product was purified through column chromatography (hexanes/EtOAc: from 100:1 to 5:1) to afford tert-butyl 2,2,2-trichloroethyl(3-azidopropyl)dicarbamate as a colorless oil (237 mg, 63% yield).

IR $v_{max}$ (neat)/cm$^{-1}$: 2981 (w), 2098 (s), 1800 (m), 1758 (m), 1726 (m), 1701 (s), 1451 (m), 1370 (s), 1256 (s), 1154 (s), 1114 (s), 851 (m), 811 (m), 762 (m), 716 (s); $^1$H NMR. (400 MHz, CDCl$_3$) δ 4.82 (s, 2H), 3.81 (t, J=7.2 Hz, 2H), 3.35 (t, J=6.7 Hz, 2H), 1.93 (p, J=6.8 Hz, 2H), 1.54 (s, 9H); $^{13}$C NMR (100 MHz, CDCl$_3$) δ 151.8, 151.5, 94.5. 84.0. 75.6, 49.0, 44.4, 28.3, 27.9; HRMS (ESI, m/z): calcd for C$_{11}$H$_{17}$Cl$_3$N$_4$O$_4$Na$^+$, [M+Na]$^+$, 397.0208, found 397.0206.

EXAMPLE 21

Synthesis of 2-(4-Azidobutyl)isoindoline-1,3-dione

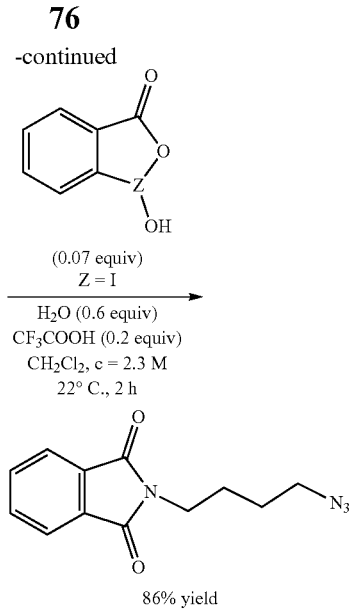

86% yield 2-(But-3-en-1-yl)isoindoline-1,3-dione was prepared using a known procedure see Maikov, A.V. et al. Chemistry—A European Journal 2014, 20, 4542).

The reaction was carried out on a 1.0 mmol scale and Procedure 2 of Example 2 was applied. The crude product was purified through column chromatography (hexanes/EtOAc: from 100:1 to 5:1) to afford 2-(4-azidobutyl)isoindoline-1,3-dione as a colorless oil (211 mg, 86% yield).

IR $v_{max}$ (neat)/cm$^{-1}$: 2944 (w), 2868 (w), 2092 (s), 1771 (m), 1703 (s), 1437 (m), 1395 (s), 1363 (m), 1042 (s), 865 (w), 794 (m), 717 (s), $^1$H NMR (400 MHz, CDCl$_3$) δ 7.82-7.72 (m, 2H), 7.70-7.64 (m, 2H), 3.67 (t, J=7.0 Hz, 2H), 3.29 (t, J=6.8 Hz, 2H), 1.81-1.67 (m, 2H), 1.66-1.53 (m, 2H); $^{13}$C NMR (100 MHz, CDCl$_3$) δ 168.2, 133.8, 131.9, 123.1, 50.7, 37.1, 26.1, 25.7; HRMS (ESI m/z): calcd for C$_{12}$H$_{12}$N$_4$O$_2$Na$^+$, [M+Na]$^+$, 267.0852, found 267.0850.

EXAMPLE 22

Synthesis of 5-Azidopentanoic Acid

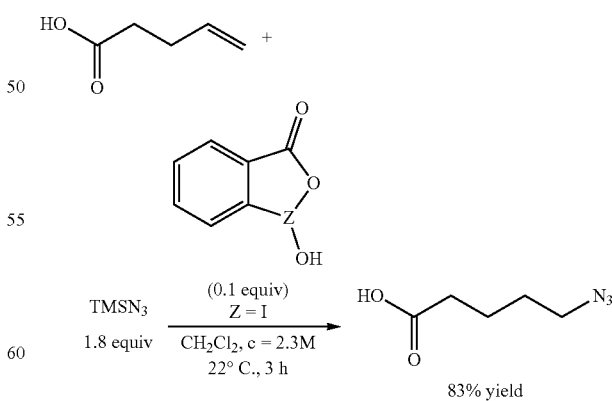

83% yield

Pent-4-enoic acid is commercially available and was used directly without further purification.

The reaction was carried out on a 1.0 tinnol scale. Procedure 1 of Example 1 was applied with some modifications: no external proton source (H$_2$O or trifluoroacetic acid) was added. The crude product was purified through column chromatography (hexanes/EtOAc: from 20:1 to 1:1) to afford 5-azidopentanoic acid as a colorless oil (119 mg, 83% yield) which is a known compound (see Mancuso, L. et al. Chem/gay—A European Journal 2014, 20, 17541).

EXAMPLE 23

Synthesis of 4-Azidobutan-1-ol

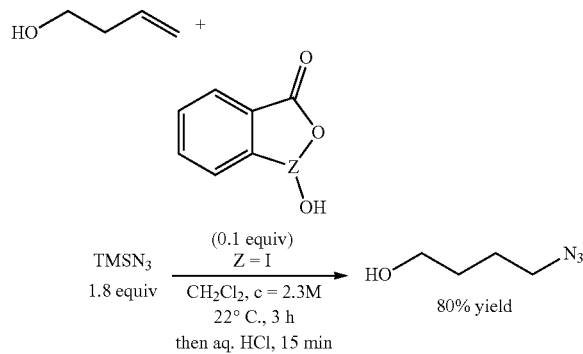

But-3-en-1-ol is commercially available and was distilled before use. The reaction was carried out on a 1.0 mmol scale. Procedure 1 of Example 1 was applied with several modifications: no external proton source (H$_2$O or trifluoroacetic acid) was added; and the reaction was quenched with aqueous HCl (1 M, 1.5 mL,) and stirred for 15 minutes for protodesilylation of the alcohol functional group. The crude product was purified through column chromatography (hexanes/EtOAc: from 100:1 to 3:1) to afford 4-azidobutan-1-ol as a colorless oil (92 mg, 80% yield) which is a known compound (see Khiar, N. et al. The Journal ref Organic Chemistry 2009, 74, 6002).

EXAMPLE 24

Synthesis of 4-(2-Azidoethyl)heptan-4-ol

4-Vinylheptan-4-ol was prepared using a known procedure (see Paquette, L.A. et al. Tetrahedron Letters 1976, 17, 4033).

The reaction was carried out on a 1.0 mmol scale. Procedure 2 of Example 2 was applied with some modification: 0.3 equiv of 1-hydroxy-1λ$^3$-benzo[d][1,2]iodaoxol-3(1H)-one and 2.5 equiv of trimethylsilylazide were used. The crude product was purified through column chromatography (hexanes/EtOAc: from 100:1 to 3:1) to afford 4-(2-azidoethyl)heptan-4-ol as a colorless oil (135 mg, 73% yield).

IR $v_{max}$ (neat)/cm$^{-1}$: 3446 (br), 2959 (s), 2934 (m), 2874 (m), 2091 (s), 1458 (m), 1256 (s), 1139 (s), 964 (m), 908 (m), 744 (m); $^1$H NMR (400 MHz, CDCl$_3$) δ 3.40 (t, J=7.2 Hz, 2H), 1.72 (t, J=7.2 Hz, 2H), 1.49-1.38 (m, 4H), 1.38-1.20 (m, 4H), 0.92 (t, J=7.1 Hz, 6H); $^{13}$C NMR (100 MHz, CDCl$_3$) δ 73.6, 47.1, 41.6, 37.5, 16.8, 14.6; HRMS (ESI, m/z): calcd for C$_9$H$_{19}$N$_3$ONa$^+$, [M+Na]$^+$, 208.1420, found 208.1416.

EXAMPLE 25

Synthesis of 2-Azido-3-methylbutyl Benzoate

3-Methylbut-2-en-1-yl benzoate was prepared using a known procedure (see Yasui, K. et al. The Journal of Organic Chemistry 1995, 60, 1365).

The reaction was carried out on a 1,0 mmol scale. Procedure 2 of Example 2 was applied with some modification: 0.3 equiv of 1-hydroxy-1λ$^3$-benzo[d][1,2]iodaoxol-3(1H)-one and 2.5 equiv of trimethylsilylazide were used. The crude product was puri0fied through column chromatography (hexanes/EtOAc: from 100:1 to 10:1) to afford 2-azido-3-methylbutyl benzoate as a colorless oil (180 mg, 77% yield).

IR v max (neat)/cm$^{-1}$: 2966 (m), 2096 (s), 1720 (s), 1452 (m), 1315 (m), 1267 (s), 1110 (s), 1070 (m), 1026 (m), 709 (s); $^1$H NMR (400 MHz, CDCl$_3$) δ 8.09-8.05 (m, 2H), 7.57 (t, J=7.4 Hz, 1H), 7.45 (t, J=7.7 Hz, 2H), 4.56 (dd, J=11.6, 3.2 Hz, 1H), 4.32 (dd, J=11.5, 8.5 Hz, 1H), 3.58-3.50 (m, 1H), 1.92 (dq, J=13.2, 6.7 Hz, 1H), 1.05 (d, J=6.8 Hz, 3H), 1.03 (d, J=6.4 Hz, 3H); $^{13}$C NMR (100 MHz, CDCl$_3$) δ 166.2, 133.1, 129.7, 129.5, 128.4, 67.0, 66.1, 29.8, 19.4, 18.2; HRMS (ESI, m/z): calcd for C$_{12}$H$_{15}$N$_3$O$_2$Na$^+$, [M+Na]$^+$, 256.1056, found 256.1061.

EXAMPLE 26

Synthesis of 10-Azidodecanal

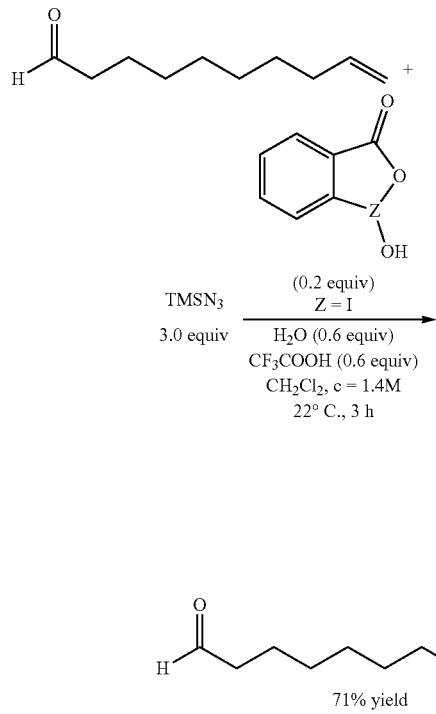

71% yield

Dec-9-enal was prepared using a known procedure (see 1,,ee, R.A. and Donald, D.S. Tetrahedron Letters 1997, 38, 3857). The reaction was carried out on a 1.0 mmol scale. Procedure 2 of Example 2 was applied with some modification. 0.2 equiv of 1-hydroxy-1$\lambda^3$-benzo[d][1,2]iodaoxol-3(1H)-one, 3.0 equiv of trimethylsilylazide, and 0.6 equiv of trifluoroacetic acid were used. The crude product was purified through column chromatography (hexanes/EtOAc: from 100:1 to 10:1) to afford 10-azidododecanal as a colorless oil (140 mg, 71% yield).

IR $\nu_{max}$ (neat)/cm$^{-1}$: 2928 (s), 2856 (s), 2092 (s), 1706 (s), 1412 (m), 1251 (s), 911 (m), 724 (m); $^1$H NMR (400 MHz, CDCl$_3$) δ 9.73 (t, J=1.8 Hz, 1H), 3.23 (t, J=6.9 Hz, 2H), 2.41 (dt, J=7.3, 1,8 Hz, 2H), 1.62-1.53 (m, 4H), 1.43-1.25 (m, 10H), $^{13}$C NMR (100 MHz, CDCl$_3$) δ 202.7, 51.3, 43.8, 29.1 (2 carbon merged), 29.0, 28.9, 28.7, 26.6, 21.9; LRMS: m/z (EI) calcd for C$_{10}$H$_{19}$N$_{19}$NO$^+$, Exact Mass: 169.1 [M–N$_2$]$^+$, 169.1, found 169.1.

EXAMPLE 27

Synthesis of 4-Azido-1-phenylbutan-1-one

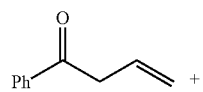

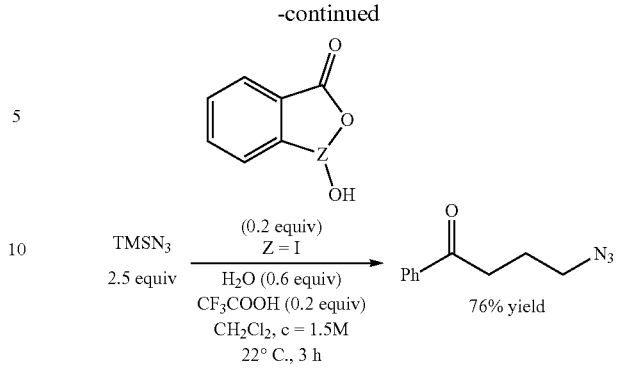

1-Penylbut-3-en-1-one was prepared using a known procedure (see Felpin, F.X. and Lebreton, J. The Journal of Organic Chemistry 2002, 67, 9192).

The reaction was carried out on a 1.0 mmol scale. Procedure 2 of Example 2 was applied with some modification: 0.2 equiv of 1-hydroxy-$\lambda^3$-benzo[d][1,2]iodaoxol-3(1H)-one and 2.5 equiv of trimethylsilylazide were used. The crude product was purified through column chromatography (hexanes/EtOAc: from 100:1 to 10:1) to afford the desired product S44 as a colorless oil (144 mg, 76% yield) which is a known compound (see Ren, R. et al. Angewandte Chemie International Edition 2015, 54, 12692).

EXAMPLE 28

Synthesis of 1-Azido-6-bromohexane

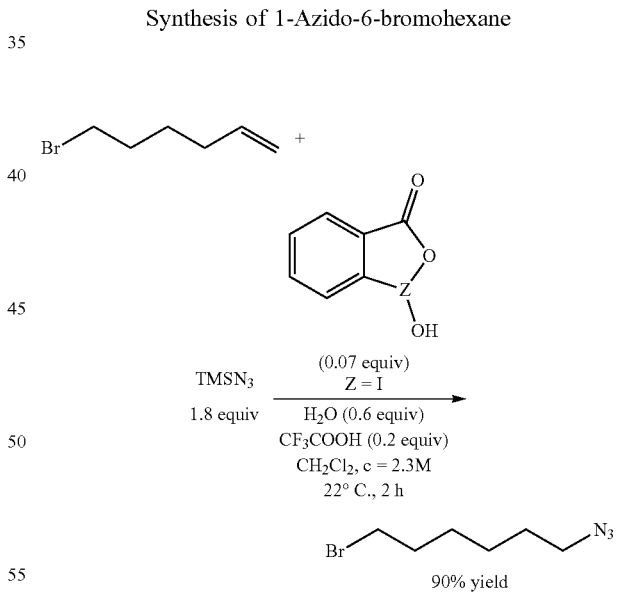

6-Bromohex-1-ene is commercially available and was distilled before use.

The reaction was carried out on a 1.0 mmol scale, and Procedure 2 of Example 2 was applied. The crude product was purified through column chromatography (100% hexanes) to afford 1-azido-6-bromohexane as a colorless oil (186 mg, 90% yield) which is a known compound (see Coutrot, F. and Busseron, E. Chemistry A European Journal 2009, 15, 5186).

EXAMPLE 29

Synthesis of 4-(Azidometyl)-1,7-dichloroheptane

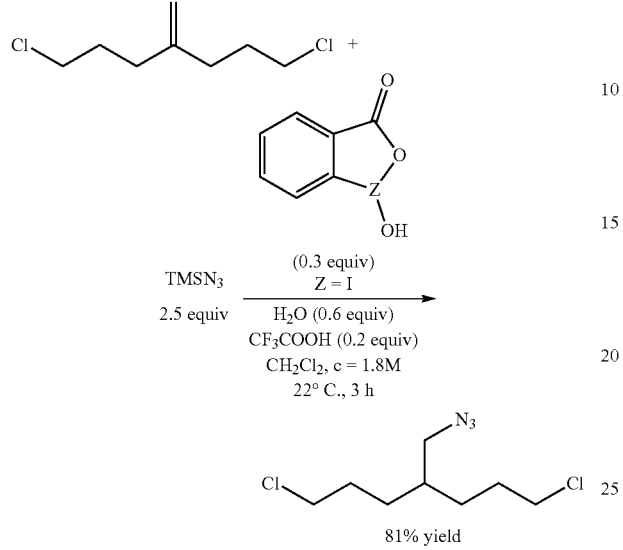

81% yield 1,7-Dichloro-4-methyleneheptane was prepared using a known procedure (see Zhang, C. W. et al. Journal of the American Chemical Socieiy 2013, 135, 14082.

The reaction was carried out on a 1.0 mmol scale. Procedure 2 of Examples 2 was applied with some modification: 0.3 equiv of 1-hydroxy-λ³-benzo[d][1,2]iodaoxol-3(1H)-one and 2.5 equiv of trimethyllsilylazide were used. The crude product was purified through column chromatography (100% hexanes) to afford 4-(azidomethyl)-1,7-dichloroheptane as a colorless oil (182 mg, 81% yield).

IR $\nu_{max}$ (neat)/cm$^{-1}$: 2934 (m), 2868 (w), 2093 (s), 1452 (m), 1286 (s), 764 (m), 722 (s); $^1$H NMR (400 MHz, CDCl$_3$) δ 3.53 (t, J=6.6 Hz, 4H), 3.28 (d, J=5.7 Hz, 2H), 1.87-1.72 (m, 4H), 1.69-1.58 (m, 1H) 1.54-1.41 (m, 4H); $^{13}$C NMR (100 MHz, CDCl$_3$) δ 54.8, 44.9, 37.2, 29.6, 28.9; LRMS: m/z (EI) calcd for $C_8H_{15}Cl_2N^+$, $[M-N_2]^+$, 195.1, found 195.1.

EXAMPLE 30

Synthesis of Diethyl 3-(Azidomethyl)-4-methylcyclopentane-1,1-dicarboxylate

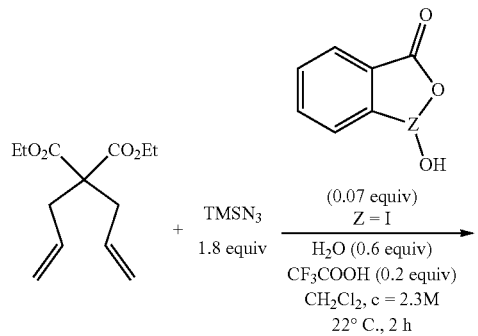

94% yield, dr. 7.5:1

Diethyl 2,2-diallylmalonate was prepared using a known procedure (see Krafft, M. E. et al. The Journal of Organic Chemistry 2002, 67, 1233), The reaction was carried out on a 1.0 mmol scale, and Procedure 2 of .Example 2 was applied. The crude product was purified through column chromatography (hexanes/EtOAc: from 100:1 to 10:1) to afford diethyl 3-(azidomethyl)-4-methylcyclopentane-1,1-dicarboxylate as a colorless oil (266 mg, 94% yield) which is a known compound (see Leggans, E. K. et al. Organic Letters 2012,14, 1428):

EXAMPLE 31

Synthesis of (2S,5S)-5-(1-Azidopropan-2-yl)-2-methyleyelohexan-1-one

75% yield, dr: 1:1

(−)-Dihydrocarvone was prepared using a known procedure (see Caboni, P. et al. Journal of Agricultural and Food Chemistry 2013, 61, 9784).

The reaction was carried out on a 1.0 mmol scale. Procedure 2 of Example 2 was applied with some modification: 0.2 equiv of 1-hydroxy-1λ³-benzo[d][1,2]iodaoxol-3(1H)-one and 2.5 equiv of trimethylsilylazide were used. The crude product was purified through column chromatography (hexanes/EtOAc: from 100:1 to 10:1) to afford (2S, 5S)-5-(1-azidopropan-2-yl)-2-methylcyclohexan-1-one as a colorless oil (146 mg, 75% yield, dr: 1:1).

IR $\nu_{max}$ (neat)/cm$^{-1}$: 2966 (w), 2931 (m), 2872 (w), 2093 (s), 1709 (s), 1452 (m), 1271 (s), 1221 (m), 1145 (w), 960 (w), 861 (m), 710 (m); $^1$H NMR (400 MHz, CDCl$_3$): (Diastereomer 1 and 2 overlap) δ 3.33-3.20 (m, 1H), 3.20-3.08 (m, 1H), 2.37-2.21 (m, 2H), 2.18-1.97 (m, 2H), 1.84-1.72 (m, 2H), 1.71-1.57 (m, 1H), 1.56-1.36 (m, 1H), 1.35-1.18 (m, 1H), 0.97 (d, J=6.5 Hz, 3H), 0.92 (dd, J=8.7, 4.8 Hz, 3H); $^{13}$C NMR (100 MHz, CDCl$_3$): Diastereomer 1: δ 212.3, 55.2, 45.8, 44.8, 42.1, 37.8, 34.6, 29.5, 14.2, 14.1; Diastereomer 2: δ 212.2, 55.2, 44.7, 43.9, 42.0, 37.8, 34.6, 27.3, 14.2, 14.1; LRMS: m/z (EI) calcd for C$_{10}$H$_{17}$NO$^+$, [M−N$_2$]$^+$, 167.1, found 167.1.

EXAMPLE 32

Synthesis of (R)-((1S,2S,4S,5R)-5-(2-Azidoethyl) qinuclidin-2-yl)(6-methoxyquinolin-4-yl)methyl Acetate

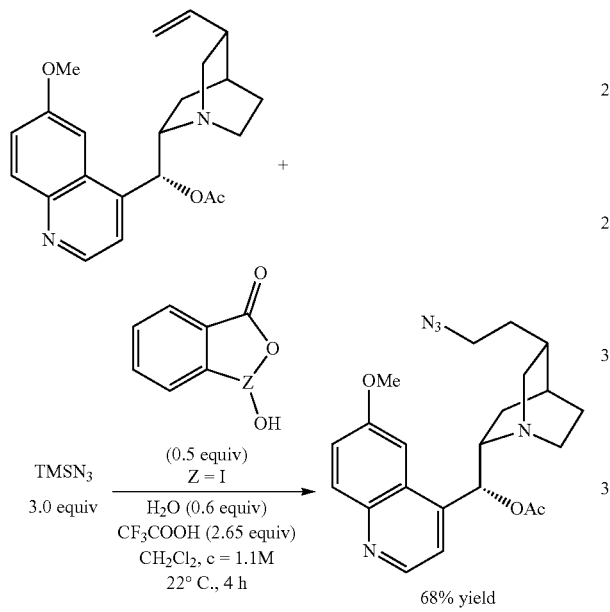

68% yield (R)-(6-Methoxyquinolin-4-yl)((1S,2S,4S,5R)-5-vinylquinuclidin-2-yl)methyl acetate was prepared using a known procedure (see Monar, I. G. et al. Journal of the American Chemical Society 2016, 138, 5004).

To a flame-dried sealable 2-dram vial equipped with a stir bar were added (R)-(6-methoxyquinolin-4-yl) ((1S,2S,4S,5R)-5-vinylquinuclidin-2-yl)methyl acetate (183 mg, 0.5 mmol, 1.0 equiv) and 1-hydroxy-1λ$^3$-benzo[d][1,2]iodaoxol-3(1H)-one (66 mg, 0.25 mmol, 0.5 equiv). After this vial was evacuated and backfilled with N$_2$ twice, anhydrous CH$_2$Cl$_2$ (0.25 mL) was added, then the reaction was cooled to −10° C., TFA (79 μL, 1.03 mmol, 2.05 equiv) was added. The reaction mixture was stirred for 20 min at −10° C., then H$_2$O (5.4 μL, 0.3 mmol, 0.6 equiv) and TMSN$_3$ (197 μL, 1.5 mmol, 3 equiv) was added successively, follow by the addition of TFA (23 μL, 0.3 mmol), then the reaction was warmed to 22° C. and kept stirring for 4 h at the same temperature until the starting material was fully consumed (monitored by TLC). The reaction was cooled to 0° C., quenched with EtOAc (2 mL) and saturated Na$_2$CO$_3$ solution (2 mL). The organic layer was separated from the aqueous layer, which was extracted with EtOAc (3 mL×3). The combined organic layers were dried over anhydrous Na$_2$SO$_4$ and concentrated in vacuo. The residue was subsequently purified through a silica gel column (Et$_2$O/THF: from 100:1 to 3:1) to afford (R)-(1S,2S,4S,5R)-5-(2-azidoethyl)quinuclidin-2-yl)(6-methoxyquinolin-4-yl)methyl acetate as a colorless oil (139 mg, 68% yield).

IR $ν_{Max}$ (neat)/cm$^{-1}$: 2929 (m), 2866 (w), 2094 (s), 1742 (s), 1620 (s), 1508 (s), 1367 (m), 1225 (s), 1026 (s), 853 (m), 831 (m), 717 (m); $^1$H NMR (400 MHz, CDCl$_3$) δ 8.74 (d, J=4.5 Hz, 1H), 8.01 (d, J=9.2 Hz, 1H), 7.42 (d, J=2.7 Hz, 1H), 7.37 (dd, J=9.2, 2.7 Hz, 1H), 7.34 (d, J=4.5 Hz, 1H), 6.48 (d, J=7.2 Hz, 1H), 3.95 (s, 3H), 3.43-3.18 (m, 3H), 3.15-3.02 (m, 2H), 2.64 (ddd, J=14.5, 11.4, 4.7 Hz, 1H), 2.33 (dt, J=14.0, 3.1 Hz, 1H), 2.13 (s, 3H), 1.89-1.47 (m, 8H); $^{13}$C NMR (100 MHz, CDCl$_3$) δ 170.0, 157.9, 147.4, 144.8, 143.5, 131.8, 127.0, 121.7, 118.8, 101.5, 73.7, 59.0, 57.8, 55.6, 49.7, 42.4, 33.8, 32.8, 28.2, 25.6, 24.0, 21.1; HRMS (ESI, m/z): calcd for C$_{22}$H$_{28}$N$_5$O$_3^+$, [M+H$^+$], 410.2187, found 410.2182.

EXAMPLE 33

Preparation of tert-Butyl 3-Allyl-4-oxo-1,2,3,4-tetrahydro-9H-carbazole-9-carboxylate

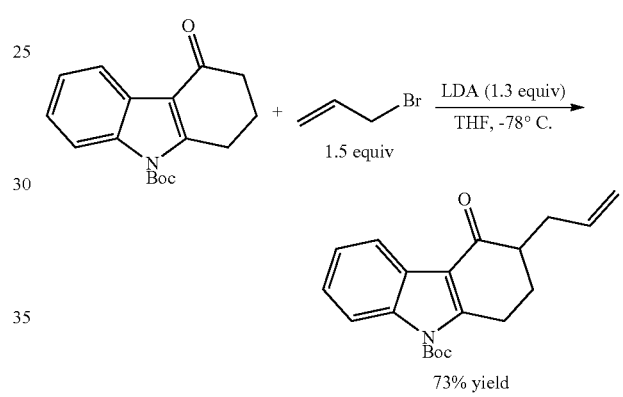

73% yield tert-Butyl 4-oxo-1,2,3,4-tetrahydro-9H-carbazole-9-carboxylate was prepared using a known procedure (see Yang, Y. et al. Organic Letters 2014, 16, 6216).

To a flame-dried flask (50 mL) equipped with a stir bar were added $^i$Pr$_2$NH (1.28 ml, 9.1 mmol, 1.3 equiv) and anhydrous THF (20 mL). After the flask was cooled to −78° C., n-BuLi (2.5 M in hexane, 3.64 mL, 9.1 mmol, 1.3 equiv) was added. After 30 min the mixture was transferred by a cannula to another flask (100 mL) containing a solution of tert-butyl 4-oxo-1,2,3,4-tetrahydro-9H-carbazole-9-carboxylate (2.0 g, 7.0 mmol) in THF (30 mL) at −78° C. The resulting solution was stirred at −78° C. for 1 h before a solution of allyl bromide (0.9 mL, 10.5 mmol, 1.5 equiv) in THF (10 mL) was added via a syringe. The reaction mixture was slowly warmed up to −20° C. in 2 h and kept stirring for 5 h until the starting material was fully consumed (monitored by TLC). EtOAc (15 mL) and saturated NH$_4$Cl solution (10 mL) were added to quench the reaction. The organic phase was separated from the aqueous phase, and the aqueous phase was extracted with EtOAc (20 mL×3). The combined organic phase was washed with brine (20 mL) and dried over Na$_2$SO$_4$. After concentration in vacuo, the residue was purified through column chromatography (hexanes/EtOAc: from 50:1 to 5:1) to afford tert-butyl 3-allyl-4-oxo-1,2,3,4-tetrahydro-9H-carbazole-9-carboxylate as a white solid (1.66 g, 73% yield, m.p. 114-116° C.).

IR $ν_{max}$ (neat)/cm$^{-1}$: 3078 (w), 2980 (m), 2934 (w), 1738 (s), 1664 (s), 1558 (m), 1483 (m), 1457 (s), 1369 (s), 1346 (s), 1318 (s), 1230 (m), 1143 (s), 1117 (s), 1077 (m), 900 (s), 831 (m), 767 (s), 732 (m); $^1$H NMR (400 MHz, CDCl$_3$) δ 8.34-8.25 (m, 1H), 8.13-8.04 (m, 1H), 7.38-7.28 (m, 2H), 5.96-5.80 (m, 1H), 5.15-5.07 (m, 2H), 3.43 (dt, J=19.0, 5.0 Hz, 1H), 3.21 (ddd, J=19.0, 9.5, 5.2 Hz, 1H), 2.85-2.71 (m, 1H), 2.55 (ddt, J=10.5, 8.8, 4.4 Hz, 1H), 2.37-2.19 (m, 2H), 2.05-1.90 (m, 1H), 1.71 (s, 9H); $^{13}$C NMR (100 MHz, CDCl$_3$) δ 196.6, 151.4, 149.8, 136.4, 136.0, 125.9, 124.8, 124.3, 121.5, 116.8 (2 carbon merged), 115.1, 85.3, 45.8, 33.6, 28.2, 28.0, 25.0; HRMS (ESI, m/z): calcd for C$_{20}$H$_{23}$NO$_3$Na$^+$, [M+Na]$^+$, 348.1570, found 348.1572.

EXAMPLE 34

Synthesis of tert-Butyl 3-(3-Azidopropyl)-4-oxo-1,2,3,4-tetrahydro-9H-carbazole-9-carboxylate

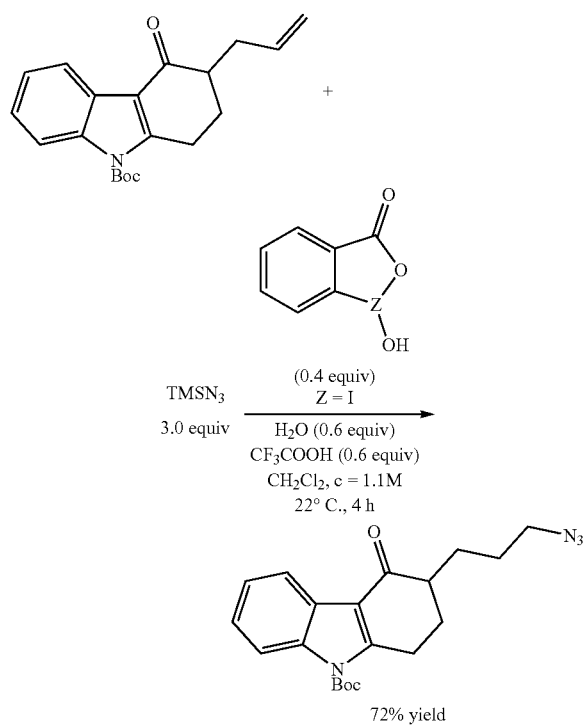

To a flame-dried sealable 2-dram vial equipped with a stir bar were added tert-butyl 3-allyl-4-oxo-1,2,3,4-tetrahydro-9H-carbazole-9-carboxylate (130 mg, 0.4 mmol, 1.0 equiv) and 1-hydroxy-1λ$^3$-benzo[d][1,2]iodaoxol-3(1H)-one (42 mg, 0.16 mmol, 0.4 equiv). After this vial was evacuated and backfilled with N$_2$ twice, anhydrous CH$_2$Cl$_2$ (0.2 mL) and H$_2$O (4.3 μL, 0.24 mmol, 0.6 equiv) were added via syringes. After the vial was cooled to 0° C., freshly distilled TMSN$_3$ (158 μL, 1.2 mmol, 3.0 equiv) was added to the reaction followed by the addition of TFA (18.4 μL, 0.24 mmol, 0.6 equiv). The mixture was warmed up to 22° C. and kept stirring for 4 h until the olefin was fully consumed (monitored by TLC). The reaction was cooled to 0° C., EtOAc (2 mL) and saturated NaHCO$_3$ solution (1.5 mL) were added to quench the reaction and to remove any residual hydrazoic acid. The organic phase was separated from the aqueous phase, and the aqueous phase was extracted with EtOAc (3 mL×3). The combined organic phase was washed with brine (2 mL) and dried over Na$_2$SO$_4$. After concentration in vacuo, the residue was purified through column chromatography (hexanes/Et$_2$O: from 100:1 to 50:1) to afford tert-butyl 3-(3-azidopropyl)-4-oxo-1,2,3,4-tetrahydro-9H-carbazole-9-carboxylate as a colorless oil (106 mg, 72% yield).

IR ν$_{max}$ (neat)/cm$^{-1}$: 2984 (m), 2932 (m), 2092 (s), 1743 (s), 1651 (s), 1561 (m), 1481 (m), 1457 (s), 1370 (m), 1351 (s), 1260 (m), 1146 (s), 1116 (s), 834 (w), 759 (s), 748 (s); $^1$H NMR (400 MHz, CDCl$_3$) δ 8.30-8.24 (m, 1H), 8.12-8.04 (m, 1H), 7.36-7.30 (m, 2H), 3.44 (dt, J=19.0, 5.2 Hz, 1H), 3.39-3.30 (m, 2H), 3.24 (ddd, J=19.0, 9.0, 5.2 Hz, 1H), 2.56-2.43 (m, 1H), 2.36-2.28 (m, 1H), 2.07-1.93 (m, 2H), 1.82-1.73 (m, 2H), 1.71 (s, 9H), 1.63-1.54 (m, 1H); $^{13}$C NMR (100 MHz, CDCl$_3$) δ 197.0, 151.1, 149.8, 135.9, 125.8, 124.8, 124.3, 121.4, 116.7, 115.1, 85.4, 51.6, 45.7, 28.7, 28.2, 26.7, 26.5, 24.9; HRMS m/z): calcd for C$_{20}$H$_{24}$N$_4$O$_3$Na$^+$, [M+Na]$^+$, 391.1741, found 391,1750.

EXAMPLE 36

Preparation of (3S,5S,10S,13R)-10,13-Dimethyl-17-((R)-6-methylheptan-2-yl) hexadecahydro-1H-cyclopenta[a]phenanthren-3-yl pent-4-enoate

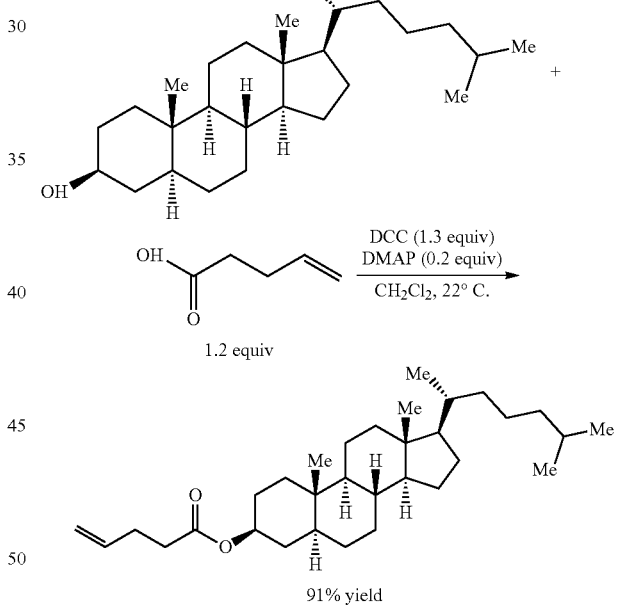

5α-Cholestan-3β-ol is commercially available and was used directly without further purification.

To a flame-dried flask (25 mL) equipped with a stir bar were added 5α-Cholestan-3β-ol (389 g, 1.0 mmol, 1.0 equiv), DCC (268 mg, 1.3 mmol, 1.3 equiv), and DMAP (24.4 mg, 0.2 mmol, 0.2 equiv). After this flask was evacuated and backfilled with N$_2$ twice, anhydrous CH$_2$Cl$_2$ (10 mL) and 4-pentenoic acid (120 mg, 1.2 mmol, 1.2 equiv) were added via syringes. After stirring at 22 for 10 h, EtOAc (10 mL) and saturated NaHCO$_3$ solution (10 mL) were added to quench the reaction, the organic phase was separated from the aqueous phase, and the aqueous phase was extracted with EtOAc (10 mL×3). The combined organic phase was washed with brine (15 mL) and dried over Na$_2$SO$_4$. After concentration in vacuo, the residue was purified through column chromatography (hexanes/EtOAc: from 50:1 to 10:1) to afford (3S,5S,10S,13R)-10,13-dimethyl-17-((R)-6-methylheptan-2-yl) hexadecahydro-1H-cyclopenta[a]phenanthren-3-yl pent-4-enoate as a white solid (429 mg, 91% yield, m.p. 83-85° C.).

IR $v_{max}$ (neat)/cm$^{-1}$: 2928 (s), 2853 (s), 1733 (s), 1645 (w), 1469 (m), 1445 (m), 1382 (m), 1273 (m), 1177 (s), 998 (m), 912 (s), 734 (w); $^1$H NMR (400 MHz, CDCl$_3$) δ 5.92-5.70 (m, 1H), 5.05 (d, J=17.2 Hz, 1H), 4.99 (d, J=11.2 Hz, 1H), 4.78-4.63 (m, 1H), 2.37-2.35 (m, 4H), 1.96 (dd, J=9.4, 3.1 Hz, 1H), 1.86-1.75 (m, 2H), 1.75-1.68 (m, 1H), 1.64 (dt, J=17.4, 5.5 Hz, 1H), 1.57-1.41 (m, 4H), 1.39-1.20 (m, 9H), 1.19-0.93 (m, 11H), 0.93-0.83 (m, 9H), 0.81 (s, 3H), 0.64 (s, 3H); $^{13}$C NMR (100 MHz, CDCl$_3$) δ 172.6, 136.8, 115.4, 73.7, 56.4, 56.3, 54.2, 44.7, 42.6, 40.0, 39.5, 36.8, 36.2, 35.8, 35.5 (2 carbon merged), 34.1, 33.9, 32.0, 29.0, 28.6, 28.2, 28.0, 27.5, 24.2, 23.8, 22.8, 22.6, 21.2, 18.7, 12.2, 12.1; HRMS (ESI, m/z): calcd for C$_{32}$H$_{54}$O$_2$Na$^+$, [M+Na]$^+$, 493.40, found 493.43.

EXAMPLE 37

Preparation of (3S,5S,10S,13R)-10,13-Dimethyl-17-((R)-6-methylheptan-2-yl) hexadecahydro-1H-cyclopenta[a]phenanthren-3-yl 5-aziclopentanoate

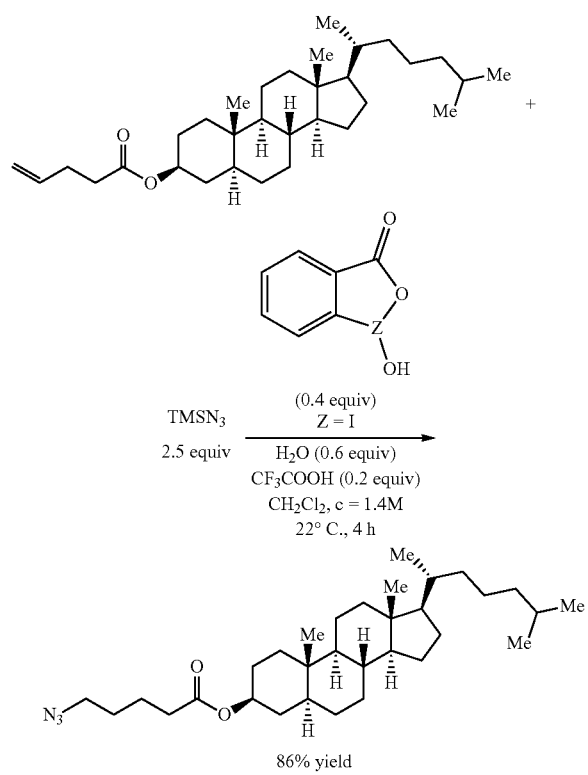

86% yield

To a flame-dried sealable 2-dram vial equipped with a stir bar were added (3S,5S,10S,13R)-10,13-dimethyl-17-((R)-6-methylheptan-2-yl) hexadecahydro-1H-cyclopenta[a]phenanthren-3-yl pent-4-enoate (235 mg, 0.5 mmol, 1.0 equiv) and 1-hydroxy-1λ$^3$-benzo[d][1,2]iodaoxol-3(1H)-one 53 mg, 0.2 mmol, 0.4 equiv). After this vial was evacuated and backfilled with N$_2$ twice, anhydrous CH$_2$Cl$_2$ (0.2 mL) and H$_2$O (5.4 μL, 0.3 mmol, 0.6 equiv) were added via syringes. After the vial was cooled to 0° C., freshly distilled TMSN$_3$ (164 μL, 1.25 mmol, 2.5 equiv) was added to the reaction followed by the addition of TFA (7.7 μL, 0.1 mmol, 0.2 equiv). The mixture was warmed up to 22° C. and kept stirring for 4 h until the olefin was fully consumed (monitored by TLC). The reaction was cooled to 0° C., EtOAc (2 mL) and saturated NaHCO$_3$ solution (1.5 mL) were added to quench the reaction and to remove any residual hydrazoic acid. The organic phase was separated from the aqueous phase, and the aqueous phase was extracted with EtOAc (3 mL×3). The combined organic phase was washed with brine (2 mL) and dried over Na$_2$SO$_4$. After concentration in vacuo, the residue was purified through column chromatography (hexanes/Et$_2$O: from 100:1 to 50:1) to afford (3S,5S,10S,13R)-10,13-dimethyl-17-((R)-6-methylheptan-2-yl) hexadecahydro-1H-cyclopenta[a]phenanthren-3-yl 5-azidopentanoate as a colorless oil (221 mg 86% yield).

IR $v_{max}$ (neat)/cm$^{-1}$: 2930 (s), 2867 (s), 2096 (s), 1731 (s), 1508 (m), 1251 (m), 1177 (s), 1151 (s), 1006 (m), 929 (w), 737 (w); $^1$H NMR (400 MHz, CDCl$_3$) δ 4.82-4.56 (m, 1H), 3.28 (t, J=6.6 Hz, 2H), 2.30 (t, J=7.1 Hz, 2H), 1.95 (dt, J=12.3, 3.1 Hz, 1H), 1.86-1.75 (m, 2H), 1.74-1.42 (m, 12H), 1.40-1.20 (m, 10H), 1.19-0.94 (m, 11H), 0.89 (d, J=6.5 Hz, 3H), 0.86 (d, J=6.4 Hz, 3H), 0.85 (d, J=6.8 Hz, 3H), 0.81 (s, 3H), 0.64 (s, 3H); $^{13}$C NMR (100 MHz, CDCl$_3$) δ 172.7, 73.8, 56.4, 56.2, 54.2, 51.0, 44.6, 42.6, 40.0, 39.5, 36.7, 36.1, 35.8, 35.4 (2. carbon merged), 34.0 (2 carbon merged), 32.0, 28.6, 28.2 (2 carbon merged), 28.0, 27.5, 24.2, 23.8, 22.8, 22.5, 22.2, 21.2, 18.6, 12.2, 12.0; HRMS (ESI, m/z): calcd for C$_{32}$H$_{55}$N$_3$O$_2$Na$^+$, [M+Na]$^+$. 536.4186, found 536.4182.

EXAMPLE 38

Preparation of (2R,3R,4S,5R,6S)-2-((But-3-en-1-yloxy)methyl)-3,4,5,6-tetramethoxytetrahydro-2H-pyran

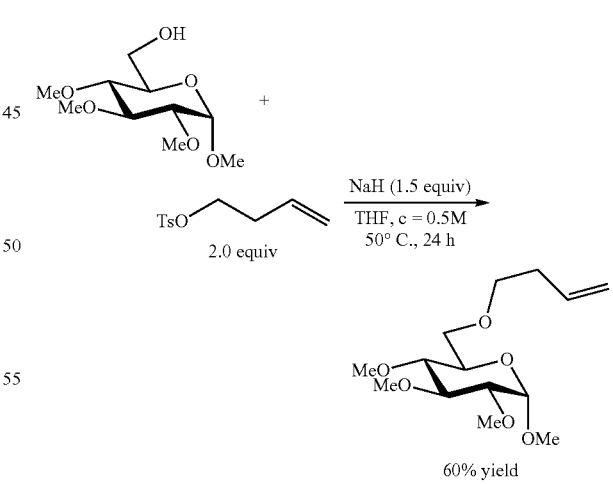

60% yield

Methyl 2,3,4-Tri-O-methyl-α-D-glucopyranoside was prepared using a known procedure (see Boultadakis-Arapinis, M. et al, Chemistry—A European Journal 2013, 19, 6052).

To a flame-dried flask (10 mL) equipped with a stir bar were added methyl 2,3,446—O-methyl-α-D-glucopyranoside (472 mg, 2.0 mmol. 1.0 equiv) and but-3-en-1-yl 4-methylbenzenesulfonate (905 mg, 4.0 mmol, 2.0 equiv). After the flask was evacuated and backfilled with $N_2$ twice, anhydrous THF (4 inL) was added. After the flask was cooled to 0° C., NaH (120 mg, 3.0 mmol, 1.5 equiv, 60% in mineral oil) was added to the solution portion-wise. The reaction mixture was stirred for 20 min at 0° C. before warming to 50° C. and kept stirring for 24 h until the starting material was fully consumed (monitored by TLC). The reaction was cooled to 0° C., $Et_2O$ (5 mL) and saturated $NH_4Cl$ solution (5 mL) were added to quench the reaction. The organic phase was separated from the aqueous phase, and the aqueous phase was extracted with $Et_2O$ (5 mL×3). The combined organic phase was washed with brine (5 mL) and dried over $Na_2SO_4$. After concentration in vacuo, the residue was purified through column chromatography (hexanes/EtOAc: from 50:1 to 3:1) to afford (2R,3R,4S,5R,6S)-2-((but-3-en-1-yloxy)methyl)-3,4,5,6-tetramethoxytetrahydro-2H- pyran as a colorless oil (348 mg, 60% yield). IR $v_{max}$ (neat)/cm$^{-1}$: 2914 (m), 2835 (w), 1739 (w), 1642 (w), 1445 (w), 1376 (w), 1269 (m), 1189 (m), 1159 (s), 1099 (s), 1047 (s), 994 (s), 915 (m), 734 (s), 702 (s); $^1$H NMR (400 MHz, CDCl$_3$) δ 5.76 (ddt, J=17.1, 10.2, 6.8 Hz, 1H), 5.11-4.91 (m, 2H). 4.76 (d, J=3.6 Hz, 1H), 3.58-3.54 (m, 2H), 3.55 (s, 3H), 3.53-3.48 (m, 2H), 3.47 (s, 3H), 3.44 (s. 3H), 3.43-3.37 (m, 2H), 3.33 (s, 3H), 3.20-3.09 (m, 2H). 2.35-2.26 (m, 2H); $^{13}$C NMR (100 MHz, CDCl$_3$) δ 135.0, 116.3, 97.3, 83.4, 81.6, 79.2, 70.8, 69.8, 69.1, 60.7, 60.3, 58.8, 54.9, 34.0; LRMS (ESI, m/z): calcd for $C_{14}H_{26}O_6Na^+$, [M+Na$^+$], 313.16, found 313.16.

EXAMPLE 39

Synthesis of (2R,3R,4S,5R,6S)-2-((4-Azidobutoxy)methyl)-3,4,5,6-tetramethoxytetrahydro-2H-pyran

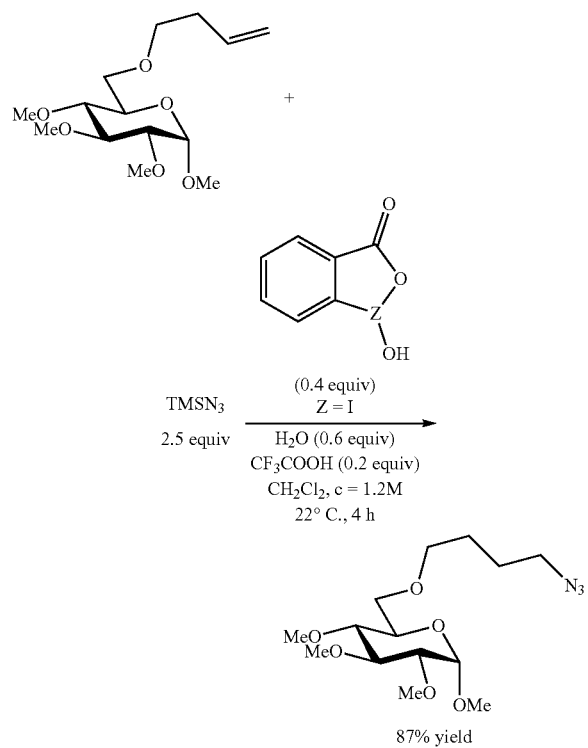

87% yield

To a flame-dried sealable 2-dram vial equipped with a stir bar were added (2R,3R,4S,5R,6S)-2-((but-3-en-1-yloxy)methyl)-3,4,5,6-tetramethoxytetrahydro-2H-pyran (116 mg, 0.4 mmol, 1.0 equiv) and 1-hydroxy-1λ$^3$-benzo[d][1,2]iodaoxol-3(1H)-one (42 mg, 0.16 mmol, 0.4 equiv). After this vial was evacuated and backfilled with $N_2$ twice, anhydrous $CH_2Cl_2$ (0.2 mL) and $H_2O$ (4.3 μL, 0.24 mmol, 0.6 equiv) were added via syringes. After the vial was cooled to 0° C., freshly distilled TMSN$_3$ (131 μL, 1.0 mmol, 2.5 equiv) was added to the reaction followed by the addition of TFA (6.1 μL, 0.08 mmol, 0.2 equiv). The mixture was warmed up to 22° C. and kept stirring for 4 h until the olefin was fully consumed (monitored by TLC). The reaction was cooled to 0° C., EtOAc (2 mL) and saturated NaHCO$_3$ solution (1.5 mL) were added to quench the reaction and to remove any residual hydrazoic acid. The organic phase was separated from the aqueous phase, and the aqueous phase was extracted with EtOAc (3 mL×3). The combined organic phase was washed with brine (2 mL) and dried over $Na_2SO_4$. After concentration in vacuo, the residue was purified through column chromatography (hexanes/EtOAc: from 100:1 to 3:1) to afford (2R,3R,4S,5R,6S)-2-((4-azidobutoxy)methyl)-3,4,5,6-tetramethoxytetrahydro-2H-pyran as a colorless oil (116 mg, 87% yield).
IR $v_{max}$ (neat)/cm$^{-1}$: 2935 (m), 2253 (w), 2099 (s), 1447 (w), 1376 (w), 1265 (m), 1159 (m), 1098 (s), 1047 (s), 907 (s), 728 (s); $^1$NMR (400 MHz, CDCl$_3$) δ 4.81 (d, J=3.6 Hz, 1H), 3.62 (s, 3H), 3.61-3.54 (m, 4H), 3.53 (s, 3H), 3.50 (s, 3H), 3.49-3.44 (m, 2H), 3.39 (s, 3H). 3.29 (t, J=6.4 Hz, 2H), 3.23-3.14 (m, 2H), 1.74-1.60 (m, 4H); $^{13}$C NMR (100 MHz, CDCl$_3$) δ 97.5, 83.6, 81.7, 79.4, 70.9, 69.9, 69.3, 60.9, 60.5, 59.0, 55.1, 51.3, 26.8, 25.8; HRMS (ESI, m/z): calcd for $C_{14}H_{27}N_3O_6Na^+$, [M+Na]$^+$, 356.1792, found 356.1797.

EXAMPLE 40

Large Scale Synthesis of tert-Butyl Dodecylcarbamate via Azide Intermediate

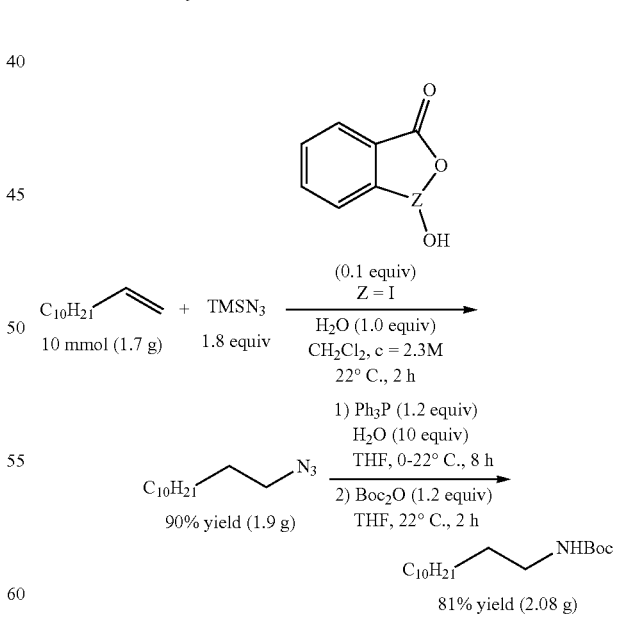

1-Dodecene is commercially available and was distilled before use.
The reaction was carried out on a 10 mmol scale, and Procedure 1 of Example 1 was applied. 1-Azidododecane was isolated as a colorless oil (1.9 g, 90% yield).

To a flask (100 mL) vial equipped with a stir bar were added 1-azidododecane (1.9 g, 9.0 mmol, 1.0 equiv) isolated from the last step, H$_2$O (1.62 mL, 90 mmol, 10 equiv) and THF (40 mL). After the flask was evacuated and backfilled twice with N$_2$, a solution of PPh$_3$ (2.83 g, 10.8 mmol, 1.2 equiv) in THF (20 mL) was added drop-wise at 0° C. The mixture was warmed up to 22° C. and kept stirring for 8 h (monitored by TLC until the azide was fully consumed). Subsequently, Boc$_2$O (2.36 g, 10.8 mmol, 1.2 equiv) in THF (10 mL) was added to the above mixture drop-wise at 22° C. The resulting mixture was stirred for additional 2 h until the amine intermediate was fully consumed (monitored by TLC). After concentration in vacuo, the residue was subsequently purified through column chromatography (hexanes/EtOAc: from 50:1 to 10:1) to afford tert-butyl dodecylcarbamate as a white solid (2.08 g, 81% yield, m.p. 37-39° C.). IR $v_{max}$ (neat)/cm$^{-1}$: 3380 (m), 2917 (s), 2851 (s), 1687 (s), 1514 (s), 1470 (m), 1364 (m), 1244 (s), 1044 (m), 975 (m), 868 (m), 719 (m); $^1$H NMR (400 MHz, CDCl$_3$) δ 4.49 (br s, 1H), 3.14-3.05 (m, 2H), 1.47-1.40 (m, 11H), 1.27-1.24 (m, 18H), 0.88 (t, J=6.8 Hz, 3H); $^{13}$C NMR (100 MHz, CDCl$_3$) δ 156.0, 79.0, 40.6, 31.9, 30.1, 29.6 (four carbons merged), 29.3 (two carbons merged), 28.4, 26.8, 22.7. 14.1; HRMS (ESI, m/z): calcd for C$_{17}$H$_{35}$NO$_2$Na$^+$, [M+Na]$^+$, 308.2560, found 308.2564.

EXAMPLE 41

Large Scale Synthesis of tert-Butyl (Bicyclo[2.2.1]heptan-2-yl)carbamate via Azide Intermediate

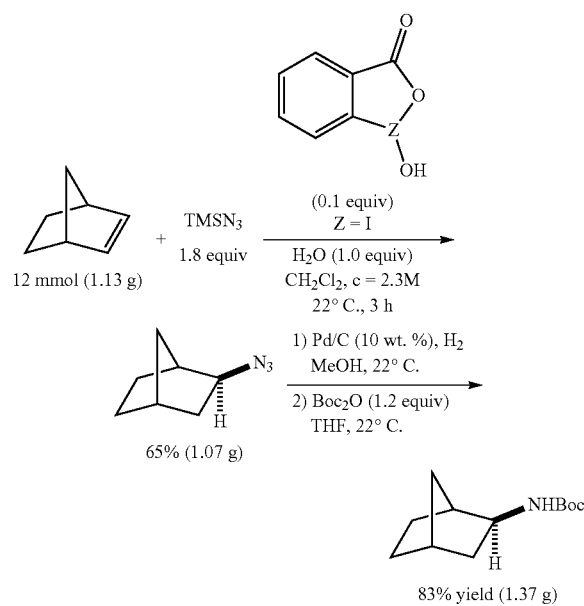

The reaction was carried out on a 12 mmol scale, and Procedure 1 of Example 1 was applied. 2-Azidobicyclo[2.2.1]heptane was isolated as a colorless oil (1.07 g, 65% yield).

To a 100 mL 2-neck round bottom flask equipped with a stir bar and a three-way adapter was added Pd/C (107 mg, 10 wt. %). After the flask was evacuated and backfilled twice with N$_2$, a solution of 2-azidobicyclo[2.2.1]heptane (1.07 g, 7.8 mmol, 1.0 equiv) in THF (50 mL) was added. The mixture was degassed with brief evacuation and backfilled three times with H$_2$, and then vigorously stirred under H$_2$ balloon at 22° C. for 5 h (monitored by TLC until the azide S11 was fully consumed). The solution was filtered through a Celite pad and washed with MeOH (20 mL). The combined filtrates were concentrated to afford the crude amine, which was then dissolved in 40 mL THF, Boc$_2$O (2.04 g, 9.36 mmol, 1.2 equiv) in THF (10 mL) was added to the above mixture drop-wise at 0° C. The resulting mixture was warmed up to room temperature and kept stirring for additional 2 h until the amine intermediate was fully consumed (monitored by TLC). After concentration in vacuo, the residue was subsequently purified through column chromatography (hexanes/EtOAc: from 20:1 to 10:1) to afford tert-butyl (bicyclo[2.2.1]heptan-2-yl) carbamate as a white solid 1.37 g, 83% yield, m.p. 107-109° C.).
IR $v_{max}$ (neat)/cm$^{-1}$: 3357 (m), 2955 (m), 2874 (m), 1683 (s), 1521 (s), 1366 (m), 1308 (m), 1250 (m), 1171 (s), 1068 (m), 863 (m), 721 (m); $^1$H NMR (400 MHz, CDCl$_3$, 330 k) δ 4.31 (br s, 1H), 3.44 (s, 1H), 2.24-2.18 (m, 2H), 1.76-1.70 (m, 1H), 1.61-1.41 (in, 11H), 1.35-1.28 (m, 1H), 1.20-1.08 (m, 4H); $^{13}$C NMR (100 MHz, CDCl$_3$) δ 155.2, 79.0, 53.8, 42.5, 40.4, 35.6, 35.3, 28.4, 28.1, 26.4; HRMS (ESI, m/z): calcd for C$_{12}$H$_{21}$NO$_2$Na$^+$, [M+Na]$^+$, 234.1465, found 234.1469.

EXAMPLE 42

Olefin Isomerization Study

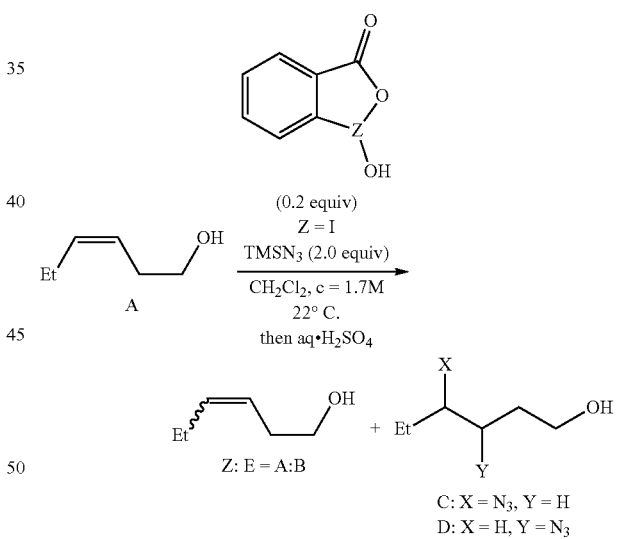

(Z)-Hex-3-en-1-ol is commercially available and was distilled before use.

To a flame-dried sealable 2-dram vial equipped with a stir bar were added A (200 mg, 2.0 mmol) and 1-hydroxy-1λ$^3$-benzo[d][1,2]iodaoxol-3(1H)-one (106 mg, 0.4 mmol). After this vial was evacuated and backfilled with N$_2$ twice, anhydrous CH$_2$Cl$_2$ (0.67 mL) was added, followed by the addition of TMSN$_3$ (526 µL, 4.0 mmol). The reaction mixture was stirred at 22° C. and quenched with aqueous H$_2$SO$_4$ (1 M, 1.5 mL) at 15, 40, 120, or 180 minutes. The organic layer was separated from the aqueous layer, which was extracted with Et$_2$O (3 mL×3). The combined organic layers were dried over anhydrous Na$_2$SO$_4$ and concentrated in vacuo. The reaction mixture was purified through column chromatography (hexanes/EtOAc: from 50:1 to 5:1) to afford C as colorless oil (62 mg, 43% yield) and D as colorless oil (47 mg, 33% yield) or to recover A as well as B.

4-Azidohexan-1-ol (C): IR $v_{max}$ (neat)/cm$^{-1}$: 3338 (br), 2937 (m), 2877 (m), 2092 (s), 1457 (m), 1340 (m), 1272 (s), 1250 (s), 1050 (s), 926 (m), 775 (w); $^1$H NMR (400 MHz, CDCl$_3$) δ 3.65 (t,J=5.9 Hz, 2H), 3.32-3.09 (m, 1H), 1.73-1.45 (m, 6H), 0.98 (t, J=7.4 Hz, 3H); $^{13}$C NMR (100 MHz, CDCl$_3$) δ 64.3, 62.4, 30.3, 29.2, 27.4, 10.4; HRMS (ESI, m/z): calcd for C$_6$H$_{13}$N$_3$ONa$^+$, [M+Na$^+$], 166.0951, found 166.0953.

3-Azidohexan-1-ol (D): IR $v_{max}$ (neat)/cm$^{-1}$: 3343 (br), 2960 (m), 2936 (m), 2876 (m), 2095 (s), 1463 (m), 1339 (m), 1254 (s), 1121 (w), 1047 (s), 905 (m), 744 (m); $^1$H NMR (400 MHz, CDCl$_3$) δ 3.80-3.72 (m, 2H), 3.51 (tt, J=9.2, 4.6 Hz, 1H), 1.84-1.73 (m, 1H), 1.71-1.63 (m, 1H), 1.61-1.33 (m, 4H), 0.95 (t,J=7.1 Hz, 3H); $^{13}$C NMR (100 MHz, CDCl$_3$) 59.9, 59.8, 36.8, 36.7, 19.3, 13.8; HRMS (ESI, m/z): calcd for C$_6$H$_{13}$N$_3$ONa$^+$, [M+Na$^+$], 166.0951, found 166.0953.

The yields of B, C, and D in addition to recovered A at the various time points are provided in Table 1 below.

TABLE 1

Yields isolated at Various Time Points for Hydroazidation of (Z)-Hex-3-en-1-ol

| Time | A recovered (%) | B yield (%) | C yield (%) | D yield (%) |
|---|---|---|---|---|
| 15 min | 25 | 51 | 11 | 10 |
| 40 min | 6 | 32 | 31 | 25 |
| 120 min | 2 | 17 | 43 | 33 |
| 180 min | 2 | 17 | 43 | 33 |

EXAMPLE 43

Trapping of Radical Intermediate by TEMPO During Hydroazidation of 1-Dodecene

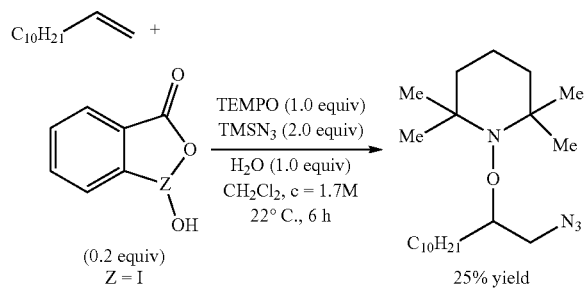

1-Dodecene is commercially available and was distilled before use.

To a flame-dried sealable 2-dram vial equipped with a stir bar were added 1-dodecene (222 µL, 1.0 mmol, 1.0 equiv), TEMPO (156 mg, 1.0 mmol, 1.0 equiv) and 1-hydroxy-1λ$^3$-benzo[d][1,2]iodaoxol-3(1H)-one (53 mg, 0.2 mmol, 0.2 equiv). After this vial was evacuated and backfilled with N$_2$ twice, anhydrous CH$_2$Cl$_2$ (0.33 mL) and H$_2$O (18 µL, 1.0 mmol, 1.0 equiv) were added via syringes. Freshly distilled TMSN$_3$ (263 µL, 2.0 mmol, 2.0 equiv) was added to the reaction and the mixture was stirred for 6 h at 22° C. until the olefin was not further consumed (monitored by TLC). The reaction was cooled to 0° C. Et$_2$O (2 mL) and saturated NaHCO$_3$ solution (1.5 mL) were added to quench the reaction and to remove any residual hydrazoic acid. The organic phase was separated from the aqueous phase, and the aqueous phase was extracted with Et$_2$O (3 mL×3). The combined organic phase was washed with brine (2 mL) and dried over Na$_2$SO$_4$. After concentration in vacuo, the residue was purified through column chromatography (hexanes/Et$_2$O: from 100:0 to 10:1) to afford 1-((1-azidododecan-2-yl)oxy)-2,2,6,6-tetramethylpiperidine as colorless oil (92 mg, 25% yield).

IR $v_{max}$ (neat)/cm$^{-1}$: 2924 (s), 2854 (m), 2098 (s), 1466 (m), 1376 (m), 1361 (m), 1259 (m), 1182 (m), 1045 (m), 890 (m), 788 (m); $^1$H NMR (400 MHz, CDCl$_3$) δ 3.94-3.85 (m, 1H), 3.53 (dd, J=12.4, 4.4 Hz, 1H), 3.34 (dd, J=12.4, 5.5 Hz, 1H), 1.84-1.70 (m, 1H), 1.52-1.41 (m, 5H), 1.35-1.20 (m, 18H), 1.14-1.12 (m, 12H), 0.88 (t, J=6.8 Hz, 3H); $^{13}$C NMR (100 MHz, CDCl$_3$) δ 80.90, 60.1, 59.8, 53.3, 40.3, 34.3, 34.1, 31.9, 31.3, 29.9, 29.6 (2 carbon merged), 29.3, 25.8, 22.7, 20.4, 17.2, 14.1; HRMS (ESI, m/z): calcd for C$_{21}$H$_{43}$N$_4$O$^+$, [M+H$^+$], 367.3431, found 367.3433.

EXAMPLE 44

Trapping of Radical Intermediate by TEMPO During Hydroazidation of Styrene

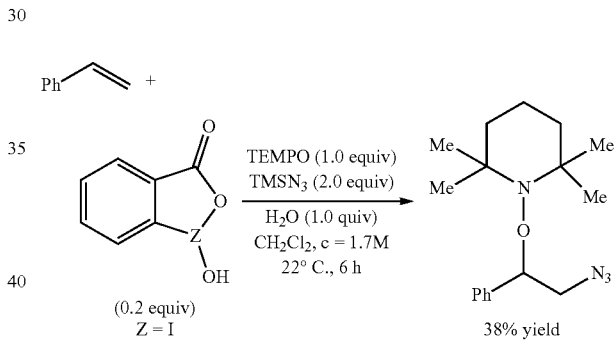

Styrene is commercially available and was distilled before use.

To a flame-dried sealable 2-dram vial equipped with a stir bar were added TEMPO (156 mg, 1.0 mmol, 1.0 equiv) and 1-hydroxy-1λ$^3$-benzo[d][1,2]iodaoxol-3(1H)-one (53 mg, 0.2 mmol, 0.2 equiv). After this vial was evacuated and backfilled with N$_2$ twice, anhydrous CH$_2$Cl$_2$ (0.33 mL), styrene (105 mg, 1.0 mmol, 1.0 equiv), and H$_2$O (18 µL, 1.0 mmol, 1.0 equiv) were added successively via syringes. Freshly distilled TMSN$_3$ (263 µL, 2.0 mmol, 2.0 equiv) was added to the reaction and the mixture was stirred for 6 h at 2.2° C. until the olefin was not further consumed (monitored by TLC). The reaction was cooled to 0° C., Et$_2$O (2 mL) and saturated NaHCO$_3$ solution (1.5 mL) were added to quench the reaction and to remove any residual hydrazoic acid. The organic phase was separated from the aqueous phase, and the aqueous phase was extracted with Et$_2$O (3 mL×3). The combined organic phase was washed with brine (2 mL) and dried over Na$_2$SO$_4$. After concentration in vacuo, the residue was purified through column chromatography (hexanes/Et$_2$O: from 100:0 to 10:1) to afford 1-(2-azido-1-phenylethoxy)-2,2,6,6-tetramethylpiperidine as colorless oil (115 mg, 38% yield) which is a known compound.

EXAMPLE 45

Deuteroazidation of 2-Norbornene

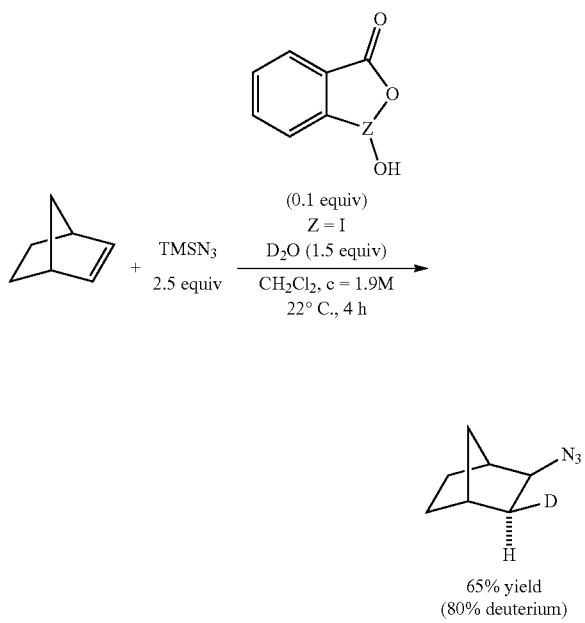

65% yield
(80% deuterium)

2-Norbornene is commercially available and was used directly without further purification.

To a flame-dried sealable 2-dram vial equipped with a stir bar were added 2-Norbornene (94 mg, 1.0 mmol, 1.0 equiv) and 1-hydroxy-$\lambda^3$-benzo[d][1,2]iodaoxol-3(1H)-one (27 mg, 0.1 mmol, 0.1 equiv). After this vial was evacuated and backfilled with $N_2$ twice, anhydrous $CH_2Cl_2$ (0.2 mL) and $D_2O$ (27 μL, 1.5 mmol, 1.5 equiv) were added via syringes. Freshly distilled $TMSN_3$ (328 μL, 2.5 mmol, 2.5 equiv) was added to the reaction and the mixture was stirred for 4 h at 22° C. until the olefin was fully consumed (monitored by TLC). The reaction was cooled to 0° C., Hexanes (2 mL) and saturated $NaHCO_3$ solution (1.5 mL) were added to quench the reaction and to neutralize the residual hydrazoic acid. The organic phase was separated from the aqueous phase, and the aqueous phase was extracted with hexanes (3 mL×3). The combined organic phase was washed with brine (2 mL) and dried over $Na_2So_3$. After concentration in vacuo, the residue was purified through column chromatography (100% hexanes) to afford 2-Azidobicyclo[2.2.1]heptane-3-d as a colorless oil (90 mg, 65% yield).

IR $v_{max}$ (neat)/cm$^{-1}$: 2957 (s), 2874 (m), 2085 (s), 1454 (m), 1339 (m), 1247 (s), 971 (s), 767 (w), 742 (w); $^1$H NMR (400 MHz, CDCl$_3$) δ 3.49-3.46 (m, 1H), 2.31-2.29 (m, 2H), 1.66-1.53 (m, 2H), 1.52-1.42 (m, 2H), 1.20-1.18 (m, 1H), 1.16-1.04 (m, 2H); $^{13}$C NMR (100 MHz, CDCl$_3$) δ 64.3, 41.8, 37.9 (q, J=20 Hz), 35.6, 35.3, 28.3, 25.9; LRMS: m/z (EI) calcd for $C_7H_{10}DN^+$, $[M-N_2]^+$, 110.1, found 110.1.

EXAMPLE 46

Synethesis of an Oligomeric Azide Product from Ethyl Acrylate

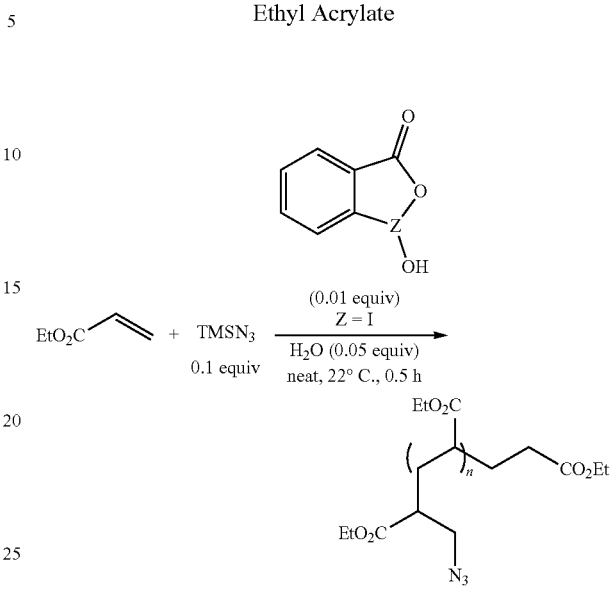

Ethyl acrylate is commercially available and was distilled before use.

To a flame-dried sealable 2-dram vial equipped with a stir bar was added 1-hydroxy-1$\lambda^3$-benzo[d][1,2]iodaoxol-3 (1H)-one (12 mg, 0.046 mmol, 0.01 equiv). After this vial was evacuated and backfilled with $N_2$ twice, ethyl acrylate (0.5 mL, 4.59 mmol, 1.0 equiv) and $H_2O$ (4.1 μL, 0.23 mmol, 0.05 equiv) were added via syringes. Freshly distilled trimethylsilylazide (60 μL, 0.46 mmol, 0.1 equiv) was added to the reaction, and the mixture was stirred at 22° C. During this period, polymer was generated gradually. After 0.5 h, $Et_2O$ (3 mL) and saturated $NaHCO_3$ solution (1.5 mL) were added to quench the reaction and to neutralize any residual hydrazoic acid. The organic phase was separated from the aqueous phase, and the aqueous phase was extracted with $Et_2O$ (3 mL×3). The combined organic phase was washed with brine (2 mL) and dried over $Na_2SO_4$. After concentration in vacuo, the product was obtained as a white solid.

EXAMPLE 47

Synthesis of a Deuterated Oligomeric Azide Product from Ethyl Acrylate

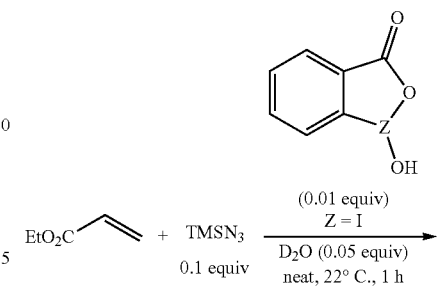

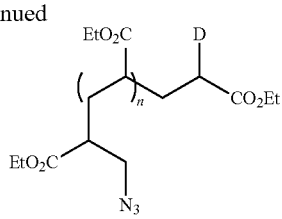

Ethyl acrylate is commercially available and was distilled before use.

To a flame-dried sealable 2-dram vial equipped with a stir bar was added 1-hydroxy-1λ³-benzo[d][1,2]iodaoxol-3(1H)-one (12 mg, 0.046 mmol, 0.01 equiv). After this vial was evacuated and backfilled with N₂ twice, Ethyl acrylate (0.5 mL, 4.59 mmol, 1.0 equiv) and D₂O (4.1 μL., 0.23 mmol, 0.05 equiv) were added via syringes. Freshly distilled trimethylsilylazide (60 μL, 0.46 mmol, 0.1 equiv) was added to the reaction and the mixture was stirred at 22° C. During this period, polymer was generated gradually. After 1 h, Et₂O (3 mL) and saturated NaHCO₃ solution (1.5 mL) were added to quench the reaction and to neutralize any residual hydrazoic acid. The organic phase was separated from the aqueous phase, and the aqueous phase was extracted with Et₂O (3 mL×3). The combined organic phase was washed with brine (2 mL) and dried over Na₂SO₄. After concentration in vacuo, the product was obtained as a white solid.

EXAMPLE 48

Deuteroazidation of 1-Dodecene with Deuterium Oxide as the Hydrogen Bond Donor

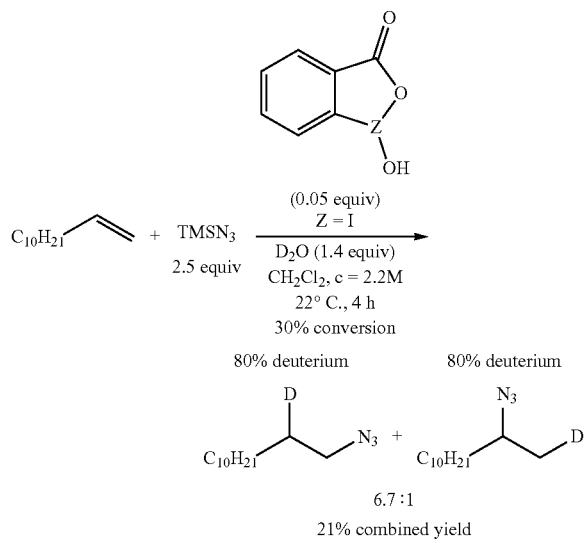

To a flame-dried sealable 3-dram vial equipped with a stir bar were added 1-dodecene (444 μL, 2.0 mmol, 1.0 equiv) and 1-hydroxy-1λ³-benzo[d][1,2]iodaoxol-3(1H)-one (27 mg, 0.1 mmol, 0.05 equiv). After this vial was evacuated and backfilled with N₂ twice, anhydrous CH₂Cl₂ (0.4 mL) and D₂O (51 μL, 2.8 mmol, 1.4 equiv) were added via syringes. Freshly distilled trimethylsilylazide (656 μL, 5.0 mmol, 2.5 equiv) was added to the reaction and the mixture was stirred for 4 h at 22° C. The reaction was cooled to 0° C., Hexanes (4 mL) and saturated NaHCO₃ solution (2 mL) were added to quench the reaction and to neutralize any residual hydrazoic acid. The organic phase was separated from the aqueous phase, and the aqueous phase was extracted with hexanes (4 mL×3). The combined organic phase was washed with brine (4 mL) and dried over Na₂SO₄. After concentration in vacuo, the residue was purified through column chromatography (100% hexanes) to afford the inseparable regioisomers 1-azidododecane-2-d and 2-azidododecane-1 -d as a colorless oil (89 mg, 21% yield, 6.7:1 ratio, 80% deuterium incorporation).

In order to confirm the structures of compound 1-azidododecane-2-d and 2-azidododecane-1-d, we further reduced the azido group with Ph₃P and subsequently protected with an acetyl group to afford N-(dodecyl-2-d)acetamide and N-(dodecan-2-yl-1-d)acetamide.

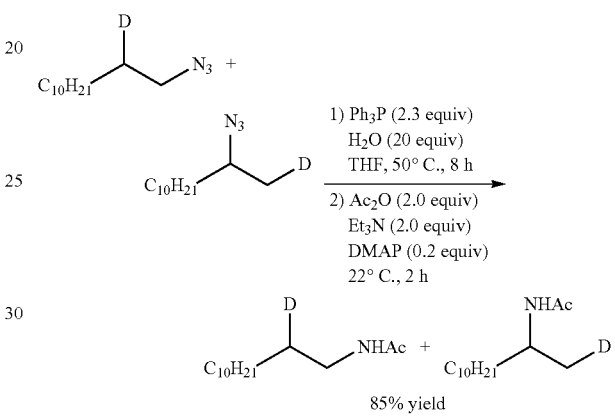

To a flame-dried sealable 3-dram vial equipped with a stir bar were added the inseparable products 1-azidododecane-2-d and 2-azidododecane-1-d (89 mg, 0.42 mmol, 1.0 equiv. After this vial was evacuated and backfilled with N₂ twice, THF (3 mL) and H₂O (38 μL, 2.1 mmol, 5.0 equiv) were added via syringes. Subsequently, triphenylphosphine (132 mg, 0.5 mmol, 1.2 equiv) in THF (1.2 mL) was added drop-wise to the reaction at 0° C. The reaction mixture was warmed up to 50° C. and stirred for 8 h (monitored by IR until the absorption of azido groups disappeared). The reaction mixture was cooled to room temperature, Et₃N (1171 μL, 0.84 mmol, 2.0 equiv), A_c2O (79 μL, 0.84 mmol, 2.0 equiv) and a solution of DMAP (10 mg, 0.08 mmol. 0.2 equiv) in THF (0.5 mL) were added to the above mixture at 0 ° C. The reaction mixture was warmed up to room temperature and kept stirring for additional 2 h until the intermediate was consumed (monitored by TLC). Saturated NaHCO₃ solution (2 mL) and ethyl acetate (3 mL) were added to quench the reaction. The organic phase was separated from the aqueous phase, and the aqueous phase was extracted with EtOAc (3 mL×3). The combined organic phase was washed with brine (4 mL) and. dried over Na₂SO₄. After concentration in vacuo, the residue was purified through column chromatography (hexanes/EtOAc: from 20:1 to 1:1) to afford N-(dodecyl-2-d)acetamide as a white solid (71 mg, 85% yield) along with N-(dodecan-2-yl-1-d)acetamide as a white solid (11 mg, 85% yield).

N-(dodecyl-2-d)acetamide: ¹H NMR (400 MHz, CDCl₃) δ 8.14 (brs, 1H), 3.27-3.25 (m, 2H), 2.19 (s, 3H), 1.57-1.51 (m, 1H), 1.35-1.21 (m, 18H), 0,86 (t, J=6.8 Hz, 3H); ¹³C NMR (100 MHz, CDCl₃) δ 172.3, 40.6 (d, J=6.5 Hz), 31.9, 29.6 (two carbons overlapped each other), 29.5 (two carbons overlapped each other), 29.3, 29.2 (d, J=3.1 Hz), 28.6 (q, J=20 Hz), 26.8 (d, J=9,9 Hz), 22.6, 21.7, 14.1; HRMS (ESI, m/z): calcd for $C_{14}H_{28}DNONa^+$, [M+Na$^+$], 251.2204, found 251.2201.

N-(dodecan-2-yl-1-d)acetamide: $^1$H NMR (400 MHz, CDCl$_3$) δ 5.24 (d, J=6.8 Hz, 1H), 4.05-3.84 (m, 1H), 1.95 (s, 3H), 1.42-1.21 (m, 18H), 1.12-1.08 (m, 2H), 0.87 (t, J=6.8 Hz, 3H); $^{13}$C NMR (100 MHz, CDCl$_3$) δ 169.3, 45.3 (d, J=5.1), 37.0 (d, J=2.6 Hz), 31.9, 29.6 (three carbon overlapped each other), 29.5, 29.3, 26.0, 23.6, 22.7, 20.7 (q, J=10.0 Hz), 14.1; HRMS (ESI, m/z):

calcd for $C_{14}H_{28}DNONa^+$, [M+Na$^+$], 251.2204, found 251.2201.

EXAMPLE 49

Deuteroazidation of 1-Dodecene with Deuterium Oxide and Trifluoroacetic Acid-d as the Hydrogen Bond Donor

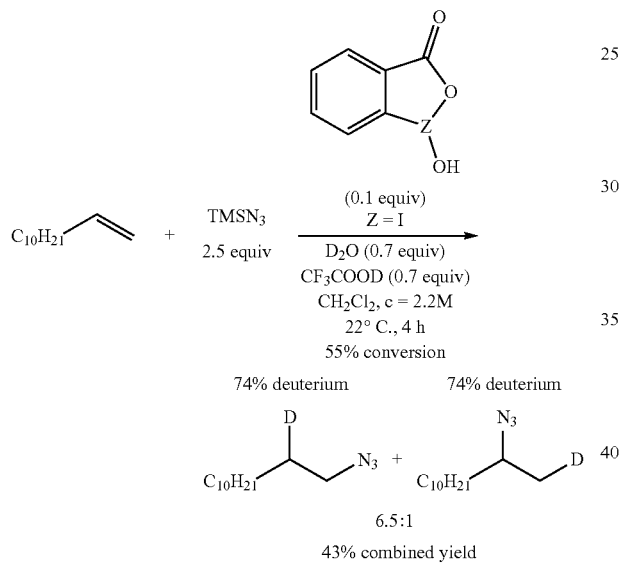

To a flame-dried sealable 3-dram vial equipped with a stir bar were added 1-Dodecene (444 µL, 2.0 mmol, 1.0 equiv) and 1-hydroxy-λ$^3$-benzo[d][1,2]iodaoxol-3(1H)-one (53 mg, 0.2 mmol, 0.1 equiv). After this vial was evacuated and backfilled with N$_2$ twice, anhydrous CH$_2$Cl$_2$ (0.4 mL) and D$_2$O (25 µL, 1.4 mmol, 0.7 equiv) were added via syringes. Freshly distilled trimethylsilylazide (656 µL, 5.0 mmol, 2.5 equiv) was added to the reaction followed by CF$_3$CO$_2$D (108 µL, 1.4 mmol, 0.7 equiv), and the mixture was stirred for 4 h at 22° C. The reaction was cooled to 0° C., hexanes (4 mL) and saturated NaHCO$_3$ solution (2 mL) were added to quench the reaction and to neutralize any residual hydrazoic acid. The organic phase was separated from the aqueous phase, and the aqueous phase was extracted with hexanes (4 mL×3) The combined organic phase was washed with brine (4 mL) and dried over Na$_2$SO$_4$. After concentration in vacuo, the residue was purified through column chromatography (100% hexanes) to afford the inseparable regioisomers 1-azidododecane-2-d and 2-azidododecane-1-d as a colorless oil as colorless oil (183 mg 43% yield, 6.5:1 ratio, 74% deuterium incorporation).

All publications and patent applications cited in this specification are herein incorporated by reference as if each individual publication or patent application were specifically and individually indicated to be incorporated by reference.

Although the foregoing invention has been described in some detail by way of illustration and example for the purposed of clarity of understanding, it will be readily apparent to one of ordinary skill in the art in light of the teaching of this invention that certain changes and modifications may be made thereto without departing from the spirit and scope of the invention as defined in the appended claims.

I claim:

1. A process for preparing an organic azide of Formula III comprising mixing an olefin of Formula I, a silylazide of Formula II, a hydrogen bond donor, and an organic promoter:

wherein:

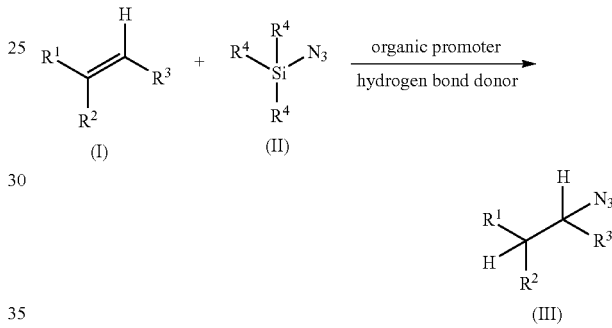

$R^1$ and $R^2$ are independently selected from hydrogen, alkyl, cycloalkyl, heteroalkyl, and heterocycloalkyl, wherein each of $R^1$ and $R^2$ that is not hydrogen is optionally substituted with one or more substituents selected from oxo, halo, cyano, azido, nitro, $R^7$, —OR$^7$, —N(R$^7$)(R$^7$), —(C=O)R$^7$, —(C=O)OR$^7$, —(C=O)N(R$^7$)(R$^7$), —O(C=O)R$^7$, —N(R$^7$)(C=O) R$^7$, —O(C=O)N(R$^7$)(R$^7$), and —N(R$^7$)(C=O)OR$^7$;

wherein at least one of $R^1$ and $R^2$ is not hydrogen;

$R^3$ is selected from hydrogen, alkyl, cycloalkyl, heteroalkyl, and heterocycloalkyl, wherein $R^3$ other than hydrogen is optionally substituted with one or more substituents selected from oxo, halo, cyano, azido, nitro, $R^7$, —OR$^7$, —N(R$^7$)(R$^7$), —(C=O)R$^7$, —(C=O)OR$^7$, —(C=O)N(R$^7$)(R$^7$), —O(C=O)R$^7$, —N(R$^7$)(C=O) R$^7$, —O(C=O)N(R$^7$)(R$^7$), and —N(R$^7$)(C=O)OR$^7$; or $R^1$ and $R^2$ or $R^2$ and $R^3$ are taken together with the carbons to which they are attached to form a cycloalkyl ring or an heterocycloalkyl ring, wherein each cycloalkyl or heterocycloalkyl ring is optionally substituted with one or more substituents selected from oxo, halo, cyano, azido, nitro, $R^7$, —OR$^7$, —N(R$^7$)(R$^7$), —(C=O)R$^7$, —(C=O)OR$^7$, —(C=O)N(R$^7$)(R$^7$), —O(C=O)R$^7$, —N(R$^7$)(C=O)R$^7$, —O(C=O)N(R$^7$)(R$^7$), and —N(R$^7$)(C=O)OR$^7$;

$R^4$ is independently selected at each occurrence from alkyl and cycloalkyl;

the organic promoter is selected from:

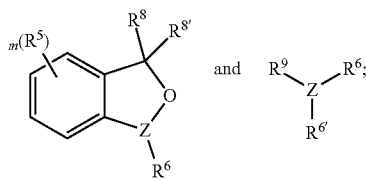

R⁵ is independently selected from hydrogen, halo, cyano, azido, nitro, R⁷, —OR', —N(R⁷)(R⁷), —(C=O)R⁷, —(C=O)OR⁷, —(C=O)N(R⁷)(R⁷), —O(C=O)R⁷, —N(R⁷)(C=O)R⁷, —O(C=O)N(R⁷)(R⁷), and —N(R⁷)(C=O)OR⁷;

m is 1, 2, 3, or 4;

Z is I;

R⁶ and R⁶' are independently selected from —O(C=O)R⁷, —O(SO₂)(R⁷), hydroxyl, and azido;

R⁷ is independently selected at each occurrence from hydrogen, alkyl, aryl, heteroalkyl, heteroaryl, cycloalkyl, heterocycloalkyl, and trialkylsilyl, each of which R⁷ other than hydrogen is optionally substituted with one or more substituents selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy; or two R⁷ groups may be brought together with the atoms to which they are attached to form a cycloalkyl, heterocycloalkyl, aryl, or heteroaryl ring, each of which ring is optionally substituted with one or more substituents selected from alkyl, heteroalkyl, cycloalkyl, heterocycloalkyl, aryl, heteroaryl, alkoxy, aryloxy, amino, alkylamino, dialkylamino, hydroxyl, halo, acylamino, aminoacyl, cyano, nitro, azido, acyl, acyloxy, carboxyl, carboxyl ester, alkanoyl, carboxamide, haloalkyl, and haloalkoxy;

R⁸ and R⁸' are independently selected from hydrogen, halo, cyano, azido, nitro, R⁷, —OR⁷, —N(R⁷)(R⁷), —(C=O)R⁷, —(C=O)OR⁷, —(C=O)N(R⁷)(R⁷), —O(C=O)R⁷, —N(R⁷)(C=O)R⁷, —O(C=O)N(R⁷)(R⁷), and —N(R⁷)(C=O)OR⁷; or R⁸ and R⁸' may be brought together with the carbon to which they are attached to form a cycloalkyl or heterocycloalkyl ring, each of which ring is optionally substituted with one or more substituents selected from oxo, halo, cyano, azido, nitro, R⁷, —OR', —N(R⁷)(R⁷), —(C=O)R⁷, —(C=O)OR⁷, —(C=O)N(R⁷)(R⁷), —O(C=O)R⁷, —N(R⁷)(C=O)R⁷, —O(C=O)N(R⁷)(R⁷), and —N(R⁷)(C=O)OR⁷; or R⁸ and R⁸' are brought together to form an oxo or imino group;

R⁹ is aryl or heteroaryl, wherein R⁹ is optionally substituted with one or more substituents selected from oxo, halo, cyano, azido, nitro, R⁷, —OR', —N(R⁷)(R⁷), —(C=O)R⁷, —(C=O)OR⁷, —(C=O)N(R⁷)(R⁷), —O(C=O)R⁷, —N(R⁷)(C=O)R⁷, —O(C=O)N(R⁷)(R⁷), and —N(R⁷)(C=O)OR⁷; and the hydrogen bond donor is water and optionally a second hydrogen bond donor.

2. The process of claim 1, wherein the olefin of Formula I is selected from

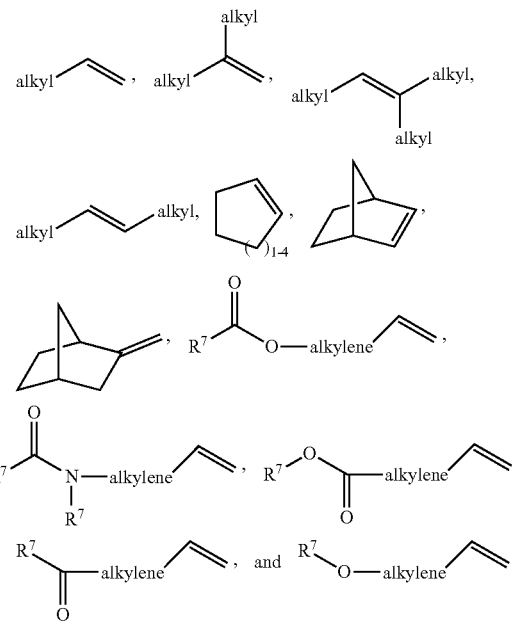

3. The process of claim 1, wherein the olefin of Formula I is selected from

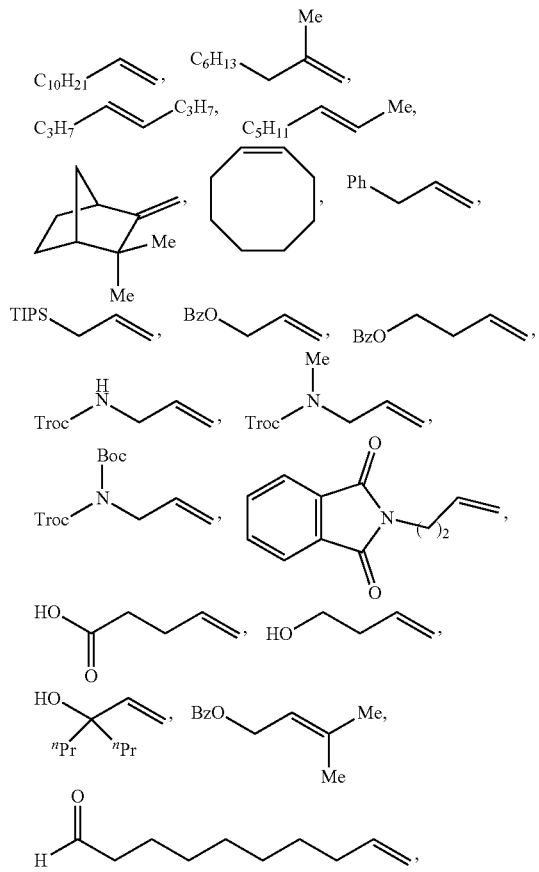

-continued

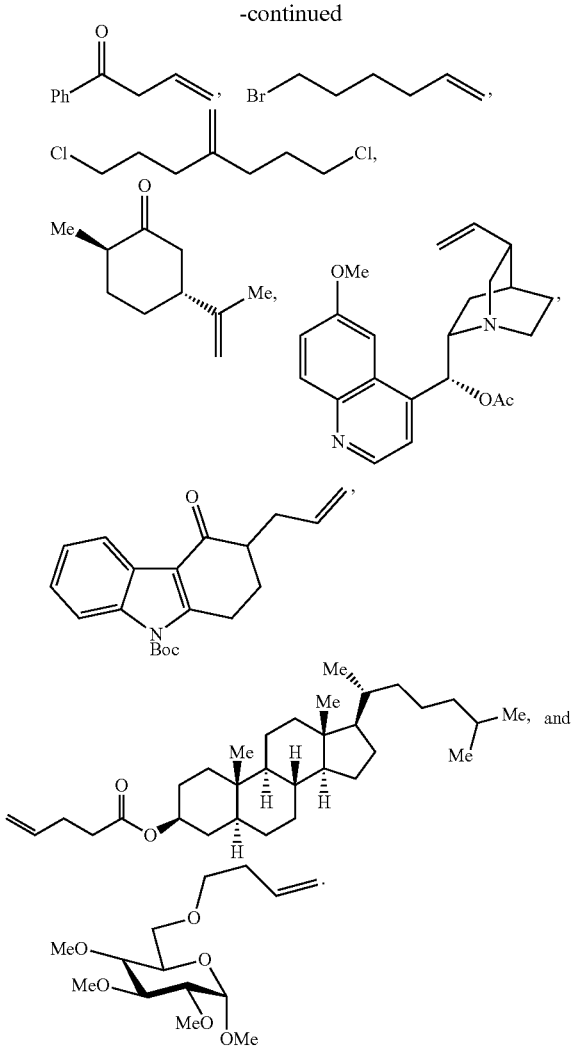

4. The process of claim 1, wherein the hydrogen bond donor is water.

5. The process of claim 1, wherein the hydrogen bond donor is water and a second hydrogen bond donor selected from formic acid, an alkylcarboxylic acid, a (cycloalkyl)carboxylic acid, a (heteroalkyl)carboxylic acid, a (heterocycloalkyl)carboxylic acid, an arylcarboxylic acid, an (heteroaryl)carboxylic acid, sulfuric acid, an alkylsulfonic acid, a (cycloalkyl)sulfonic acid, a (heteroalkyl)sulfonic acid, a (heterocycloalkyl)sulfonic acid, a arylsulfonic acid, and a (heteroaryl)sulfonic acid.

6. The process of claim 5, wherein the hydrogen bond donor is water and trifluoroacetic acid.

7. The process of claim 1, wherein the organic promoter is

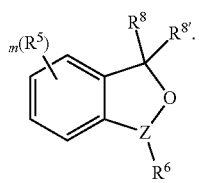

8. The process of claim 7, wherein the organic promoter is selected from

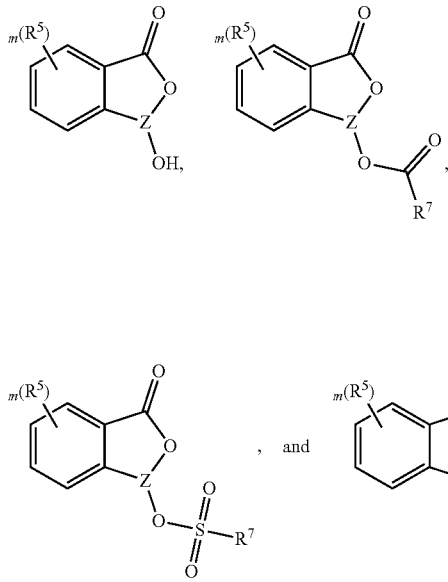

9. The process of claim 1, wherein the organic promoter is

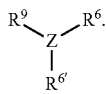

10. The process of claim 9, wherein the organic promoter is selected from

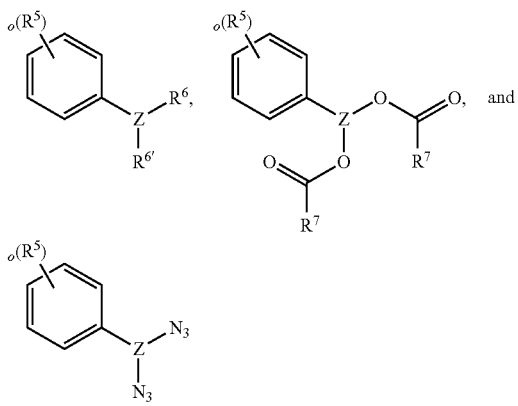

wherein o is 1, 2, 3, 4, or 5.

11. The process of claim 8, wherein $R^7$ is trifluoromethyl or trichloromethyl.

12. The process of claim 1, wherein $R^4$ is alkyl.

13. The process of claim 1, wherein the silylazide of Formula II is trimethylsilylazide or triethylsilylazide.

* * * * *

UNITED STATES PATENT AND TRADEMARK OFFICE
CERTIFICATE OF CORRECTION

PATENT NO. : 11,708,320 B2
APPLICATION NO. : 17/253966
DATED : July 25, 2023
INVENTOR(S) : Hao Xu It is certified that error appears in the above-identified patent and that said Letters Patent is hereby corrected as shown below:

In the Specification

Column 1, Line 11, after "which" delete "application".

Column 1, Line 13, after "are" delete "this application is".

Column 4, Line 23, delete "Z is 1;" and insert -- Z is I; --.

In the Claims

Claim 1, Line 13, delete "—OR'," and insert -- —OR$^7$, --.

Claim 1, Line 53, delete "—OR'," and insert -- —OR$^7$, --.

Claim 1, Line 62, delete "—OR'," and insert -- —OR$^7$, --.

Signed and Sealed this
Twenty-third Day of January, 2024

Katherine Kelly Vidal
*Director of the United States Patent and Trademark Office*